(12) United States Patent
Carstens et al.

(10) Patent No.: US 9,127,078 B2
(45) Date of Patent: Sep. 8, 2015

(54) METHODS AND COMPOSITIONS USING SPLICING REGULATORY PROTEINS INVOLVED IN TUMOR SUPPRESSION

(75) Inventors: Russ P. Carstens, Wynnewood, PA (US); Claude Warzecha, Philadelphia, PA (US); John Hogenesch, Wallingford, PA (US); Trey Sato, Madison, WI (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1074 days.

(21) Appl. No.: 13/003,968

(22) PCT Filed: Jul. 21, 2009

(86) PCT No.: PCT/US2009/051239
§ 371 (c)(1),
(2), (4) Date: Mar. 29, 2011

(87) PCT Pub. No.: WO2010/011642
PCT Pub. Date: Jan. 28, 2010

(65) Prior Publication Data
US 2011/0177967 A1    Jul. 21, 2011

Related U.S. Application Data

(60) Provisional application No. 61/082,435, filed on Jul. 21, 2008.

(51) Int. Cl.
| | | |
|---|---|---|
| *C12Q 1/68* | (2006.01) | |
| *C12P 21/06* | (2006.01) | |
| *C07K 14/47* | (2006.01) | |

(Continued)

(52) U.S. Cl.
CPC .......... *C07K 14/4702* (2013.01); *C12N 15/113* (2013.01); *C12Q 1/68* (2013.01); *C12Q 1/6886* (2013.01); *G01N 33/574* (2013.01); *C12N 2310/14* (2013.01); *C12Q 2600/106* (2013.01); *C12Q 2600/118* (2013.01);

(Continued)

(58) Field of Classification Search
CPC .. C12Q 1/68; C12Q 1/6886; C12Q 2600/106; C12Q 2600/118; C12Q 2600/136; C12Q 2600/158; G01N 33/574; G01N 33/68
See application file for complete search history.

(56) References Cited

U.S. PATENT DOCUMENTS

| | | |
|---|---|---|
| 2003/0219768 A1 | 11/2003 | Beebe |
| 2008/0113360 A1 | 5/2008 | Riker |
| 2010/0166713 A1* | 7/2010 | Dalton et al. ................ 424/93.7 |

OTHER PUBLICATIONS

Affymetrix GeneChip Human Genome U133A 2.0 Array, ftp://ftp.ebi.ac.uk/pub/databases/microarray/data/array/GEOD/A-GEOD-5356/A-GEOD-5356.adf.txt, downloaded on Feb. 14, 2013.*

(Continued)

*Primary Examiner* — Reza Ghafoorian
(74) *Attorney, Agent, or Firm* — Howson & Howson LLP

(57) ABSTRACT

Methods and compositions for diagnosis and prognosis of mammalian carcinoma or cancer derived from primary epithelial cells and tissue fibrosis are designed using newly identified epithelial cell-type specific splicing factors ESRP1 and ESRP2, which have roles in tumor suppression. Diagnostic reagents for the detection of these splicing factors in nucleotide or protein form are useful in such methods. Therapeutic compositions can provide epithelial cells with these factors to maintain FGFR2 and assist in suppressing metastasis. A high throughput splicing assay to identify compounds that change splicing events is described. RNCP1 is also identified as a splicing factor and a diagnostic for conditions characterized by inappropriate FGFR2-splicing.

11 Claims, 12 Drawing Sheets

(51) Int. Cl.
　　　*G01N 33/574*　　　(2006.01)
　　　*C12N 15/113*　　　(2010.01)
　　　*A61K 49/00*　　　(2006.01)
　　　*G01N 33/68*　　　(2006.01)

(52) U.S. Cl.
　　　CPC ... *C12Q 2600/136* (2013.01); *C12Q 2600/158* (2013.01); *G01N 33/68* (2013.01)

(56) References Cited

OTHER PUBLICATIONS

Harbig, A sequence-based identification of the genes detected by probesets on the Affymetrix U133 plus 2.0 array, Nucleic Acids Research, 2005, vol. 33, No. 3.*
Baraniak et al, Fox-2 mediates epithelial cell-specific fibroblast growth factor receptor 2 exon choice, Molecular and Cellular Biology, 26(4):1209-22 (Feb. 2006).
David and Manley, The search for alternative splicing regulators: new approaches offer a path to a splicing code, Genes & Development, 22(3):279-85 (Feb. 1, 2008).
Kalluri, Epithelial-mesenchymal transition and its implications for fibrosis, Journal of Clinical Investigation, 112(12):1776-84 (Dec. 2003).
Nurcombe et al, The proliferative and migratory activities of breast cancer cells can be differentially regulated by heparan sulfates, Journal of Biological Chemistry, 275(39):30009-18 (Sep. 29, 2000).
Singhirunnusorn et al, Critical roles of threonine 187 phosphorylation in cellular stress-induced rapid and transient activation of transforming growth factor-beta-activated kinase 1 (TAK1) in a signaling complex containing TAK1-binding protein TAB1 and TAB2, Journal of Biological Chemistry, 280(8):7359-68 (Feb. 25, 2005) Epub Dec. 7, 2004.
Arning et al, Mammalian splicing factor SF1 is encoded by variant cDNAs and binds to RNA, RNA, 2(8):794-810 (Aug. 1996).
Warzecha et al, ESRP1 and ESRP2 are epithelial cell-type-specific regulators of FGFR2 splicing, Molecular Cell, 33(5):591-601 (Mar. 13, 2009).
Archive! Ensembl Gene Report for ENSG00000104413. Ensemble Release 49 (online) Mar. 2008. Retrieved from the internet on Nov. 23, 2009.
International Search Report and Written Opinion dated Mar. 8, 2010 issued in corresponding PCT application No. PCT/US09/51239.
International Preliminary Report on Patentability dated Jan. 25, 2011 issued in corresponding PCT application No. PCT/US09/51239.
Allemand et al, Regulation of heterogenous nuclear ribonucleoprotein A1 transport by phosphorylation in cells stressed by osmotic shock, Proceedings of the National Academy of Science U S A, 8;102(10):3605-10. (Mar. 2005) Epub Feb. 28, 2005.
Arman et al, Fgfr2 is required for limb outgrowth and lung-branching morphogenesis, Proceedings of the National Academy of Science U S A, 96(21):11895-9 (Oct. 12, 1999).
Barberan-Soler et al, Alternative splicing regulation during *C. elegans* development: splicing factors as regulated targets, PLoS Genetics, 4(2):e1000001 (Feb. 29, 2008).
Barberi et al, Derivation of multipotent mesenchymal precursors from human embryonic stem cells, PLoS Medicine, 2(6):e161 (Jun. 2005) Epub Jun. 28, 2005.
Boutz et al, MicroRNAs regulate the expression of the alternative splicing factor nPTB during muscle development, Genes and Development, 21(1):71-84 (Jan. 1, 2007).
Carstens et al, Alternative splicing of fibroblast growth factor receptor 2 (FGF-R2) in human prostate cancer, Oncogene, 15(25):3059-65 (Dec. 18, 1997).
Carstens et al, An intronic sequence element mediates both activation and repression of rat fibroblast growth factor receptor 2 pre-mRNA splicing, Molecular and Cellular Biology, 18(4):2205-17 (Apr. 1998).
Carstens et al, An intronic splicing silencer causes skipping of the IIIb exon of fibroblast growth factor receptor 2 through involvement of polypyrimidine tract binding protein, Molecular and Cellular Biology, 20(19):7388-400 (Oct. 2000).
Cha et al, Involvement of fibroblast growth factor receptor 2 isoform switching in mammary oncogenesis, Molecular Cancer Research, 6(3):435-45 (Mar. 2008).
Dauwalder et al, A human homologue of the *Drosophila* sex determination factor transformer-2 has conserved splicing regulatory functions, Proceedings of the National Academy of Science U S A, 93(17):9004-9 (Aug. 20, 1996).
De Moerlooze et al, An important role for the IIIb isoform of fibroblast growth factor receptor 2 (FGFR2) in mesenchymal-epithelial signalling during mouse organogenesis, Development, 197(3)483-97 (Feb. 2000).
Feng et al, Fibroblast growth factor receptor 2 limits and receptor 1 accelerates tumorigenicity of prostate epithelial cells, Cancer Research, 57(23):5369-78 (Dec. 1, 1997).
Gerhard et al, The status, quality, and expansion of the NIH full-length cDNA project: The Mammalian Gene Collection (MGC), Genome Research, 14(10B):2121-7 (Oct. 2004).
Grose et al, The role of fibroblast growth factor receptor 2b in skin homeostasis and cancer development, EMBO Journal, 26(5):1268-78, (Mar. 7, 2007) Epub Feb. 15, 2007.
Hanamura et al, Regulated tissue-specific expression of antagonistic pre-mRNA splicing factors, RNA, 4(4):430-44 (Apr. 1998).
Hertel, Combinatorial control of exon recognition, Journal of Biological Chemistry, 283(3):1211-5 (Jan. 18, 2008) Epub Nov. 16, 2007.
Hieronymus and Silver, A systems view of mRNP biology, Genes & Development, 18(23):2845-60 (Dec. 1, 2004).
Hovhannisyan and Carstens, A novel intronic cis element, ISE/ISS-3, regulates rat fibroblast growth factor receptor 2 splicing through activation of an upstream exon and repression of a downstream exon containing a noncanonical branch point sequence, Molecular and Cellular Biology, 25(1):250-63 (Jan. 2005).
Hovhannisyan and Carstens, Heterogeneous ribonucleoprotein m is a splicing regulatory protein that can enhance or silence splicing of alternatively spliced exons, Journal of Biological Chemistry, 282(50):36265-74, (Dec. 14, 2007) Epub Oct. 24, 2007.
Hovhannisyan et al, Characterization of sequences and mechanisms through which ISE/ISS-3 regulates FGFR2 splicing, Nucleic Acids Research, 34(1):373-85 (Jan. 12, 2006).
Huang et al, Epithelial to mesenchymal transition in human breast epithelial cells transformed by 17beta-estradiol, Cancer Research, 67(23):11147-57 (Dec. 1, 2007).
Itoh et al, Preferential alternative splicing in cancer generates a K-sam messenger RNA with higher transforming activity, Cancer Research, 54(12):3237-41 (Jun. 15, 1994).
Kar et al, RBM4 interacts with an intronic element and stimulates tau exon 10 inclusion, Journal of Biological Chemistry, 281(34):24479-88, (Aug. 25, 2006) Epub Jun. 15, 2006.
Kuroyanagi et al, The Fox-1 family and SUP-12 coordinately regulate tissue-specific alternative splicing in vivo, Molecular and Cellular Biology, 27(24):8612-21 (Dec. 2007) Epub Oct. 8, 2007.
Ladd et al, The CELF family of RNA binding proteins is implicated in cell-specific and developmentally regulated alternative splicing, Molecular and Cellular Biology, 21(4):1285-96 (Feb. 2001).
Lin et al, Fibroblast growth factor receptor 2 tyrosine kinase is required for prostatic morphogenesis and the acquisition of strict androgen dependency for adult tissue homeostasis, Development, 134(4):723-34 (Feb. 2007) Epub Jan. 10, 2007.
Lynch and Maniatis, Assembly of specific SR protein complexes on distinct regulatory elements of the *Drosophila* doublesex splicing enhancer, Genes & Development, 10(16):2089-101 (Aug. 15, 1996).
Matsubara et al, Inhibition of growth of malignant rat prostate tumor cells by restoration of fibroblast growth factor receptor 2, Cancer Research, 58(7):1509-14 (Apr. 1, 1998).
McKee et al, A genome-wide in situ hybridization map of RNA-binding proteins reveals anatomically restricted expression in the developing mouse brain, BMC Developmental Biology, 5:14 (Jul. 20, 2005).
Min et al, Fgf-10 is required for both limb and lung development and exhibits striking functional similarity to *Drosophila* branchless, Genes & Development, 12(20):3156-61 (Oct. 15, 1998).

(56) References Cited

OTHER PUBLICATIONS

Newman et al, Identification of RNA-binding proteins that regulate FGFR2 splicing through the use of sensitive and specific dual color fluorescence minigene assays, RNA, 12(6):1129-41 (Jun. 2006) Epub Apr. 7, 2006.

Onder et al, Loss of E-cadherin promotes metastasis via multiple downstream transcriptional pathways, Cancer Research, 68(10):3645-54 (May 15, 2008).

Park et al, The miR-200 family determines the epithelial phenotype of cancer cells by targeting the E-cadherin repressors ZEB1 and ZEB2, Genes & Development, 22(7):894-907 (Apr. 1, 2008).

Ponthier et al, Fox-2 splicing factor binds to a conserved intron motif to promote inclusion of protein 4.1R alternative exon 16, Journal of Biological Chemistry, 281(18):12468-74 (May 5, 2006) Epub Mar. 14, 2006.

Pritsker et al, Diversification of stem cell molecular repertoire by alternative splicing, Proceedings of the National Academy of Science U S A, 102(40):14290-5 (Oct. 4, 2005) Epub Sep. 23, 2005.

Relogio et al, Alternative splicing microarrays reveal functional expression of neuron-specific regulators in Hodgkin lymphoma cells, Journal of Biological Chemistry 280(6):4779-84 (Feb. 11, 2005) Epub Nov. 16, 2004.

Savagner et al, Alternative splicing in fibroblast growth factor receptor 2 is associated with induced epithelial-mesenchymal transition in rat bladder carcinoma cells, Molecular Biology of the Cell, 5(8):851-62 (Aug. 1994).

Shankavaram et al, Transcript and protein expression profiles of the NCI-60 cancer cell panel: An integromic microarray study, Molecular Cancer Therapeutics, 6(3):820-32 (Mar. 2007) Epub Mar. 5, 2007.

Smith and Valcarcel, Alternative pre-mRNA splicing: The logic of combinatorial control, Trends in Biochemical Sciences, 25(8):381-8 (Aug. 2000).

Stamm, Regulation of alternative splicing by reversible protein phosphorylation, Journal of Biological Chemistry, 283(3):1223-7 (Jan. 18, 2008) Epub Nov. 16, 2007.

Thomson and Cunha, Prostatic growth and development are regulated by FGF10, Development, 126(16):3693-701 (Aug. 1999).

Wu et al, SRp54 (SFRS11), a regulator for tau exon 10 alternative splicing identified by an expression cloning strategy, Molecular and Cellular Biology, 26(18):6739-47 (Sep. 2006).

Xu et al, Fibroblast growth factor receptor 2 (FGFR2)-mediated reciprocal regulation loop between FGF8 and FGF10 is essential for limb induction, Development, 125(4):753-65 (Feb. 1998).

Yan et al, Exon switching and activation of stromal and embryonic fibroblast growth factor (FGF)-FGF receptor genes in prostate epithelial cells accompany stromal independence and malignancy, Molecular and Cellular Biology, 13(8):4513-22 (Aug. 1993).

Zhang et al, Receptor specificity of the fibroblast growth factor family. The complete mammalian FGF family, Journal of Biological Chemistry, 281(23):15694-700 (Jun. 9, 2006) Epub Apr. 4, 2006.

Zhang et al, Growth inhibition by keratinocyte growth factor receptor of human salivary adenocarcinoma cells through induction of differentiation and apoptosis, Proceedings of the National Academy of Science U S A, 98(20):11336-40 (Sep. 25, 2001) Epub Sep. 18, 2001.

Acevedo et al, Inducible FGFR-1 activation leads to irreversible prostate adenocarcinoma and an epithelial-to-mesenchymal transition, Cancer Cell, 12(6):559-71 (Dec. 2007).

Black, Mechanisms of alternative pre-messenger RNA splicing, Annual Review of Biochemistry, 72:291-336. Epub Feb. 27, 2003.

Blanco et al, Correlation of Snail expression with histological grade and lymph node status in breast carcinomas, Oncogene, 21(20):3241-6 (May 9, 2002).

Blencowe, Alternative splicing: new insights from global analyses, Cell, 126(1):37-47 (Jul. 14, 2006).

Boutros and Ahringer, The art and design of genetic screens: RNA interference, Nature Reviews: Genetics, 9(7):554-66 (Jul. 2008) Epub Jun. 3, 2008.

Cano et al, The transcription factor snail controls epithelial-mesenchymal transitions by repressing E-cadherin expression, Nature Cell Biology, 2(2):76-83 (Feb. 2000).

Chaffer et al, Mesenchymal to epithelial transition in development and disease, Cells Tissues Organs, 185(1-3):7-19 (Jun. 2007).

Charlet-Bn et al, Dynamic antagonism between ETR-3 and PTB regulates cell type-specific alternative splicing, Molecular Cell, 9(3):649-58 (Mar. 2002).

Cussenot et al, Immortalization of human adult normal prostatic epithelial cells by liposomes containing large T-SV40 gene, Journal of Urology, 146(3):881-6 (Sep. 1991).

Forch et al, Splicing regulation in Drosophila sex determination, Progress in Molecular and Subcellular Biology, 31:127-51 (2003).

Gregory et al, The miR-200 family and miR-205 regulate epithelial to mesenchymal transition by targeting ZEB1 and SIP1, Nature Cell Biology, 10(5):593-601 (May 2008) Epub Mar. 30, 2008.

Grose and Dickson, Fibroblast growth factor signaling in tumorigenesis, Cytokine & Growth Factor Reviews, 16(2):179-86 (Apr. 2005) Epub Feb. 5, 2005.

Hedley and Maniatis, Sex-specific splicing and polyadenylation of dsx pre-mRNA requires a sequence that binds specifically to tra-2 protein in vitro, Cell, 65(4):579-86 (May 17, 1991).

Hu and Fu, Spicing oncogenes, Nature Structural & Molecular Biology, 14(3):174-5 (Mar. 2007).

Ivanov et al, Identifying candidate colon cancer tumor suppressor genes using inhibition of nonsense-mediated mRNA decay in colon cancer cells, Oncogene,26(20):2873-84 (May 3, 2007) Epub Nov. 6, 2006.

Karni et al, The gene encoding the splicing factor SF2/ASF is a proto-oncogene, Nature Structural and Molecular Biology, 14(3):185-93, (Mar. 2007) Epub Feb. 18, 2007.

Keene, JD, RNA regulons: coordination of post-transcriptional events, Nature Reviews: Genetics, 8(7):533-43 (Jul. 2007).

Li et al, Neuronal regulation of alternative pre-mRNA splicing, Nature Reviews Neuroscience, 8(11):819-31 (Nov. 2007).

Licatalosi and Darnell, Splicing regulation in neurologic disease, Neuron, 52(1):93-101 (Oct. 5, 2006).

Lopez, AJ, Alternative splicing of pre-mRNA: developmental consequences and mechanisms of regulation, Annual Reviews of Genetics, 32:279-305 (1998).

Luqmani et al, Expression of FGFR2 BEK and K-SAM mRNA variants in normal and malignant human breast, European Journal of Cancer, 32A(3):518-24 (Mar. 1996).

Makeyev et al, The MicroRNA miR-124 promotes neuronal differentiation by triggering brain-specific alternative pre-mRNA splicing, Molecular Cell, 27(3):435-48 (Aug. 3, 2007).

Matlin et al, Understanding alternative splicing: towards a cellular code, Nature Reviews Molecular Cell Biology, 6(5):386-98 (May 2005).

McKeehan et al, The heparan sulfate-fibroblast growth factor family: diversity of structure and function, Progress in Nucleic Acid Research and Molecular Biology, 59:135-76 (1998).

Moffa et al, Differential signal transduction of alternatively spliced FGFR2 variants expressed in human mammary epithelial cells, Journal of Cellular Physiology, 210(3):720-31 (Mar. 2007).

Moffat and Sabatini, Building mammalian signalling pathways with RNAi screens, Nature Reviews Molecular Cell Biology, 7(3):177-87 (Mar. 2006).

Moody et al, The transcriptional repressor Snail promotes mammary tumor recurrence, Cancer Cell, 8(3):197-209 (Sep. 2005).

Orr-Urtreger et al, Developmental localization of the splicing alternatives of fibroblast growth factor receptor-2 (FGFR2), Developmental Biology, 158(2):475-86 (Aug. 1993).

Orwig et al, Genes involved in post-transcriptional regulation are overrepresented in stem/progenitor spermatogonia of cryptorchid mouse testes, Stem Cells, 26(4):927-38 (Apr. 2008) Epub Jan. 17, 2008.

Ricol et al, Tumour suppressive properties of fibroblast growth factor receptor 2-IIIb in human bladder cancer, Oncogene, 18(51):7234-43 (Dec. 2, 1999).

Rines et al, High-content screening of functional genomic libraries, Methods in Enzymology, 414:530-65 (2006).

Sekine, et al, Fgf10 is essential for limb and lung formation, Nature Genetics, 21(1):138-41 (Jan. 1999).

(56) References Cited

OTHER PUBLICATIONS

Sherwood et al, Prospective isolation and global gene expression analysis of definitive and visceral endoderm, Developmental Biology, 304(2):541-55 (Apr. 15, 2007) Epub Jan. 12, 2007.
Stamm et al, Function of alternative splicing, Gene, 344:1-20 (Jan. 3, 2005) Epub Dec. 10, 2004.
Thiery, Epithelial-mesenchymal transitions in tumour progression, Nature Reviews Cancer, 2(6):442-54 (Jun. 2002).
Tian and Maniatis, Positive control of pre-mRNA splicing in vitro, Science, 256(5054):237-40 (Apr. 10, 1992).
Ule et al, Nova regulates brain-specific splicing to shape the synapse, Nature Genetics, 37(8):844-52, (Aug. 2005) Epub Jul. 24, 2005.
Wakabayashi-Ito et al, fusilli, an essential gene with a maternal role in *Drosophila* embryonic dorsal-ventral patterning, Developmental Biology, 229(1):44-54 (Jan. 1, 2001).
Yang et al, Twist, a master regulator of morphogenesis, plays an essential role in tumor metastasis, Cell, 117(7):927-39 (Jun. 25, 2004).
Yang et al, Epithelial-mesenchymal transition: at the crossroads of development and tumor metastasis, Developmental Cell, 14(6):818-29 (Jun. 2008).
Yasumoto et al, Restoration of fibroblast growth factor receptor2 suppresses growth and tumorigenicity of malignant human prostate carcinoma PC-3 cells, Prostate, 61(3):236-42 (Nov. 1, 2004).
Heinicke, L., et al, The RNA Binding Protein RBM38 (RNPC1) Regulates Splicing during Late Erythroid Differentiation, PLoS One. 2013; 8(10): e78031. Published online Oct. 18, 2013.
Guha, M. et al, Mitochondrial retrograde signaling induces epithelial-mesenchymal transition and generates breast cancer stem cells., Oncogene, doi:10.1038/onc.2013/467; Nov. 4, 2013 (Abstract only).
Di Modugno, F et al, Splicing program of human MENA produces a previously undescribed isoform associated with invasive, mesenchymal-like breast tumors., Proc. Natl. Acad. Sci., USA, Nov. 20, 2012; 109(47):19280-5.
Warzecha, CC et al, Complex changes in alternative pre-mRNA splicing play a central role in the epithelial-to-mesenchymal transition (EMT)., Semin. Cancer Biol., Oct. 2012; 22(5-6):417-27.
Dittmar KA et al, Genome-wide determination of a broad ESRP-regulation posttranscriptional network by high-throughput sequencing., Mol. Cell. Biol., Apr. 2012; 32(8):1468-82.
Warzecha CC et al, An ESRP-regulated splicing programme is abrogated during the epithelial-mesenchymal transition. EMBP J. Oct. 2010; 29(19):3286-300.
Warzecha CC et al, the epithelial splicing factors ESRP1 and ESRP2 positively and negatively regulate diverse types of alternative splicing events. RNA Biol., Nov.-Dec. 2009; 6(5):546-62; Epub Nov. 22, 2009.

\* cited by examiner

Figure 1A
Figure 1B
Figure 1C
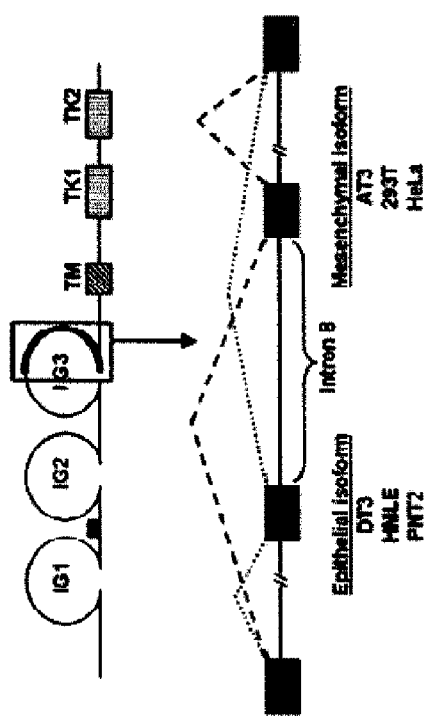
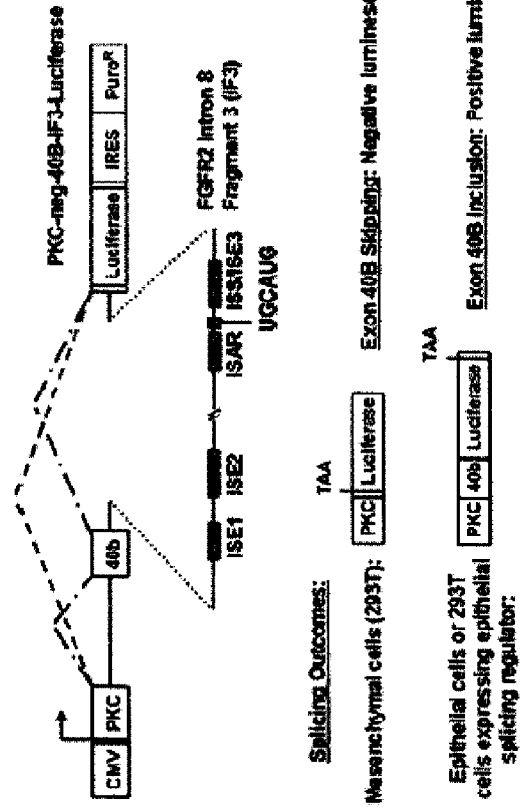

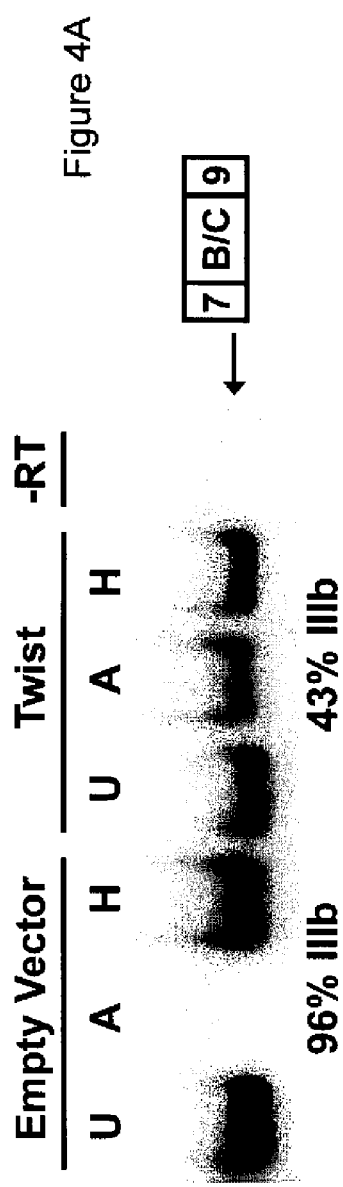
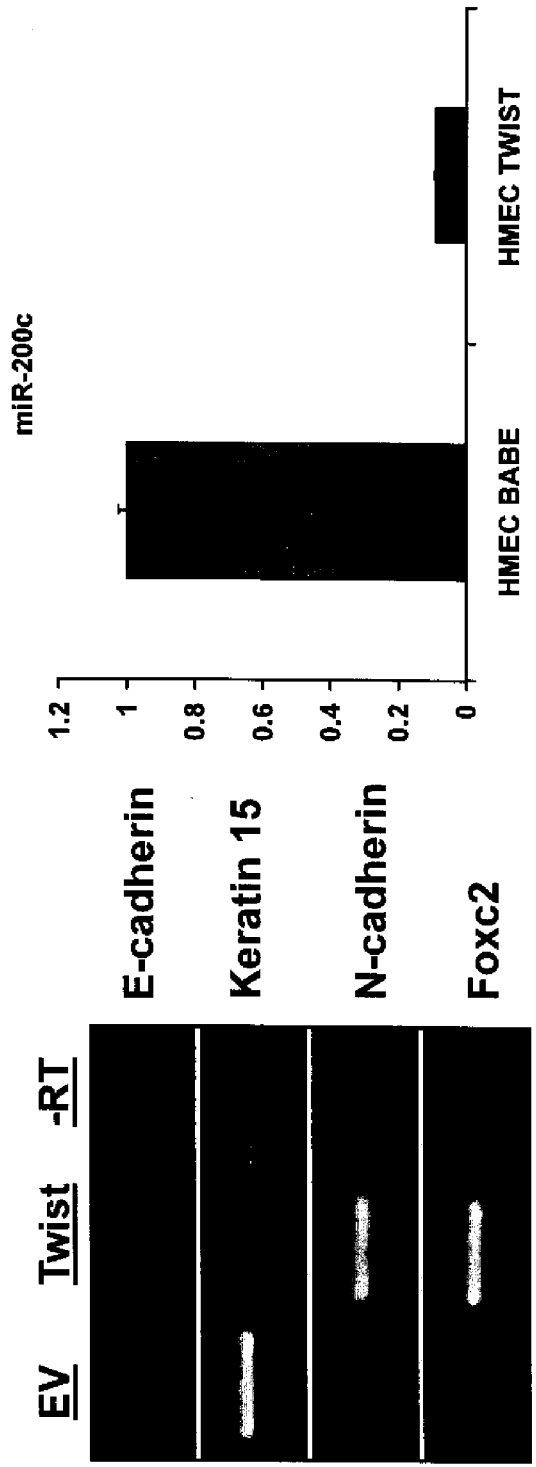
Figure 4A
Figure 4B
Figure 4C

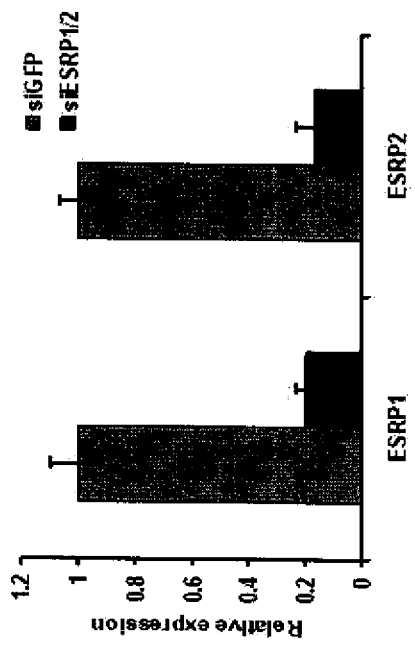
Figure 8 A
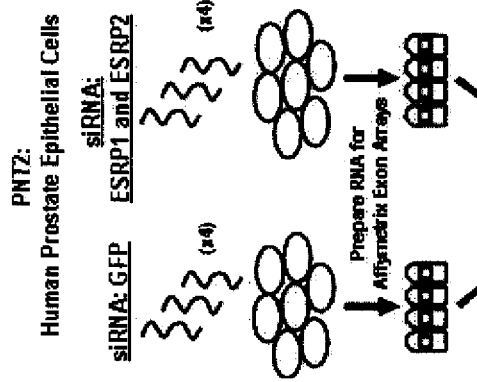
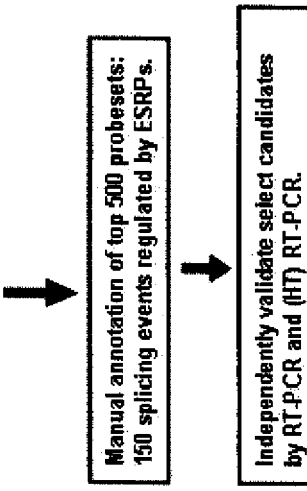
Figure 8 B

SEQUENCE LISTING

<160> NUMBER OF SEQ ID NOS: 80

<210> SEQ ID NO 1
<211> LENGTH: 57
<212> TYPE: DNA
<213> ORGANISM: Homo sapiens

<400> SEQUENCE: 1

```
ctctagtatg gtcctaaccc accagtgata gtatttttcct caagtcccat gactttt        57
```

<210> SEQ ID NO 2
<211> LENGTH: 72
<212> TYPE: DNA
<213> ORGANISM: Homo sapiens

<400> SEQUENCE: 2

```
gccacagatg gggaagtcac agccgtggag gaggcaccgg taaatgcatg tcccctgga        60 ttcaggccct gg                                                          72
```

<210> SEQ ID NO 3
<211> LENGTH: 78
<212> TYPE: DNA
<213> ORGANISM: Homo sapiens

<400> SEQUENCE: 3

```
gaacagatta taccattctc tcggcccggt gacaagagtg gcacgaaatg gctatcgaag       60
tcacatgaag gccagcag                                                    78
```

<210> SEQ ID NO 4
<211> LENGTH: 63
<212> TYPE: DNA
<213> ORGANISM: Homo sapiens

<400> SEQUENCE: 4

```
ctgtgtaatg aatcatagga cctgttgtca aaaacaatct gatttttcct tggagaatcc      60
cgt                                                                    63
```

<210> SEQ ID NO 5
<211> LENGTH: 130
<212> TYPE: DNA
<213> ORGANISM: Homo sapiens

<400> SEQUENCE: 5

```
tgtggtttct tcaagagaaa taagaaagat cattatgatg ccacatatca caaggctgag      60
atccatgctc agccatctga taaagagagg cttacttctg atgcatagta ttgatctact     120
tctgtaattg                                                            130
```

<210> SEQ ID NO 6
<211> LENGTH: 81
<212> TYPE: DNA
<213> ORGANISM: Homo sapiens

<400> SEQUENCE: 6

```
caatttctct atcgtgatat tgagttgttt gtttgttaca tagctggagt ccagggctac      60
cgctagctgt tggtaccggc t                                                81
```

<210> SEQ ID NO 7
<211> LENGTH: 43
<212> TYPE: DNA
<213> ORGANISM: Homo sapiens

<400> SEQUENCE: 7

```
tcctctggca ggaagggccc ctttagctga cagatacacg gac                        43
```

<210> SEQ ID NO 8
<211> LENGTH: 69
<212> TYPE: DNA

<213> ORGANISM: Homo sapiens

<400> SEQUENCE: 8

```
ctccattttc agtccggcag cacacattac tctgcgtaca aaacgattga acaccagatt    60
gcagttcag                                                           69
```

<210> SEQ ID NO 9
<211> LENGTH: 93
<212> TYPE: DNA
<213> ORGANISM: Homo sapiens

<400> SEQUENCE: 9

```
gttataaatg aagtggagaa agcacccaaa gagctgagaa aagagctcat gaaacgcagg    60
aaagaggagc ttgcacaaag ccagcatgct cag                                93
```

<210> SEQ ID NO 10
<211> LENGTH: 81
<212> TYPE: DNA
<213> ORGANISM: Homo sapiens

<400> SEQUENCE: 10

```
ctgatatgac gatctcaggg acatccagaa tgttgccaaa tgaagcagtt ttacggtggc    60
cccgtttagg cttggaatag g                                             81
```

<210> SEQ ID NO 11
<211> LENGTH: 103
<212> TYPE: DNA
<213> ORGANISM: Homo sapiens

<400> SEQUENCE: 11

```
ctgcagtaca tcagagagtt tgtcaccagt taagcaggct cctcggaagt cccctccga    60 cactgagggt cttgtaaaga gtctgccttc tggatctcac cag                     103
```

<210> SEQ ID NO 12
<211> LENGTH: 174
<212> TYPE: DNA
<213> ORGANISM: Homo sapiens

<400> SEQUENCE: 12

```
gaagagagcc ccctgagtgt gtctagccca gagggtactg gtacctggct gcattatacc    60
agtggtgtgg gtactgggcg tcgaagacgc agatcagggg aacaaatcac ttcttcccct   120
gtctccccca aatcattggc tttcacatcc agtatttttg gctcatggca acag         174
```

<210> SEQ ID NO 13
<211> LENGTH: 63
<212> TYPE: DNA
<213> ORGANISM: Homo sapiens

<400> SEQUENCE: 13

```
ctctggtaaa cagaattccg gcacagaatc cacaaataca tgacccgagc actcctttag    60
ctc                                                                 63
```

<210> SEQ ID NO 14
<211> LENGTH: 96
<212> TYPE: DNA
<213> ORGANISM: Homo sapiens

<400> SEQUENCE: 14

```
gttccccagc accgccactg ccatctgtta tgtctcctag cagggttgca gctagtcgac    60
```
tggctcagca aggaagtgat ttaattgttc ctgcag                                      96

<210> SEQ ID NO 15
<211> LENGTH: 48
<212> TYPE: DNA
<213> ORGANISM: Homo sapiens

<400> SEQUENCE: 15
gcaatgcgga atatcaatcc cagcacagca aattctccaa aatgtcag                         48

<210> SEQ ID NO 16
<211> LENGTH: 211
<212> TYPE: DNA
<213> ORGANISM: Homo sapiens

<400> SEQUENCE: 16
gtaccgtttt gcagagattc gctaccatcg ccctgaggag acccacaagg ggcgtacagt            60
tccagctcat gtggagacag tggttttatt tttcccggat gtttggcatt gccttcccac           120
ccgctcagag tgggaaaccc tctcccgagg atacaagcag cagctggtcg agaagcttca           180
gggtgaacgc aaggaggctg atggagaaca g                                         211

<210> SEQ ID NO 17
<211> LENGTH: 39
<212> TYPE: DNA
<213> ORGANISM: Homo sapiens

<400> SEQUENCE: 17
ccgcactcct gaggtgaaat gtcctgttcc tgacgaatc                                   39

<210> SEQ ID NO 18
<211> LENGTH: 55
<212> TYPE: DNA
<213> ORGANISM: Homo sapiens

<400> SEQUENCE: 18
cattttcaca tgtacggcag actcttgatt agtcatttct tggttatcca atctt                 55

<210> SEQ ID NO 19
<211> LENGTH: 33
<212> TYPE: DNA
<213> ORGANISM: Homo sapiens

<400> SEQUENCE: 19
tgccgctttc aggtgatgct acatctgctg gca                                         33

<210> SEQ ID NO 20
<211> LENGTH: 63
<212> TYPE: DNA
<213> ORGANISM: Homo sapiens

<400> SEQUENCE: 20
ctcttcctcc tcaatgcgag caggctctat cagcaggtta ttggcctggt caaacgacac            60
tcc                                                                          63

<210> SEQ ID NO 21
<211> LENGTH: 93
<212> TYPE: DNA
<213> ORGANISM: Homo sapiens

<400> SEQUENCE: 21

```
ctgcagtgtt cctttagcat ctttgccaat agctctggac cgccacctcc tgtgcgatct    60
tttttccttt ttgggacttt caaaagatcc acc                                 93

<210> SEQ ID NO 22
<211> LENGTH: 48
<212> TYPE: DNA
<213> ORGANISM: Homo sapiens

<400> SEQUENCE: 22
ctgcgggccc ggctgccagg agctgcccat ccaaagtccc ggagcacc                 48

<210> SEQ ID NO 23
<211> LENGTH: 69
<212> TYPE: DNA
<213> ORGANISM: Homo sapiens

<400> SEQUENCE: 23
ctgtaaaagg atctgctgtg ggtagtgtgt tagaagatcc cgaagagccc ggaacatacc    60
gaccaccac                                                            69

<210> SEQ ID NO 24
<211> LENGTH: 116
<212> TYPE: DNA
<213> ORGANISM: Homo sapiens

<400> SEQUENCE: 24
tttctctgta ataacaatgc aatttctgtt tgaactttca tatattcttg tgccatttta    60
caatgctgtt caaacactgc catagattct tggagtttg ggcacggtgc tagagg         116

<210> SEQ ID NO 25
<211> LENGTH: 42
<212> TYPE: DNA
<213> ORGANISM: Homo sapiens

<400> SEQUENCE: 25
caagaataat cacaacctta atgaccacca atgattttac aa                       42

<210> SEQ ID NO 26
<211> LENGTH: 63
<212> TYPE: DNA
<213> ORGANISM: Homo sapiens

<400> SEQUENCE: 26
tttacttcac ctcgcagtgg tatcttctga gtaaaccatc agtctgtgct tagttaacat    60
gtg                                                                  63

<210> SEQ ID NO 27
<211> LENGTH: 42
<212> TYPE: DNA
<213> ORGANISM: Homo sapiens

<400> SEQUENCE: 27
ctgaagccca acagtggaac tgtcagagag ggacggatcc tt                       42

<210> SEQ ID NO 28
<211> LENGTH: 102
<212> TYPE: DNA
<213> ORGANISM: Homo sapiens

<400> SEQUENCE: 28
tctcacccca gtctttgggc cgtatactcg gccctctgag agtgagctgt gggacatgtg    60
```

```
ggcagggatc cgcaacaatg acgggaactt agtcattgac ag                              102
```

<210> SEQ ID NO 29
<211> LENGTH: 129
<212> TYPE: DNA
<213> ORGANISM: Homo sapiens

<400> SEQUENCE: 29

```
tacaaacaaa atcccgaaat gttcaaacag acagctcgac tttgggcaca tgtgtatgct          60
ggagcaccag tttctagtcc agaatacacc aaaaaaatag aaaacctatg tgctatgggc         120
tttgatagg                                                                 129
```

<210> SEQ ID NO 30
<211> LENGTH: 45
<212> TYPE: DNA
<213> ORGANISM: Homo sapiens

<400> SEQUENCE: 30

```
aatgtctttc aatcttcctt ggccagacag atcatgtaca gagcg                          45
```

<210> SEQ ID NO 31
<211> LENGTH: 84
<212> TYPE: DNA
<213> ORGANISM: Homo sapiens

<400> SEQUENCE: 31

```
ctgcaaagaa agaggcgctc ctgatcaggc ggagcggacc ctgctcagag aatgcccgcc          60
tggggctgca gaactgtgaa agac                                                 84
```

<210> SEQ ID NO 32
<211> LENGTH: 120
<212> TYPE: DNA
<213> ORGANISM: Homo sapiens

<400> SEQUENCE: 32

```
gagctgaaca accgcctggc tgcagagatc acacggttgc ggacgctgct gactggggac          60
ggcggtgggg aggccactgg gtcacccctt gcacagggca aggatgccta tgaactagag         120
```

<210> SEQ ID NO 33
<211> LENGTH: 96
<212> TYPE: DNA
<213> ORGANISM: Homo sapiens

<400> SEQUENCE: 33

```
ccgtagcctt tgttccgcct tccacttcag gtggcccagg ctctgactgg ccactctctg          60
gtagtgcagg gacaaccttg ctgcctgcca cctcag                                    96
```

<210> SEQ ID NO 34
<211> LENGTH: 90
<212> TYPE: DNA
<213> ORGANISM: Homo sapiens

<400> SEQUENCE: 34

```
ctgcggtggc tgtgtggtgc tgaaccgata ctctccttgt ttgtctcggt tgaacacaac          60
tttccaaagg accatgtcaa ggaagaagtt                                           90
```

<210> SEQ ID NO 35
<211> LENGTH: 154
<212> TYPE: DNA

<213> ORGANISM: Homo sapiens

<400> SEQUENCE: 35

```
tgaaagaaag gatgtcttaa gagaagctga aattttacac aaagctagat ttagttacat    60
tcttccaatt tgggaatttt gcaatgagcc tgaattttg ggaatagtta ctgaatacat    120
gccaaatgga tcattaaatg aactcctaca tagg                               154
```

<210> SEQ ID NO 36
<211> LENGTH: 111
<212> TYPE: DNA
<213> ORGANISM: Homo sapiens

<400> SEQUENCE: 36

```
atttgaccac ttcatcaagt tcatctggtc ctagagtttc tggctcacct tgtcatcata    60
gtgattctaa ttcttctgag aaacacatgt cacgagcctc tcaaagagaa g            111
```

<210> SEQ ID NO 37
<211> LENGTH: 186
<212> TYPE: DNA
<213> ORGANISM: Homo sapiens

<400> SEQUENCE: 37

```
gctgacattt ggtcattggg aattactgct attgaactag ccaagggaga gccacctaac    60
tccgatatgc atccaatgag agttctgttt cttattccca aaaacaatcc tccaactctt    120
gttggagact ttactaagtc ttttaaggag tttattgatg cttgcctgaa caaagatcca    180
tcattt                                                              186
```

<210> SEQ ID NO 38
<211> LENGTH: 137
<212> TYPE: DNA
<213> ORGANISM: Homo sapiens

<400> SEQUENCE: 38

```
ctgtctgcca actttttttc tgcgttagtg tgtttcttct tcgctttcac ttttttggca    60
ggttcttgcg aaagtggtct ttcaatctgg gatgtacttt cttcctcctc attccgtttc    120
gttttttga tggtttg                                                   137
```

<210> SEQ ID NO 39
<211> LENGTH: 66
<212> TYPE: DNA
<213> ORGANISM: Homo sapiens

<400> SEQUENCE: 39

```
cctccccatc tctctgcaga tgcattgttt tgaaatcaat gagggaaaa gtgatagggc     60
atgacg                                                              66
```

<210> SEQ ID NO 40
<211> LENGTH: 118
<212> TYPE: DNA
<213> ORGANISM: Homo sapiens

<400> SEQUENCE: 40

```
tgttttacct caatcatata tccacacaag tgcttctctt gacatttctc gaaaatggga    60
gaagaagaat aaaattgttt atcctccaca actgcctgga gaacctcgga gaccagca     118
```

<210> SEQ ID NO 41
<211> LENGTH: 126

<212> TYPE: DNA
<213> ORGANISM: Homo sapiens

<400> SEQUENCE: 41

```
ctgaccaatg ccatgccata gagcagtcta agttcatcag tgcccaagcc accagttaca    60
tccaagagct tacagcgtat caggtcagca gtagaagcca ctgccagagg gagttcgttg   120
cctgac                                                              126
```

<210> SEQ ID NO 42
<211> LENGTH: 102
<212> TYPE: DNA
<213> ORGANISM: Homo sapiens

<400> SEQUENCE: 42

```
attccctgct gtgaacgtga acatcggaag gaaaataatg gcaagcctcc cttctgggat    60
cttagtgcag acagctgcga ggactgtcat gatggcacca ga                      102
```

<210> SEQ ID NO 43
<211> LENGTH: 48
<212> TYPE: DNA
<213> ORGANISM: Homo sapiens

<400> SEQUENCE: 43

```
attgcatcat cagagaaaat acacccagtc attttgcggt gaaaacat                 48
```

<210> SEQ ID NO 44
<211> LENGTH: 138
<212> TYPE: DNA
<213> ORGANISM: Homo sapiens

<400> SEQUENCE: 44

```
ttgtccagtg gagccccaaa atagaagcaa gatgaatatt ccattccgca ttggcaatgc    60
caaaggagat gatgctttag aaaaaagatt tcttgataaa gctcttgaac tcaatatgtt   120
gtccttgaaa gggcatag                                                 138
```

<210> SEQ ID NO 45
<211> LENGTH: 84
<212> TYPE: DNA
<213> ORGANISM: Homo sapiens

<400> SEQUENCE: 45

```
ctactgtaaa ctctcctagt actacaccac ccactgtcac cactaacatg cctgttacta    60
acagaatcga taaacaaagg aatg                                           84
```

<210> SEQ ID NO 46
<211> LENGTH: 126
<212> TYPE: DNA
<213> ORGANISM: Homo sapiens

<400> SEQUENCE: 46

```
tcccaccctg gcagagaggc atgcacactg acgttatcca caccatcatt tgccaactga    60
caagccaata attagagcga ttatggcaac cagaaccact gacacagcaa taattatcca   120
cttttt                                                              126
```

<210> SEQ ID NO 47
<211> LENGTH: 51
<212> TYPE: DNA
<213> ORGANISM: Homo sapiens

<400> SEQUENCE: 47
tgtgtgactt tgggtcagta ccttcccctc tctggacctc agtctgacca t     51

<210> SEQ ID NO 48
<211> LENGTH: 50
<212> TYPE: DNA
<213> ORGANISM: Homo sapiens

<400> SEQUENCE: 48
cttgatttgc agtcctctga acagtttggg tttatcactc ctaacaaaag     50

<210> SEQ ID NO 49
<211> LENGTH: 31
<212> TYPE: DNA
<213> ORGANISM: Homo sapiens

<400> SEQUENCE: 49
cttgccgata ctgcttcttt gaaggaagaa a     31

<210> SEQ ID NO 50
<211> LENGTH: 57
<212> TYPE: DNA
<213> ORGANISM: Homo sapiens

<400> SEQUENCE: 50
ctgcagaggc cacagtcaca ggctcagttt cattgtcatt ttcaactcct gaaaact     57

<210> SEQ ID NO 51
<211> LENGTH: 108
<212> TYPE: DNA
<213> ORGANISM: Homo sapiens

<400> SEQUENCE: 51
atgaaaatga taatattgag atagatacta acgaggagat ccctgaaggc tttgttgtag     60
gaggtggaga tgaacttact aacttagaaa atgaccttga tactcccg     108

<210> SEQ ID NO 52
<211> LENGTH: 73
<212> TYPE: DNA
<213> ORGANISM: Homo sapiens

<400> SEQUENCE: 52
cttatgattg acagttcaca ctggaatcaa aggtgaattc atgggagtag aggtgagata     60
tcgttaggca agt     73

<210> SEQ ID NO 53
<211> LENGTH: 45
<212> TYPE: DNA
<213> ORGANISM: Homo sapiens

<400> SEQUENCE: 53
gggcggcgaa gaggacccgc aggctgcaag gagcaacagc gatgg     45

<210> SEQ ID NO 54
<211> LENGTH: 207
<212> TYPE: DNA
<213> ORGANISM: Homo sapiens

<400> SEQUENCE: 54
ctgtattctg ttgggatggg gtaagacccg tgagcgacgg tcaaaggtct gtcccacgtg     60
gtaaggcggg aaccgccgct gccggtactg agggcgatac tggggcggc gcagctgatt     120

```
ccgggcccca gagaactgcc tatcagtggc aggggggtca atccttcac tgctgccgct      180 cccttcctcc tcctcctccc cagcgta                                         207

<210> SEQ ID NO 55
<211> LENGTH: 81
<212> TYPE: DNA
<213> ORGANISM: Homo sapiens

<400> SEQUENCE: 55
aggatcagct ggtgcaatgt tagaatcaaa ttgggtcaga gtttgtgagc ttgaagagcg      60
ttcactaaat gtctcccact g                                                81

<210> SEQ ID NO 56
<211> LENGTH: 54
<212> TYPE: DNA
<213> ORGANISM: Homo sapiens

<400> SEQUENCE: 56
tggcaaagta gaaagaaggg cttgtctcct tgttgtatgg taatttggga catg            54

<210> SEQ ID NO 57
<211> LENGTH: 296
<212> TYPE: DNA
<213> ORGANISM: Homo sapiens

<400> SEQUENCE: 57
cttggagtgc agttataaag tgctctgcta aaactgcact ctgccaggtg agtttattcc      60
atcctccatc attttttctta cagattttttg cctcctgatc tctggcaagc ctttgctctc   120
agttctagga tctgtggctg tttcctgcac accctgtata tgctgagcat caatctctcc    180
tagtgttctg ccttttttccc cattcccggt tctctctccg gccacatttg tgacactaat   240
ctcaggaatg acaaggatgc ccaattcagt agcatcatta ttgttgtcag gttgct         296

<210> SEQ ID NO 58
<211> LENGTH: 81
<212> TYPE: DNA
<213> ORGANISM: Homo sapiens

<400> SEQUENCE: 58
ctttccaaga gattaatgga caagaaattc aaagagccaa tcaccagcgc attacaaaag     60
ctagagcaac atggtggaag t                                               81

<210> SEQ ID NO 59
<211> LENGTH: 144
<212> TYPE: DNA
<213> ORGANISM: Homo sapiens

<400> SEQUENCE: 59
ccgaacatgt ggctgcaatt tccttgttag cagcatcagg ggcatgggcc caagggttgg     60
tttcacgcac aggcattgct acgggtgcta gagcagtatg ggctggctta gcaagcacat   120
ggaaggctga gtcagtgcca ttag                                            144

<210> SEQ ID NO 60
<211> LENGTH: 69
<212> TYPE: DNA
<213> ORGANISM: Homo sapiens

<400> SEQUENCE: 60
```

```
cgaaacagaa ttgttagtgc tgctatgacc attagctggg gactgtctgg aagtggaagg    60
ggaatctct                                                             69

<210> SEQ ID NO 61
<211> LENGTH: 138
<212> TYPE: DNA
<213> ORGANISM: Homo sapiens

<400> SEQUENCE: 61
atcagccctc atacatgctg ttactcttgg agaaaaagat atagtcattc ttcttctgca    60
gcacaatatt gatgtgcttt ctcgagatgc gtttcgaaag attgcaggag attatgccat   120
tgaggctaag aatagagt                                                  138

<210> SEQ ID NO 62
<211> LENGTH: 105
<212> TYPE: DNA
<213> ORGANISM: Homo sapiens

<400> SEQUENCE: 62
ggagaggttc gttccggccc atccagtctt ctctgaccaa agcagctctg tctcggccga    60
tcgtgcccaa ggtccttcca ccccaggcca cgagtcacct ggcca                   105

<210> SEQ ID NO 63
<211> LENGTH: 117
<212> TYPE: DNA
<213> ORGANISM: Homo sapiens

<400> SEQUENCE: 63
cttgggcagc agcttgggga agtgcttcac aatgatacca aaggtgggcc cgctgagggc    60
caggtgcctg gatcgggggt ctggctccac ggtgtagctt gcagcctggt caggatc      117

<210> SEQ ID NO 64
<211> LENGTH: 270
<212> TYPE: DNA
<213> ORGANISM: Homo sapiens

<400> SEQUENCE: 64
ctgtggactg ggttccaatc aggggctggc tctccatatc atcgtgcaag gcaaccacac    60
tgactgtgta ctcagaaccc ggtctgaggc cttgcagctc tgcagtgtct tcttcaccat   120
caggtgcagg gaatagctca tggattccat cctcagggct cgagtaggtc accctgtacc   180
tggaaacttg cccctgtggg ctttcccaag caattttgat ggaatcgaca tccacatcag   240
tgaatgccag tcctttaggg cgatcaatgt                                    270

<210> SEQ ID NO 65
<211> LENGTH: 93
<212> TYPE: DNA
<213> ORGANISM: Homo sapiens

<400> SEQUENCE: 65
ctgtgttgat tctgcacttg gactggggtt ggatccccat ggggcagctt ttggaccacc    60
agtgttaacc caggaattgg agcgatctaa acc                                 93

<210> SEQ ID NO 66
<211> LENGTH: 30
<212> TYPE: DNA
<213> ORGANISM: Homo sapiens

<400> SEQUENCE: 66
```

```
atggtgacct ctgaattgta cccaccacag                                      30

<210> SEQ ID NO 67
<211> LENGTH: 836
<212> TYPE: DNA
<213> ORGANISM: Homo sapiens

<400> SEQUENCE: 67
tgcagatgga cgttttgaag ggaccagtac gaaaacagtc atcaggtaca atggcactgt     60
cacctggact ccaccggcaa actacaaaag ttcctgtacc atagatgtca cgttttccc    120 atttgacctt cagaactgtt ccatgaaatt tggttcttgg acttatgatg gatcacaggt    180
tgatataatt ctagaggacc aagatgtaga caagagagat ttttttgata atggagaatg    240
ggagattgtg agtgcaacag ggagcaaagg aaacagaacc gacagctgtt gctggtatcc    300
gtatgtcact tactcatttg taatcaagcg cctgcctctc ttttatacct tgttccttat    360 aatacccctgt attgggctct cattttaac tgtacttgtc ttctatcttc cttcaaatga    420
aggtgaaaag atttgtctct gcacttcagt acttgtgtct ttgactgtct tccttctggt    480
tattgaagag atcataccat catcttcaaa agtcatacct ctaattggag agtatctggt    540
atttaccatg atttttgtga cactgtcaat tatggtaacc gtcttcgcta tcaacattca    600
tcatcgttct tcctcaacac ataatgccat ggcgcctttg gtccgcaaga tatttcttca    660
cacgcttccc aaactgcttt gcatgagaag tcatgtagac aggtacttca ctcagaaaga    720
ggaaactgag agtggtagtg gaccaaaatc ttctagaaac acattggaag ctgcgctcga    780
ttctattcgc tacattacaa gacacatcat gaaggaaaat gatgtccgtg aggtct        836

<210> SEQ ID NO 68
<211> LENGTH: 168
<212> TYPE: DNA
<213> ORGANISM: Homo sapiens

<400> SEQUENCE: 68
cctcgccccc caccctctc cccctggg ggcccgtac cctcggcatt gcctaacgga         60
cccccgtccc ccgctccgg ccgtgacccc ttggccatac tgagcgagat cagtaagtcg    120
gtcaaaccga ggctagcatc cttccgcagc cttcgaggca gccgtggg               168

<210> SEQ ID NO 69
<211> LENGTH: 72
<212> TYPE: DNA
<213> ORGANISM: Homo sapiens

<400> SEQUENCE: 69
gctgagctgg ctgaccgacc caatccccct acccgccctc tgcccgctga cccggtggtg     60
agaagcccga ag                                                         72

<210> SEQ ID NO 70
<211> LENGTH: 459
<212> TYPE: DNA
<213> ORGANISM: Homo sapiens

<400> SEQUENCE: 70
cttccagttt cccagccagt accaactatc caaggcgaac ctcagatccc agttgcgaca     60
caaccctcgg ttgttccagt ccactctggt gctcatttcc ttccagtggg acagccgctc    120
cctactccct tgctccctca gtaccctgtc tctcagattc ccatatcaac tcctcatgtg    180
```

```
tctacggctc agacaggttt ctcatccctt cccatcacaa tggcagctgg cattactcag    240
cctctgctca cgttggcttc atctgctaca acagctgcga tcccgggggt atcaactgtg    300
gttcctagtc agcttccaac ccttctgcag cctgtgactc agctgccaag tcaggttcac    360
ccacagctcc tacaaccagc agttcagtcc atgggaatac cagctaacct tggacaagct    420
gctgaggttc cactttcctc tggagatgtt ctgtaccag                           459

<210> SEQ ID NO 71
<211> LENGTH: 102
<212> TYPE: DNA
<213> ORGANISM: Homo sapiens

<400> SEQUENCE: 71
gatggataag gtgggggatg ccctggagga agtgctcagc aaagccctga gtcagcgcac     60
gatcactgtc ggggtgtacg aagcggccaa gctgctcaac gt                       102

<210> SEQ ID NO 72
<211> LENGTH: 138
<212> TYPE: DNA
<213> ORGANISM: Homo sapiens

<400> SEQUENCE: 72
aggctcactt tgtctctgc tttccccggg aagatactcg ccaattccac ggcagtgatc      60
aacaggctga gaagctaagc aaagctgcag gcagcctcca gggactgggg agaccgggag    120
ttcagaacct gccaagga                                                  138

<210> SEQ ID NO 73
<211> LENGTH: 1970
<212> TYPE: DNA
<213> ORGANISM: Homo sapiens

<400> SEQUENCE: 73
gcacgaaggg aactgagacg gctgaaggag gaggctagga ataaacatgc tattgcagtt     60
atttgggctt actggcttgg atctaaggta cttgatgcac atatcccaac actccatcct    120
ggaattctgc aataatcagt ccttacctct agcctattag gggatgaatg actacaatta    180
atagtggctc acactggtgc atgtcctagc cgccagattt aacacacctg gaaacattag    240
ttcagtagta tgcataggaa gcttaggcat gcataggtca ataaaactaa ttgcttacta    300
aaaaggcact agtatcattg ctctttaaaa caaaacaaaa caaaacaact cttaaataac    360
atgcatgttt aggttccccc ccgccccat tgatgaatgc tagcagtttt ttagaggttt     420
tctggagggg ttgcgcatgt tgggaatgtt caagtttggg cttcagtcgg tcttctgcaa    480
catgttgaca atggaaatgc ctctaacata tgtcttaaaa atattaattt atgaatgaaa    540
ttttttttta ggctcagtgt ggcagctatt gattattata agcaaaatat tacatgtgca    600 agaattatc atctgtgatt taacagaaaa ctatgttcat gcacagctag ctatgattgc    660
cactgaagaa tcccaggaat ttcagcatca gctgtttgtt ttcagaaaca aaggcctcct    720
gaaatactct cactaatccc caggcatagt cgtgggctct gtgaacattt cacataccccc   780 aagggacaag attttagat gttttttgtta cttagaaaat caaagtcatc tttgctaaaa    840
atgtgtattc cagttagaaa cacaaacatc aacagagtcc tgtgttttga agtccacctt    900
gtcaatgttg taagcctatc ttatgagaaa atgagaaaag tcaacatctg cctgcataaa    960
gagctaattt gccaaaaact aaccagagtt gttcatctgt gcttttcctg aaaatctgtg   1020
aagaacaaac ttgttcctct agtcaactga gggaaatgtc atagcagaag caaaaggact   1080
```

```
cttaggtggg tcttgctaag atttctccat ccagtgagtt catttcccag tctcagtact    1140
ataatatctt gaacaatcag tgcctatttg tatcctttag aatagcttgc ctaagattat    1200
tttttcccta agagtaattt ttaaacctat aagtttaacc tataattgct tcagtcttcc    1260
tgtatatttt acttttgcga ccttagctaa aattgaattt ttacacgtgc cagttttcat    1320
tttttgactg gaaggaattt ttgagttttg ttagttttgg ttttttgtttg cacttcagag    1380 aaataaactt ttttcctccc agttttctaa gtgattgttc acaagagttg tctttttatc    1440
catccaaagg gatgaactca ggagtgcata gcttcttcag cccaatgtgc tgtcagcaaa    1500
ggggagtcta atgacatcat tagggctgtt actcagagtt tgaaggcttt gatatgggag    1560
tgaaagagtg tggagaaggc agcgaacaga gagagagaac aggagaaaaa aggaaaggaa    1620
tggaagtgag gggtgggaaa tgattacctt gggaaccaca cagattgtcc ttctctggaa    1680
cagaatctca gtgcactgaa aatataagcg ctgcaccagc ctgacaccaa ttctttgggt    1740
ttaaattgtt atgcactgtt cctctgtcat tctgaaatcc ttattcataa attggctctt    1800
ctgtttggtg ggatatcttt ttctggtcat ttgtgctgtc tgcattgggc tgtctctttt    1860
atttactatc taaaacattc taggctcgaa gggaattgaa acgcttgaag gaggaggcta    1920
ggcgtaagca tgcagttgct gtcatttggg cttactggct tggactgaag               1970

<210> SEQ ID NO 74
<211> LENGTH: 342
<212> TYPE: DNA
<213> ORGANISM: Homo sapiens

<400> SEQUENCE: 74
gtgttattgc ttccaggtca ggggtcacca cattgcaaaa cttgatcctc tcggaattag      60
ttgtgtaaat tttgatgatg ctccagtaac tgtttcttca aacgtgggtg agaattaagc     120
tgtaaatgct aattttaatg taatttttact ttttttttac cccttccctc tttttttttc    180
ttctgtcctt ttgtgtgtgt ccttccctct catcgttggc cactcataga tacgagggca    240
ccatgtagca cagctggacc ccctggggat tttggatgct gatctggact cctccgtgcc    300
cgctgacatt atctcatcca cagacaaact tggtgagggt ct                        342

<210> SEQ ID NO 75
<211> LENGTH: 699
<212> TYPE: DNA
<213> ORGANISM: Homo sapiens

<400> SEQUENCE: 75 aaagggtaa attgtaaaca cactttcaga accactttt gtcatttttt tttttcaga         60 aagtacctat aaaaagtaaa agaccacatt ttagggggag aaatataaaa ttatggtgaa    120
aggccacgct gtgaaaagta cttggtttac agtacctgcg gtgttctcca ctggggcctg    180
tccagagagg cagatgacac tcacctcatc aactggcaat gaacagcagc tgaaaagggt    240
ggctgctgga ctggggactg ttcttactcc taagtgaaac cctaccttcc tgatactcat    300
ggagaacact gcagttacga acagaccaaa acaggagct gcaaatgcag aactcactgg    360
gcaaaaactg acagatgata ccaaagtcgt gaaagtatct catctcaaaa aagataacta    420
caatctcaaa ctttcaaaaa atgcagatct tgctcagaat aaatcgtaac aatctcaaag    480
tgcatttgga tgcagaacgt atatttacct atataagctc tttcttgttc tcgagtaagt    540
ccagggggaa taactgtagg cattcctgga atcactgtct tctgttccat tgtgtcttgg    600
```

```
ttccagcggc tcctcttccg cttcttactt gggaagtcta aaaggcagag acaaaatcca    660
tccgatgtaa atacaagtag ttatcaacag acagctaag                           699

<210> SEQ ID NO 76
<211> LENGTH: 2390
<212> TYPE: DNA
<213> ORGANISM: Homo sapiens

<400> SEQUENCE: 76
gggtaagatt ctttctcagt taattttat taatactatt atttgtgcag caaatagcaa     60
aaaagaaacc taacagtctc tcaatcacaa ctgtatttat attctttcac aaccattaaa   120
acaggagaca ggtttacata cttcttcttt agtcaagtgt tgttctcgca ttacatccat   180
gtaagtccta gcattcattt taggatcagg ggttttccct cctgcagaaa agaacagcaa   240
caggaaaaag agtacaataa ataaaaaata agcaggttca actgatttat ctgccctgct   300
ctaaatatta tgttattcca taatcattta aattatttt tgatggaaaa ctttaataat    360
tatacatctt acttttatt gagtttgctg atcaatttaa cctgtttgaa cacaaacatc    420
tacagcagtt taaacaaat attttaatgc atataaaaac aaaatgacag cacagtttag    480
agtcttcaga agtgatgggt tcctggggttg ctaatccgga atacgtacac tttcgtgcct  540
ttgtctccat cagcagttct gacttcaagc agcagaatag aagcctagaa aattatctct   600
ttaccattag taacactttg gaaagatatt tatattcaaa acattacctg ttgcaagctg   660
ttaaaatcct gactacaaat aactatgact agataagttc ttcatacagt gttctaaaac   720
aattgtagtt tagaaaatct gattttaaaa atatacctat aatcttattc tgatgtcacg   780
ttactaaaaa gggcttcatg ctttaagttt tgttgaccca gaaaacatat ttttatttct   840
tagaaagcat aaattaaaac tggaaacata ttactttaaa tatattactt ctaccagtta   900
ttatgatgca cacagaagca acgtggtgta caaagagatg tgtcagtctc ttggttaaag   960
tttcagtatt tgcttttcaa acttcaaaat atcttacaga agcccaaaca gtatataaca  1020
agattcacag aggcacacta tgctttagaa atgtggtaac tagctataca agtagtatag  1080
catcacaatt taggaaaaaa taataaaaatt ctaagacatt tcctatgctg aagatcatgc  1140
ccaattggta gtgtcattct ttctgacact agctctgata agacttcctt tggaatactt  1200
tttcaccata atctagagag gatgtgttga actgcacccct taagaatgca gacaggactg  1260
gcatatagca gtactgctgt aggaaagaaa ttaaggacag ttagtatggg cctgtgaatt  1320
ctggcataca tgtttaaatc aattacaatt atgcaagtaa aaaagaata tccctactaa   1380 ttcatgcagg ctgaaaagtc tagtatgtaa acctgcagca gaatctaatt ttaagaaaca   1440
ggcacctaat tttgattgtg aaactcactc acctgaggaa agcttccatc aggctcacta   1500
tgccccttgt gctgacttgc acactaaaat tagcaaaaca gactccaact attaaaaata   1560
tcaaactctt cgtatacata cttttgtttt aactttaagt atgcttagag caaagtaggt   1620
gcctttacta agctatattt agagcactat gggggagct ctagtgtgag aaacagtttc    1680
tcaagggtaa caatcctaaa atctaggat ttggaatgaa aactttcaat aatttgaaag    1740
tattttgagc agaaaatac atttgatcca agtatagaaa gcgtacccaa aacaaaagta   1800
aaagtaaaac ctttaacccct ttgcgtttct atggcattgg ctcatttttt tcttgtcctt  1860
ctacctggaa agaaaacttg cattataaag atgaagaata tggcatctgt gacttcaacc   1920
acatctatac aaatctatag taggggggat ttttaaaaag aaaagcaaat tcagaagcat   1980
gccaaaaaaa atcaagggc taaagacaac ttaatacaaa taaatttctg aatacttata    2040
```

| | |
|---|---|
| gaaaagtggg aaagaattac catctgcaaa aggatcaaga cgctctgggg aaattatcat | 2100 |
| ggtccgccta tgcttttttgt attcatcttc ccggtctgca atctttggag gtctgtgctc | 2160 |
| agcaaatgga tcatactgaa aagaggtatg tctcacttaa tatccacttt attaaaataa | 2220 |
| caaaacagaa tatcataaac aaaaatcaga acaccataaa gcacaaatgt ttaatacatg | 2280 |
| cctactaata ttctgtaccg tttcacagat aaatgttaaa tataaaaaaa taaggcacat | 2340 |
| ggaaacaagg taatatacat atccacattt ccatagttca atgcttcatt | 2390 |

<210> SEQ ID NO 77
<211> LENGTH: 4439
<212> TYPE: DNA
<213> ORGANISM: Homo sapiens

<400> SEQUENCE: 77

| | |
|---|---|
| atccggtctc gtacatggac atgggcctac tgccccgggc agacggacgt ctctttaagg | 60 |
| aagagtggtt ggaagtgtct gtgtactcag aaccagtttg cacctgatat acattggttg | 120 |
| tggcctgttt cctgaggttc gaattttcac tctggagtgt ttgaagctga agaaatgtt | 180 |
| tggcagtggg actgtgtttt tttacagcaa gcagaaaaag caaacaccaa gtaaatgaat | 240 |
| acaactacca gttttaaaca ataaggacag taacagctag ccgggctgaa agtaaaaagc | 300 |
| caatacaaac aaggaccctt tcttctggat tgggtgaaac acaatcaact cccttcatca | 360 |
| cgtaagcaaa ttaaatagct tcatttctga atgtggaaaa gttgtggttt ggacttcctc | 420 |
| aaaacaaaat gtctaaccac tttaaaattt gtcatggtgg ggctgggaaa tgtttgcagg | 480 |
| caagctgtac actggattat tactaaggct gtttcaagca agagttcgag atcattaaaa | 540 |
| catcatttag gtaacttgct tttcaaatga gccctgagca atttgtaaag gccaaaaatg | 600 |
| acagcagaca ccatggaagc agcacaaaga tgactagggt tgctttgcaa gcaagaaag | 660 |
| acagaagttc agcttgtgaa aaatcagatc gcctattgct ttccaaaaag ccaacaagaa | 720 |
| aaattatgat caacaagttt ttattacata atactcttga tattccaaac aattcagcac | 780 |
| tttgtaaaaa aaaaaagaaa aaagagaaaa ccggatcatg gtaagtttgc tatattaaca | 840 |
| tatcacgaag aaaactggaa acctattgat ctatggaatt gacatcttcg catggatgct | 900 |
| ccacgcagca cgcttgcttc cgtctggtga gtgatcatct ttcggccagg gctggaatat | 960 |
| ttggcctttc tctcctttgg ctttgtcacc caaaaaacac gacctcagtg gtgtcagctt | 1020 |
| tgaacatgct aatctgcctg gcaccacccc atttttagaga ctgtcacttg gaggccctga | 1080 |
| atgctccttc cattcctcac atgcaggctg ctccatggtg ctggatggat tagagttaag | 1140 |
| gggtcagcag ggaatcgtgt tactctttgg catctggcat tttaaacacc attcaccacg | 1200 |
| tccattctgc gcagggtcct tcccttctgg tgcgccttca tcttccatgg acattctata | 1260 |
| agctgggtgt ggtgtgagtt cagctgtcta ctctttgaca gagattgtaa aatctgacca | 1320 |
| aattccccac cagtgccaag gtttaagtcc acaagcaact gtttgcacca gaagatcatt | 1380 |
| acttttcag tagcaaaccc attcaatgtt aggagttact ttcaattttt atttagaaag | 1440 |
| caccaatctg tgaaaaatac accaatagta gttgctcctc ttcattaatt agcatctttt | 1500 |
| ccaagcaact gttaaatgtg aaagatcaga tacaaatcat gctactttgt caactttatg | 1560 |
| tatattaaaa actttacccca actttgaaat ataatcaata catctttgct aaataaacaa | 1620 |
| attccatata cttatatatta atcatgccaa actgctgtga aagtgtgact tactgcctct | 1680 |
| tccacaaaaa gaccactcat tctgtttctc tgaagagcaa gccattacag aatgatagaa | 1740 |

-continued

```
tgcttttata tcacaaaggc tggcagggta tagctcatat ctgcaattcc ctttccaggg     1800
aaagaacagc tgcaaagcag ctgacaaagc agccctgaac atttctacat tccaggatac     1860
agacaggcat gaagtgcctg ttgaaactat tcattagaga acccagggcc tagagtgaaa     1920
tggtcaaggt tcaaggactg aggtgtgtaa ctgacacagg tccctcaatg gggcactggt     1980
gcatgtgatc acgtgtttgt ctgtataaaa agcctctgtg gcagttattt agttaaggcc     2040
ttgaaatctg aaactttatc ctaacacttt tcatgcctgg attttgtctg aatgtgttct     2100
catgagcaca agttcttggt ttcaattttt aaaaatgtta gtactctgta tttagagaga     2160
tgtcttcaca taaattttaa tgacgtttat cttaataaga accaggctac acttttttat     2220
ttggaaggag tataagggaa aataaaaagt tatagacaat tcaatagttt cagaaatcaa     2280
aagcacttct aagaattgat gagataatca ataagcaaaa gcaataatt tcactttgca      2340 tttctcaaag aagctcaaga catttgcttt cagagataat gaggctctct ctggtgattt     2400
ccaaaaatac taaagaagc attgttagat tttaaaaggt gatgtgcagc agattgattt      2460
acagtggcaa aatcagcatg tttcagaaat agtcacctgg tcaaaattat tagtccaatt     2520
aatggaacaa actataatcc actaaataaa atatattcca aagaaggcaa agaaaataca     2580
ggtcctgtat gttatgacaa agggctctc ggtctgtctc gtttacagct gcacggcagc      2640
cctagacagg gctgggagac acagaacaag tgtctgttcg tttaaggcta gctgatctta     2700
agcattcttc attccctgct actataggca ttagagccat ttatttcaaa aagtctcaaa     2760
aatgctctag aagtcaacat caaaagaatc ctagaccaaa ccccaggcaa aagtgcacag     2820
caatttcctt ccctagtaaa cagagggggca tgggccccct tttagttctt ccaccttcct    2880
ttaggaagca gcactgaaaa gagtccaggc acacatggag tgtgccacgt cctcaggtct     2940
tgaaaatgat ttgaaaacct tacttctcaa atgacagcct aaagacatag attatatatt     3000
tcattttgtt tctggttaag taaagtgtcc aaatctcatt ttagagctga atgatgagtg     3060
atacccacaa agtcatgggc aaaatttgca attttcgaa ttcccttatt tagccatctc      3120
ataaggagtt gcatacacaa tcccctcct actaagggta ttccttgcta ccatcaacca      3180
cactcctttt agggattaat atattcacac ggttctgatt ctctcaaaag gtaatgaatg     3240
agaaaatgct gagcaaatga gattgttttt taccagtgtg cagctcttcc tagtacaaat     3300
gaaatgtttt ttcttatttt ttgagcaccct actctgtggc aggccctcct gtaggctctg    3360
gggataatac aagttagtag taaaaactgg tgagcaataa ggtggggatg tgggataggg     3420
ctgccagggt gggagcaggg tttgaatgct gataaacatg cccctgccca gggctctcat     3480
tggctctgtc tccatggtgt gatcatcctt ccctagcaat gggaagaatc acatccatgg     3540
agccccatcc aggtttccag gaagcacaga atagtccaag ggttattcta atgggcacaa     3600
atgcttaaat agatgttagg tttctcctac ctggggaact tactctggat atatttcatt     3660
ttaaatatcc aaatacatcc tgcttcaaaa agacaacttg gcccaaagat ttctaaggct     3720
gttacaataa ctgtttttct ttcctcggac cacatcacag tgcctgagat tcttccttgt     3780
actatgggat taaagcgtca accgtcctgg catttattaa catgttacct ttttctgcat     3840
aattctcagc tcgtcactca agttgttatt caccttcatt agctgctgta tcttggcctc     3900
agaagccact agagcgtttt tgacctccat aaattcctgt acagtgactg gtccatctga    3960
taaatctgaa tctaggctct aaaaataaat tgggaaaacg ttcacaatct gagatgacga     4020
gaacattaaa gactaacagc tcaagaattt caaattctga ccaagccagc tgaattgcaa     4080
agttagtcaa accaaatcaa ggcctctgag agtaatgcaa aactaaaaca taaaagtagg     4140
```

```
gtcactatac tatttaaaaa atttgaaagt cagtatttc taatagaaca ggcagtgagg   4200
ctacacatct atgctgacaa tgactgtcta aggaggtctg tcctgtcttg taagcctttc   4260
tctcgttcac tcttgttttg tttttattca ttctttcatt aattcattca ttccaacatt   4320
ttcattgaac attaggcagt gttctaggtg cttgggatat attagaaaag agacaaagat   4380
tcctgcttcc atggtgttta tattccaaca gcatgagaga gtatatatat tgcatgatt    4439
```

<210> SEQ ID NO 78
<211> LENGTH: 5466
<212> TYPE: DNA
<213> ORGANISM: Homo sapiens

<400> SEQUENCE: 78

```
tatagggttt ttaattgatt ttttttcccc attacagtgt tcacaataat gtttcgaccc     60
aaagtaatgg ctcccaacag gtaagacaat actaagcttc taaaacactg gatcacccgt    120
taattatggt aacagtagta gtattgattg gattttcata gtggtgtatg taaccctgca    180
caaattatgt gcattttctt ttcctttcc cttaagtggt tcagtaataa cttccggtta     240
ttttattctc taagattttg taaaggaaac cggtgctcta taaaacattt tatgtctctg    300
tgaatccaag aacataattt aactgactac taatatttca ttcattaact atctctaagg    360
tgtatataaa attcaagcat ttgtatacat tttaattgtt ggctttgtaa atagtactcc    420
attttagtat ttgttggtga agagatctgt tatcgaggca aaatagataa ttttttataat   480 ttttgtccaa aggcttgggg gatgagatct gctctgcctg tgagtccttc catttcctct    540
gctcctgtgc cagtggagat agagaatctt ccacagagtc ctggaacaga ccagcatgac    600
aggaaatggt ttgttaattc cttaaactaa aataaaatat tgcctagtta attgtatttg    660
gaattccaag tcataatctt aaagtacttt aaatatgatt gaaagcaaat tattcatatt    720
tgtgagctgg aaagcttatt attaaataat catattgaga tggggaaaat aaggatgttg    780
gtgataaagg gagtgcagtt gtctaaatga agaccatcag acagctgtcc ttacttatta    840
tttatttgaa acaaaacgtt aatacattta aaataaatct gcccttatta gcttgatgtg    900
gtagtggtgg atgattctct gctgaaaaag acagtagaat attttcccag gtccgtaagg    960
aaagtatatc cactacgtgt tattccacac aacatgatgc tactttgaat gtgttttcct   1020
cattaaagac gaagggtaaa gtcagaagca aaacatgatt aaaatctgat aaagcatgag   1080
ataccctaag gagactgaga gagaatctga tgacaggaaa aagatacttt aattatttag   1140
acttccaggt tctttttta gattaatagt aaatatacaa atatggatac tttgtgtctt    1200
attggagtta atcacttgag tttatccttt cccaaataaa tatatgtggc ttggtggggg   1260
ctccttgggg attatttgat tcagtggtca tgttgggtgt atcacctgtt caagttattt   1320
gtctgtttgt gaaatgaatt ttgataattc ataggatttt tctctttttc tcttgctctt   1380
agtttgttta gtacctgaaa tctaatgcat ttctgtggtg atctcaaggt tttggtcagc   1440
tttctgtgca gccagttctt ccttcatggt ggtggctcaa cagtggttgg tgattgtttt   1500
cagtctttgc tatgtaatta ttttttcactg ttatttggc ttaactaact gcagggtgcc   1560
ttgctcttga tacttgggtg tatttttatt tcagttccaa ataacttgtg attagtttat   1620
aagattgagt tccccttctcc cctggcccca ttttctcctt tttatttct ttctacatgg    1680 gtatgtggtg gtgatacttt gtgtatattt gtgtgcatct ggggacacac ttaaaagtgt   1740
aaagagtgag gcttataaat gtcaaattta tttttgaaag tcatttttag aaagtttctt   1800
```

```
caatttctta tggaaaacac agctcctgta agcagttatg ttttatctca ttgatgttac    1860
caccaagttc tgtttgcaag gaaaaatagt attgagactt cagctataaa ggaagtgtct    1920
ttgcctatta tgttaatatg gagtgagggt ctgattagtt gggatactat attacgacac    1980
tgaatctttg agttttcca tatgaatagg tacatattta aacctgtttg atttgatttg     2040
ttaggtacta cttggtttct tgatgcatc ctttagaaag agcattgaat ttattaaatt     2100
ttaaggaaaa tgaaaattt ggagctgtgt gttctccttt ctttatgtgg ttgtgctgag     2160
acctcctttg ctgaaataga gtaaagtgat gctctttata acataataag cctcagtgta    2220
ggtcaacaag ggcatggaac tgaatataga gctggcatgt tttggagata atggactctc    2280
ccgccttaat ttcatatgtg ttctgcattt cattcttttt tctgcatgct ttgattcttg    2340
ttaatgcttt caaagaata taaagcagtc ctcctttaga aagtgataaa tggttaaaat     2400
ttggaaatgc ttcctatgtt tgaacaattg ggcagaataa tggaccattc tattgcttgc    2460
aggtaacttt caaccaattt aatctacacc tactccctgt tcaagtcttc agcatttttt    2520
tgctggtatc ttttaaatga caccattatt agagcaaatg atttggcata tcagtggctt    2580
agaataatca agtatttaaa atttcacttt tgagaaaca attcatgtat tgtaaaccca    2640
taaatcattt gtaagcaaca acagaaacaa aactgaatag tgtttagaaa accttgcatt    2700
ggtaggggag aacataaacc taatttagtt ttctaaattt ttagagacca taacttgagg    2760
gttgtgattt ttgtgagcca ggtctgatga acaaattgta tttcagttaa agaaagatg    2820 attttgttat taaaaagcc ttccaatttt gttttgaaaa attattttag ttaatttatt     2880 ttcagttttcc ctaagggata aaggtgaaga ttaatgtttt ggttgagtta gaaagataac   2940
acttattaaa aatgtatttt tgcacatatt ttatatttgg ggtggcattt tcctttgtag    3000
ttattttaaa tatatgctgc cctttctgcc atgtcacaag actttgattt gctttctttc    3060
tactggagga ctctgatcag ttctgaccaa gaactgcatg tatgcatgtt tcactcttag    3120
aattctatag gccttttcta tagcactgtg ataaaaggtg cctaatatgc ttactaaact    3180
acttcttgga gagggtgtat catctcatca cattatctgt acctgttgaa tttcattttg    3240
aggtcttgtg aactttgatt atataaggag cgatgattct ctattgctaa tgggaacat    3300 tgatgtaaaa ttacatggcc tctgaaggta gatttttat ttttagtgct ctttctgaat    3360
tttgtttcct gcatttcagt tctgtgaaat cccataattt gaggaagaat tttcacagtt   3420
ttccttttcc atatatgctt ttgtccttat gtagagttct tttttcaaat atttgaagtt    3480
aagtagatta tgaatatttt tttcttctga ttaaaacccc taacaacatt tctgctttta    3540
atattagtaa caacatcagg gacagataca gagtgtcttg ctttctgaga aatttcttct    3600
ttaattcact tagctgactc agattactta catgtatttc catattggta tttttcatta   3660
catgtaactt tgtggatttc ccccactttg ttattcttga atgttatcat tgcatggagt   3720
agatgctggt aactactcat agcagcagtg catgctagtc acattacctt tccccttttat   3780 tgtctcttac acatccattt tctcctattc ctattgacta actgtgctcc cctcccactc    3840
cccaaccatc caggctctct gctgccagcg actgctgtca acgtggtgga aaccagtgga    3900
acacaagggc cttgccccca ccccagaccg cacatagaaa ctacactgac tttgttcatg    3960
agcacaatgt gaagaatgca ggaatccgtc atgatgttca ttttcctggc catacagcca    4020
tgactgagat atgagtgttg agcctcttag gctttgggac tctttgtcat gcaagttgat    4080
ggtatacatt atcggtgtt tataaaggat taatcacatt aggagtattt gggagaattt     4140
acagtgagtc actagttgtt cagtgctgtt tgtaattgaa ttcttccatg aaagggacaa    4200
```

```
ggaatcaagg aagccatata gcatcaatga taatgacaaa tgtttgtgtt gaaaagagtg    4260
tgtataccat tgtggttttg gaagagtttt cagaccttag tatgttcaca catcaccaga    4320
ctgtatctca ggagaaggtt tgtgtttgtg aacaaggtgc ccattattcc cccaccacat    4380
gccatccaaa gagatcgagg ttaaaagaat cagacacact aaaaacacag tggaagcatg    4440
tctaggcata atatatcagc cttttgagat atttattaaa aacttgttct tatacactat    4500
tttaatatgt ctaaagtgac atataccctta atttaagtgc ctaagatttt aattaatata    4560 attttaatt acaaacactt ttacttttta ataaacacga atattttaac ttaccaaaag     4620
atttagagat cacattaata atgtggctca tgtatagaga aatctgaatg gttagttttg    4680
aatggttaac tgattaacat tcagttatca taacagttaa ccagtggtta actgaatggt    4740
tacattacta ctgaatggtt ctataaaatg aaaaacatat ttactttgtc ttttcatttg    4800
actggctttt ctctttcatc tcatacacct gacagattac ccaggtttgc aacagtctca    4860
taatctgatc ctgtataacc tttaaaataa aattctgaag ccaaaaccat atgattttta    4920
gattgtatta ctattttga tccttttaa actttagaat ttcaagctcc ttggtttaat      4980
taatagaagt gaattagctg gaaaaagtcc atttctgata ggaaaacatg ttaagggaag    5040
catttcttct gtcttttttt agttttcttt tatattttag aaaaattttc aaattttttaa    5100 actatgtaca tagaaatttta tagatatttt atatttcgaa gagtttataa tgcttcaaga   5160
taatgaagct tcattataaa cagcttaact catttaatgc atcctgctca catagaggtt    5220
ggttttatat ctcaaatcct tcctgccaga caaagattaa ggtttcagag ggcttaatac    5280
tggactattg gtttaatact gaatggttgg ttgcagtttg tccatagaag acctaaataa    5340
gcagaactga ctaatattta aagaatgaaa tttgtaggca ggtttcaatc tgagtttagt    5400
ataattatgt gtaagaggat ggccactcaa agtatttagc acatcctcta aatataaata    5460
gatctg                                                              5466

<210> SEQ ID NO 79
<211> LENGTH: 5561
<212> TYPE: DNA
<213> ORGANISM: Homo sapiens

<400> SEQUENCE: 79
gaacagaccg tattaatagc tttcctaagt aggttgaaat cttccgtttt ctaaatgata      60
tcagtaggag acgatgggtg tatttctttt ctgggccagg tagctggcag ctgctagagc    120
tcgctgaggg tctgttggga agggtttggt gagatgcgtt cacaagtctc cccagccagg    180
tagtgggctc gatggtagga gcacaggaca ggaccaggga tcatcctgca tccctcactc    240
tgctcgcaac gcagagtcag agacacacgt ccaagagcct catcatgtaa caggaactca    300
ggttttaaaa gctaagtgca tctccctaat ctagtaagaa gtagcacatc agtcaaaaaa    360
atgaccaaat ttaggccggg cgcggtggct cacgcctgta atcccagctc tttgggaggc    420
cgaggcgggc ggatcacgag gtcaggagat cgagaccatc ctggctaaca cggtgaaacc    480
acgtctctac tgaaaataca aaaaaaaaaa aattaaccg ggtggggtgg tgggcgcctg     540
tagtcccagc tactcgggag gctgaggcag gagaatggt tgaacccagg aggcggagct     600
tgcacatcac gccaccgcac tccagcctgg gcgacagagc gagactccgt ctcaagacaa    660 aaaaagaaa aatgaccaaa tttaaaagat atccttaggg ccttggctga acacaggatc    720
tctttaaaaa gaaaaaaaag ataccatttt aggctaagtg cgttaaaatt cctacagtca     780
```

```
gatttacaat attaaagaga tggaaatcac ataccaaggg acaaaatta actttagaaa       840
aaaaaaataa aacatgaggg ctgtggtgga caggaaacag ctgttggatt tgagacagct      900
agcatggagt taaaaggcct gatctttcat attttgctag tagaattcat aagtaaatgg      960
ttctcctttc tgctggtcag atcatgatca gaagcatctt cctgttcttg accgcacct      1020
atgtgctgca gaactccacg ctgccctcca tctggtgagt gtcctcacag cgcagagctg     1080
cgtcttccct gcagctgatg cttttcgtcc cgtttgtgtc ttccgcaggc taagatggta     1140
aagtgtgtgt gattacttgt gccttccttt cttcagccaa atcattaac gtgaacgtag      1200
gagtccaggt gggtcttagc cttgaaacac caggtgtcta gccagcagca aggagtggag     1260
caggaagctc ggacaggcgg ctgactttgg tcatgagggt gaagacagag ggtcttggtt     1320
tctctctgac gactggaggt tgagcctgga gcggctcttt ccagcgctgc agttgaaact     1380
cggagaaaga ctgcctgctg cccgtggggt cgcagccctg aggctgtgcg tcccctgtgg    1440
aatggcttgc tcagcctccc ggcctcctga gcacatagca ctcatcgtcc gtcatctttc    1500
ggggactgta tacaccaggg gttctgggc cttttcctcag cagcgttcgc ggccacggac    1560
cccacatgtc ctctgctgac ccctgtgtgt cctctgtggc cacccatgg cgctgaatcc    1620
tgccgcctcc tgcaagccga cttttggacaa aagctgtgtc cggtctcacc gtctgatttg   1680
tcttgttctc tgttaatgta gtgtttcatt cttctcacat tcatacataa aagtgatgtc    1740
gtgccttctc atgagcttta aacccaagtt cttttaaaatg tgcctgcttt tcctacccca   1800
cccactgggc acgctgaccc aaggcaatgt gatttctgct ttcgccatgt agagattgct    1860
cttgtctgag atgtcggtga cctgccagtt accaaatcca gcaagcattt ttgtccttat   1920
tttatacaac atctatacaa ttttggacac cctgtccttg ttgaagctcc cattaatgcc    1980
atttgccctt ctaacttcct catggaactc ccaaacatct cctagtaggc atccatgtgg   2040
tctacgagaa ggcaaacgct gcacagaaaa gacagcctgt gttccaggaa agaatggaga   2100
tgataaaagt gatcatagca gattatttag catttgctct gtgcaaggga ctgtttccta   2160
ctaatgtatt taatccctag agcagctctg tggcgtggcc attgtcactc ctattttata   2220
caaactaagg cacataagtt aaaataactt gccctacctc agttgtctgg cccatagtct    2280
aaatgcttt caaaaattat tattattatt attattattt ttagagacag ggtctcactc    2340
tgttacccag gctggagtgc agtggcacaa tcataactca ctgcagcctc aaactcctgg   2400
gctcaagtga tcttcctgcg ttggcctccc ctgtagctgg gactataggc acgcaccacc   2460
acattcgact aacttctaaa aattttttgt agtgccagga tcttgctatg ttgcccaggc   2520
tggtctcgaa ccctggcct caagcgatcc tcccacctca gcctcccaaa gtgctggaat   2580
tacaggtgtg aaccaccatg cccaacacta aactcttaat ttataaacat agtttatacc   2640
ataactgtca tacaaactat aaacattgtt tataaaatag aataaatgat accacctcca   2700
gtctaccaca agtggctaaa aacctgaacg tgagcatcat tacaagaaga atcctggttg   2760
aggtgtgtgt gggcaatgca tggtgaggag atactttgtc catctctggg atggggagga   2820
gggctgaggg tgaaccttgg cctgtgcttt gaagaatgag caaaggtggt caggcagcta   2880
agaaagaaag agtagaagga agcagtaagt tcaaagccga gtatctcctg ctagtgatgg   2940
ctaggacggc agcatgacca gaagaagcct gtgtggggag tgggaggtgg ggagggatag   3000
agctgatgag ggccctgaag ggttttttcag ctgaggttga tgttttaaag agaagatccc   3060
agtggcaggg tagagagtca cacaagtgga gacctaagcc ttcctaagca ctggctacct   3120
gcctggcact gccccaaggg cttcagaggc aggaactaat aacatttgat ccccatttta   3180
```

```
acagttcagg aaggaaaggc acagagacat taagcttctc acccagggtc acacagctag    3240
caagtagtag ggccaggatt caaacccagg cagctgcctc gagcccacaa gtctggccac    3300
tgcaccttcc tgctccaact gtggtgaagt gcacagaaga cctggtgtgc agcacacgcg    3360
ggagcaacag gagaggccca tggtgatgtg ggcagtcaag ggaggtgcac gtctccacca    3420
ttgaggtggc tcccagggcc ctctgcacac ctgtgtggca cccaccactg cggctgctgc    3480
caccactgcc accataatat tattaataat actaccacca ccacccgcct accactgtta    3540
ctactgccac caccaccacc accattactg ctgccaccac tacccgccca ccaccattac    3600
tgtcaccact acccgcccac caccattact gtcaccacta cccgcccacc accattactg    3660
tcaccactac ccgcccacca ccattactgc tgccaccact acccgcccac caccattact    3720
gctgccacca ctaccgccc accaccatta ctgctgccac cactacccgc ccaccaccat     3780
tactgctgcc accactaccc gcccaccact attactgctg ccaccactac ccgcccacca    3840 ctattactg tgctgccacc accagtatta ctgtcaccgc caccaccgct attactactg     3900
ccaccaccac ctgtccacca ctatattact gctgccacca ccaccactat tactattact    3960
gccaccacca gcaccactcc tgccctgatg tgccaattcc ggatttctgg ctggagccca    4020
gcatctgtat ttttggcccc tccttaatgg cgtacttggc cactggggac agtaggagtg    4080
ttgaagcaaa gcacagagcc cacaagatgg gttttgtgga cagccactgg cagctgaacc    4140
atcttcctaa cattcctcag gccatgagct gaggactgcg atgaactctg aaagctgtgc    4200
atcaccttct cttctcaggg gaaagcagca aacatttggt aggagagctc ccagggcttg    4260
gagaagggaa gctgctggga cgtgctcagc agaggacact gggaagagag tgtaccctga    4320
gggctgttgg agacggtggc gggagggca ggtggggcag gcagggtcgt ggtgcccaac     4380
tgcctgagtg tctcccgtcg ctcagcagga aggtggcgag gaccccgggc ttctgccagc    4440
agcttgtgtg ataccagttt tactgtcagt ggcatgcatg acctagcagc gtctccagga    4500
acgtggagca gctctgttta aggaaggaaa tacaaggcgc gctagactgg ctgagaaaca    4560
gaagttttta aaaggaattc ttggcaccta gatgtagaga attagcaact tcacattttt    4620
gggatgatat tgaatagcat agctggagat tcacccataa cttctaaaaa gcgaaactaa    4680
aatgtagtcc tgtttcttac tgtctataca gggatatggg attagaactg tttagaaccc    4740
atattattag tgataaaatg gttcagagta aaaccattga tggaatccta ctgctgatcg    4800
agcgcgagag gagcggcgag gccgtggacc ggagcctgtt gcggagcctc ctgggcatgc    4860
tgtctgacct gcaggtgagt gctgcctgtg cggaagatac ctgggtacct gcccagctac    4920
ttgcaccaga ataaatggtt gtaccaaaga tgttaaacaa tgaaatcata aaggcatttg    4980
ttgaagatag gagagtcttt aaaatcccta gaagggaat agcgctcaag ctaacaccac      5040
accaggtgcc acaaaagaga agatagatca atatcactac ataaaatgca cggatagatc    5100
aatatcacta cataaaatgc acgttttttca tggaaaatat aaacagagac aaagccagat    5160
gacacgctgg gggaaaatat tagcaacaca cacaaaagac aaagggcgaa gttctttaga    5220
gcaataggac cccaaggcac tataggaaga aacagagga gggcctgccc ggccgttttg     5280
ggaaggacag tgcagccggc cggctgggtg gccacaggcg cctccaagtt caggtcatgg    5340
cagcctgccc cgtcagaaac tgggatgtgt tagcacttgt gaagatagtt tcctttactg    5400
aaattggtca gtaactctgc ttgtttctta ggtgtataaa gattcatttg aactgaaatt    5460
tttggaagag actaattgct tatatgctgc cgaaggccaa aggttaatgc aggaaagaga    5520
```

```
ggtgagatga tgggatgttt ccgaatcccc tggcttcgtt t                  5561

<210> SEQ ID NO 80
<211> LENGTH: 480
<212> TYPE: DNA
<213> ORGANISM: Homo sapiens

<400> SEQUENCE: 80
gtgagagctt gcttagttcc tgatattatt gttctcttcc ccattcccac ctcagtccct    60
aaagaacatc ctgattcccc cagtcttcaa gcacatgaat tcagaatgaa aggtttgcca   120
tggctaagga atgtgactct ttgaaaacca tgttagcatc tgaggaactt ttttaaactt   180
tgttttaggg acttttttt ccttaggtaa gtaatgattt ataaactcct ttttttttt    240 gactatagtc ggttgcatgg ttactttaag cgtggaatca aatggagtgg catttagttc   300
aggcggcttg ttccttgcca tggcaaagta tcaagaagat ccccaagtca agtcacattt   360
gtaaagctgc ttcccaattg gctttgtcac gcagtgttga agcagtggga gagagattca   420
cctgttataa aggaactgac taacacaagt atcccgtcta tatctgaatg ctgtctctag   480
```

METHODS AND COMPOSITIONS USING SPLICING REGULATORY PROTEINS INVOLVED IN TUMOR SUPPRESSION

CROSS-REFERENCE TO RELATED APPLICATIONS

This is a national stage application under 35 U.S.C. 371 of PCT/US2009/051239, filed on Jul. 21, 2009, which claims the benefit under 35 USC 119(e) of U.S. patent application Ser. No. 61/082,435, filed on Jul. 21, 2008 (now expired), all of which are incorporated by reference herein.

STATEMENT REGARDING FEDERALLY SPONSORED RESEARCH OR DEVELOPMENT

This invention was made with government support under Grant No. CA093769 awarded by the National Institutes of Health. The government has certain rights in the invention.

STATEMENT REGARDING FEDERALLY SPONSORED RESEARCH OR DEVELOPMENT

This invention was made with government support under grant no. R01- CA093769 awarded by the National Institutes of Health. The government has certain rights in the invention.

BACKGROUND OF THE INVENTION

The epithelial mesenchymal transition (EMT) and the reverse process of a mesenchymal to epithelial transition (MET) are fundamental processes during embryonic development. The changes associated with cellular plasticity that characterize them have been implicated in disease processes including cancer and fibrosis. There are numerous demonstrations that the EMT is a mechanism that can contribute to the metastatic process (Thiery, 2002; Yang and Weinberg, 2008). The EMT can be a transient and reversible process by which tumor cells acquire motile properties that allow escape from the primary tumor followed by an MET at a distant site of metastasis (Chaffer et al., 2007).

Changes in the activities of trans-acting regulators of splicing and of a number of specific splice variants have been shown to contribute to tumorigenesis (Hu and Fu, 2007). For example the SR protein SF2/ASF was shown to be a protooncogene that can drive tumorigenesis through the induction of changes in splicing of several target transcripts (Karni et al., 2007). In additional, splicing-specific microarray platforms that facilitate global analysis of splicing have shown the potential to yield "splicing signatures" that can be used for cancer diagnosis and prognosis (Blencowe, 2006).

Fibroblast growth factor receptor 2 (FGFR2) is a protein that plays a role in cancer progression. The protein has two mutually exclusive exons IIIb and IIIc generated by alternative splicing events. A number of studies have demonstrated that disruption of the splicing pathway that leads to epithelial FGFR2-IIIb can contribute to cancer progression. Collective results from several models of tumorigenesis have led to the proposal that FGFR2-IIIb is a tumor suppressor (Gross et al, 2005). A general feature in such models posits that a switch from expression of FGFR2-IIIb to FGFR2-IIIc severs dependence of epithelia for growth and proliferation on surrounding mesenchyme and may establish autocrine growth pathways through epithelial expression of ligands for FGFR2-IIIc (McKeehan et al, 1998). In some cases, the switch in splicing of FGFR2 is followed by transcriptional downregulation of FGFR2 and activation of FGFR1-IIIc, which has similar ligand binding preferences as FGFR2-IIIc (Feng et al, 1997; Matsubara et al, 1998).

Reciprocal, compartment specific expression of FGFR2 splice variants and their ligands that participate in paracrine interactions between epithelial and mesenchymal cells regulate cell proliferation and differentiation (Acevedo et al. 2007). The epithelial FGFR2-IIIb splice variant has been suggested to function as a tumor suppressor (Savagner et al., 1994; Thiery, 2002). FGFR2-IIIb has a critical role in the maintenance of an epithelial phenotype. A switch in splicing towards the mesenchymal FGFR-IIIc isoform and/or transcriptional inactivation FGFR2 accompanies the EMT, a process involved in tumor metastasis (Hovhannisyan and Carstens, 2007). Previous studies of FGFR2 splicing regulation have identified a number of auxiliary cis-elements and non-cell type-specific regulatory RBPs that can influence exon IIIb and exon IIIc splicing combinatorially (Carstens et al., 1998; Hovhannisyan and Carstens, 2005) and references therein). One or more unidentified epithelial cell type-specific splicing regulatory proteins have been suggested to constitute a master switch that is required for FGFR2-IIIb expression (Newman et al., 2006).

There remains a need in the art for compositions and methods for the identification and use of splicing regulatory proteins and targets of such splicing implicated in cancer development for diagnosis/prognosis and treatment of certain cancers, as well as for use in screening assays enabling the identification of therapeutically desirable or undesirable properties of proposed therapeutic compounds or molecules.

SUMMARY OF THE INVENTION

The invention described herein meets the needs of the art by providing methods and compositions utilizing newly identified FGFR2 splice regulatory factors that maintain epithelial differentiation through post-transcriptional control at the level of splicing, and sequences regulated by these splicing factors.

In one aspect, a diagnostic composition involves a reagent that is capable of identifying in a biological sample from a mammalian subject
 (a) a nucleic acid sequence encoding the epithelial cell type specific splicing factor ESRP1 or ESRP2, or the protein encoded thereby;
 (b) a nucleic acid sequence splice variant that encodes a protein that is upregulated by ESRP1 or ESRP2 expression levels in a healthy mammalian control subject, or the protein encoded thereby;
 (c) a nucleic acid sequence splice variant that encodes a protein that is down-regulated by ESRP1 or ESRP2 expression levels in the healthy control or the protein encoded thereby; and
 (d) an alternative nucleic acid sequence splice variant of (b) or (c) that encodes a protein that is expressed when ESRP1 or ESRP2 expression levels are down-regulated from those of the healthy control or the protein encoded thereby.

Certain embodiments of these compositions include probes, primer sets, or other ligands that identify nucleic acid sequences, also include panels of such probes, primer sets or other biomarkers. Other embodiments are ligands capable of detecting/measuring proteins of the splicing factors or targets.

In another aspect a diagnostic kit contains one or more of the reagents identified herein.

In another aspect, a method for detecting an epithelial to mesenchymal transition (EMT) comprises contacting a biological sample obtained from a mammalian subject with a diagnostic reagent that can measure or detect the expression level of at least one of the group consisting of (a) through (d) above; and detecting an EMT when the level of expression of (a) or (b) is below the level of expression thereof in the healthy mammalian control, when the level of expression of (c) or (d) is above the level of expression thereof in the healthy mammalian control. Detection of the EMT in the sample diagnoses the presence or propensity towards metastasis of a mammalian carcinoma or cancer derived from primary epithelial cells. Detection of the EMT in the sample may also be diagnostic of tissue fibrosis.

In another aspect, a method for determining the prognosis of a mammalian carcinoma or cancer derived from primary epithelial cells, metastasis or tissue fibrosis includes obtaining a biological sample from a mammalian subject; contacting a biological sample obtained from a mammalian subject at a first point in time with a diagnostic reagent that can measure or detect the expression level of at least one of (a) through (d) above, and contacting a biological sample obtained from a mammalian subject at a later point in time after the first point in time with the same diagnostic reagent. A diagnosis of metastatic or pre-metastatic cancer or increased likelihood of progression of mammalian carcinoma or cancer derived from primary epithelial cells or tissue fibrosis is made when the level of expression of (a) or (b) in the later sample is below the level of expression thereof in the first sample, or when the level of expression of (c) or (d) in the later sample is above the level of expression thereof in the first sample.

In another aspect, a screening assay includes culturing a host cell that does not express any epithelial splicing agent selected from the group consisting of ESPR1, ESPR2 or RNCP1. The cell is transfected with a minigene comprising a nucleic acid sequence that generates a detectable signal when the minigene is contacted with the splicing agent. The host cell is cultured in the presence of a test molecule; and the generation or absence of the signal in the host cell is detected. Generation of a signal in the host cell indicates that the test molecule mimics the splicing activity of the splicing agent.

In another aspect a compound that inhibits the metastatic process of carcinomas or cancers derived from epithelial cell types, or inhibits the progression of tissue fibrosis is identified by the assay. Such compounds may upon contact with a mammalian cell permit expression of at least one variant protein encoded by a nucleic acid sequence splice variant that is regulated by ESRP1 or ESRP2 in a pharmaceutically acceptable vehicle.

In another aspect, a method for suppressing metastasis of a mammalian carcinoma or cancer derived from primary epithelial cells or blocking the progression of tissue fibrosis includes delivering to the cell at least one of ESRP1 or ESRP2 or a molecule that mimics the splicing activity of the ESRP1 or ESRP2. In another embodiment, at least one of ESRP1 or ESRP2 or a molecule that mimics the splicing activity of the ESRP1 or ESRP2 is used in the treatment of or in the preparation of a medicament for the treatment of suppressing metastasis of a mammalian carcinoma or cancer derived from primary epithelial cells or blocking the progression of tissue fibrosis.

In another aspect, a composition includes an effective amount of a protein encoded by a nucleic acid sequence splice variant that is upregulated or downregulated by the ESRP1 or ESRP2 expression levels of a healthy mammalian subject, optionally with a pharmaceutically acceptable vehicle carrier.

In another aspect, a composition includes a ligand that binds to and inhibits expression of ESRP1, ESRP2 or a protein encoded by a nucleic acid sequence splice variant that is upregulated or downregulated by the ESRP1 or ESRP2 expression levels of a mammalian subject with an epithelial cell cancer, optionally with a pharmaceutically acceptable vehicle.

In another aspect, a method for diagnosing, classifying, or determining the prognosis of, a mammalian carcinoma or cancer derived from primary epithelial cells involves measuring the level of expression of at least one epithelial cell type specific splicing factor selected from ESRP1 and ESRP2 in a biological sample from a mammalian subject. In one embodiment, the subject's level of the factor is then compared to the level of the same factor in healthy subject, or to a reference standard developed from the average level in multiple healthy subjects. In another embodiment the subject's level of the factor is then compared to the level of that factor measured in an earlier biological sample of the same subject, or to a reference standard developed from the average level in multiple subjects having various stages of the cancer.

In another aspect, methods for diagnosing, or determining the prognosis of, tissue fibrosis in a mammalian subject involve measuring the level of expression of at least one epithelial cell type specific splicing factor selected from ESRP1 and ESRP2 in a mammalian subject's biological sample. In one embodiment, the subject's level of the factor is then compared to the level of the same factor in healthy subject, or to a reference standard developed from the average level in multiple healthy subjects. In another embodiment the subject's level of the factor is then compared to the level of that factor measured in an earlier biological sample of the same subject, or to a reference standard developed from the average level in multiple subjects having various stages tissue fibrosis.

In a further aspect, a method for diagnosing the occurrence, stage or progression of a disease or condition related to inappropriate splicing of FGFR2 involves measuring the level of expression of the splicing factor RNPC1 in a biological sample from a mammalian subject. In one embodiment, the subject's level of the factor is then compared to the level of the same factor in healthy subject, or to a reference standard developed from the average level in multiple healthy subjects. In another embodiment the subject's level of the factor is then compared to the level of that factor measured in an earlier biological sample of the same subject, or to a reference standard developed from the average level in multiple subjects having various stages of disease.

In another aspect, a diagnostic reagent comprises at least one polynucleotide immobilized on a substrate, wherein the polynucleotide is a genomic probe that hybridizes to at least one splicing factor selected from the group consisting of ESRP1, ESRP2 and RNPC1. Still other diagnostic compositions contain a PCR primer-probe set that amplifies a polynucleotide sequence of at least one splicing factor selected from ESRP1, ESRP2 and RNPC1. Still other diagnostic/prognostic reagents include a composition comprising a ligand that binds to an expression product of at least one mammalian splicing factor selected from the group consisting of ESRP1, ESRP2 and RNPC1 of a mammalian subject. Diagnostic reagents for the identification of a characteristic genetic profile of disease also include panels of multiple probes or gene sequences that comprise probes, primers or sequences of at least one mammalian splicing factor selected from the group consisting of ESRP1, ESRP2 and RNPC1. These sequences may be optionally immobilized. Such reagents are useful for diagnosing the occurrence, stage or progression of a disease or condition related to inappropriate splicing of FGFR2 or to a cancer in a mammalian subject. Such reagents are useful for diagnosing or monitoring the stage or progression of a mammalian carcinoma or cancer derived from primary epithelial cells. Such reagents are useful for diagnosing or monitoring the stage or progression of tissue fibrosis.

In yet a further aspect, a method of screening a test compound or molecule includes the steps of contacting the compound with a mammalian cell expressing the gene product of at least one splicing factor selected from the group consisting of ESRP1, ESRP2 and RNPC1. In one embodiment of this method, the effect of the compound on the expression level of the gene product or of FGFR2 by the cell is measured. In another embodiment, the mutagenic effect of the compound on the nucleotide sequence or amino acid sequences of ESRP1, ESRP2, RNPC1 or FGFR2 is determined. Any effect that decreases the expression level of the factor in the cell or alters the nucleotide or amino acid sequence of the resulting ESRP1, ESRP2, RNPC1 or FGFR2 in response to the test compound is a potentially undesirable effect of use of the test compound.

Another aspect of this invention is a high throughput splicing assay used to identify compounds that change splicing events. This assay involves contacting in each individual well of a multi-well plate a different cDNA with a mammalian cell that expresses a specific splice variant associated with a specific condition, e.g., FGFR2 Mb. The cell is transfected with a minigene that expresses luciferase only when the cell expresses a specific splice variant. Cells are analyzed for luminescence after additional of luciferase reagents. A change in the expression of the specific splice variant by the cell caused by any of the cDNA is correlated with a change in the level of luminescence in each well.

Yet another aspect involves a method for maintaining normal expression of FGFR2 in a cell which involves delivering to the cell at least one of ESRP1 or ESRP2 or RNCP1. This method of delivering ESRP1 or ESRP2 is useful for treating, or suppressing metastatis of, a mammalian carcinoma or cancer derived from primary epithelial cells. This method delivering ESRP1 or ESRP2 is useful for treating, or blocking the progression of, tissue fibrosis. In another embodiment, at least one of ESRP1 or ESRP2 or a molecule that mimics the splicing activity of the ESRP1 or ESRP2 is used in the treatment of or in the preparation of a medicament for the treatment of maintaining normal expression of FGFR2 in a cell.

In still a further aspect, a composition for such delivery comprises a plasmid or viral vector comprising a polynucleotide encoding at least one of ESRP1, ESRP2 and RNPC1 under the control of a promoter operable in eukaryotic epithelial cells in a pharmaceutically acceptable vehicle or carrier.

In another aspect, a pharmaceutical composition is provided that contains an effective amount of at least one of ESRP1, ESRP2 and RNPC1 in nucleic acid or protein form in a pharmaceutically acceptable vehicle.

Other aspects of the present invention are described in the detailed description which follows.

BRIEF DESCRIPTION OF THE FIGURES

FIG. 1A is a schematic representing the structural domains of the FGFR2 protein indicating Ig-like domains 1, 2 and 3, the transmembrane TM domain, and tyrosine kinase domains TK1 and TK2.

FIG. 1B is a map of the pre-mRNA with mutually exclusive splicing pathways that leads to expression of FGFR2-IIIb in epithelial cells or FGFR2-IIIc in mesenchymal cells.

FIG. 1C is a schematic representation of the bi-cistronic luciferase reporter minigene used in the over-expression screen. A fragment of FGFR2 intron 8 (IF3) known to contain all elements necessary for IIIb inclusion is cloned downstream of a synthetic 40 nt exon. Skipping of the exon generates a translation frame that stops upstream of the luciferase coding sequence. Inclusion of the exon results in translation through the luciferase open reading frame. Indicated splicing outcomes are illustrated.

FIG. 4A is a western gel showing that TWIST-induced EMT causes a change in splicing of FGFR2. FIGS. 4A-4C taken together show that a decrease in ESRP1 and ESRP2 expression is concurrent during an epithelial to mesenchymal transition, resulting in a IIIb to IIIc switch in FGFR2 splicing.

FIG. 4B is a gel showing expression of epithelial genes E-cadherin and Keratin 15 and mesenchymal genes N-cadherin and Foxc2 by RT-PCR of RNAs from HMLE cells expressing either the control vector pBabe-Puro or pBabe-Puro-Twist.

FIG. 4C is a graph showing the relative values of ESRP1, ESRP2, and miR-200c measured by real-time PCR in HMLE cells expressing either the control vector pBabe-Puro or pBabe-Puro-Twist.

FIG. 8A is a flowchart illustrating the experimental design of an siRNA and exon based microarray approach to identify alternative splicing events regulated by ESRP1 and ESRP2.

FIG. 8B is a graph depicting quantitative RT-PCR showing a greater than 80% decrease of ESRP1 and ESRP2 mRNA in the combined knockdown samples (siESRP1/2) versus the control (siGFP). The results represent the mean of three amplifications and error bars represent the standard deviation.

DETAILED DESCRIPTION OF THE INVENTION

Figure 2A:
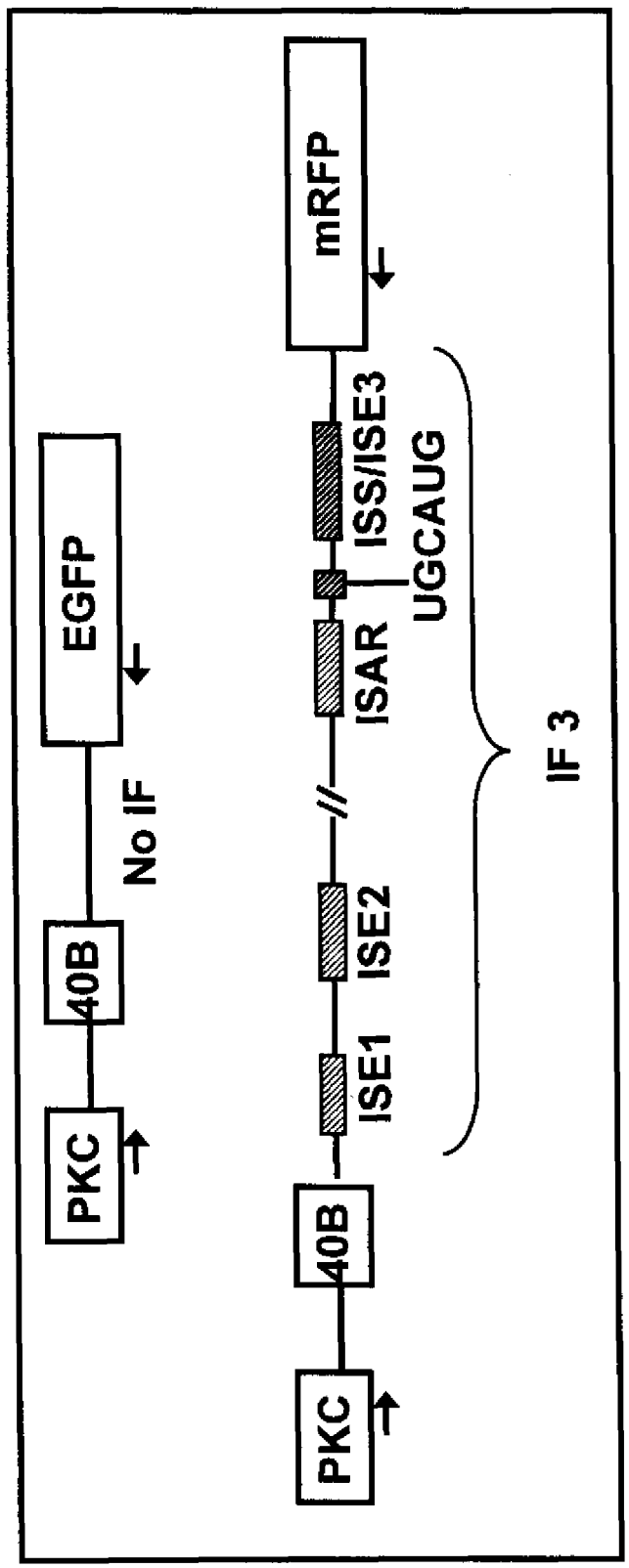
FIG. 2A is a schematic of a dual fluorescent minigene stably expressed in the 293T-clone2 cells. The EGFP minigene contains no FGFR2 sequences and the mRFP minigene has IF3 cloned downstream of exon 40B, respectively. The 293T-clone2 cells were transiently transfected with the MGC clones from Table 6 or empty vector (EV) as a negative control or Fox1 as a positive control. Splicing of the minigene was analyzed by RT-PCR using the primers indicated by arrows in the schematic.

This invention involves the identification and use of splicing factors that maintain epithelial differentiation through post-transcriptional control at the level of splicing. Thus this invention provides methods for diagnosis and prognosis of diseases related to inappropriate splice events that lead to disease, as well as compositions to perform such methods, and therapeutic screens and compositions to treat and potentially reverse such splice events.

The inventors used highly advanced sensitive and specific luciferase splicing reporter minigenes to carry out a genome wide high throughput array based cDNA overexpression screen for splicing regulatory proteins that regulate splicing of fibroblast growth factor receptor 2 (FGFR2). This screen identified 28 candidates capable of conferring a splicing change in the reporter (see Table 6). The assay identified an epithelial cell type-specific RNA binding, splicing regulatory protein, Epithelial Splicing Regulatory Protein (ESRP) that was required for maintenance of FGFR2-IIIb splicing. Analysis of a panel of cell lines confirmed that expression of ESRP is limited to cells that express FGFR2-IIIb. ESRP when expressed ectopically, by itself switched splicing of endogenous FGFR2 from mesenchymal-specific exon IIIc to epithelial-specific exon IIIb in a cell line, 293T, that expresses FGFR2-IIIc. The inventors subsequently also noted that a close homolog of this gene (ESRP2) displayed the same expression pattern and function and is a functionally redundant protein. Neither of these genes nor their gene products (which were previously only identified by general gene name RNA binding motif protein 35a and 35b) had previously been shown to be regulators of alternative splicing or to be epithelial cell type-specific. At least one non-cell type-specific factor (RCNP1) was also identified.

The ESRPs co-regulate alternative splicing decisions that are epithelial-specific. In a panel of cell lines expressing either FGFR2-IIIb or FGFR2-IIIc, the inventors found exclusive expression of the mRNAs encoding these proteins in cell lines that express FGFR2-IIIb, suggesting that ESRP1 is a critical regulator of this cell type-specific splicing event. Additional regulated events comprise an epithelial cell type-specific "splicing signature" that maintains epithelial cell morphology and function.

Loss of expression of these splicing factors contributes to the epithelial-to-mesenchymal transition, a process implicated in cancer metastasis. The inventors used a model of the EMT in which the transcriptional factor Twist induces an EMT in a Human Mammary Epithelial Cell line (HMEC) (8). Upon induction of EMT with Twist, the inventors observed that ESRP mRNA that was initially detectable became undetectable by RT-PCR. This did not occur in the controls. These findings strongly support that loss of ESRP1 expression is a critical event that occurs during the EMT. Thus, the loss of the corresponding epithelial cell type-specific splicing regulatory program is also broadly compromised during cancer progression. In addition to regulating FGFR2 splicing, these factors also coordinately regulate the splicing of other alternatively spliced transcripts that are implicated in carcinogenesis. Thus, these proteins participate in the cellular processes that maintain epithelial cell differentiation. These factors themselves, as well as other targets the splicing of which is regulated by ESRP1 and ESRP2, are useful in as biomarkers for diagnosis of certain epithelial cancers, cancer metastasis and/or tissue fibrosis in biological samples, such as biopsied tissue. These factors are also useful as targets to identify other compounds and molecules useful for cancer prevention, diagnosis, and treatment, and as diagnostic and therapeutic reagents themselves.

ESRP1 and 2 thus join the list of a very limited number of mammalian cell type-specific alternative splicing regulators. The loss of these splicing factors may be universally observed during the EMT by investigating its expression in several additional EMT systems. The inventors are investigating expression of ESRP2 in a panel of human cancer specimens. In one embodiment, ESRPs are frequently lost during cancer progression, and so provide a marker of cancer progression. In another embodiment, loss of ESRP expression is more frequently seen in aggressive and rapidly progressing cancer and thus it provides a marker of cancer classification and diagnosis.

Further assays that controls ESRP1/2 expression or that may restore the factors to normal expression levels are useful for the development of therapeutic strategies. Expression levels of these ESRP1/2 factors, and of targets spliced by these factors, are useful as highly specific markers of the epithelial lineage for tracking disease development and progression.

A. Definitions

By "ESRP1" or Epithelial Splicing Regulatory Protein 1 is meant the nucleic acid sequences and encoded amino acid sequences of the factor previously identified as RBM35A. The nucleotide sequence(s) and protein sequences for the five known human isoforms of this ESRP1 are published in the NCBI database at accession numbers NM_001034915.2/ NP_001030087.2 (isoform 2), NP_001122825.1/NP_ 001116297.1 (isoform 4); NM_001122826.1/NP_ 00116298.1 (isoform 3); NM_001122827.1/NP_ 001116299.1 (isoform 5) and NM_017697.3/NP_060167.2 (isoform 1). A murine homolog is reported at accession No. NM_194055. Other homologs are also known and, where homologous, are anticipated to be useful in the various methods and compositions of this invention. This invention involves the identification of this protein as an epithelial cell-type specific splicing factor that maintains epithelial differentiation through post-transcriptional control at the level of splicing.

By "ESRP2" or Epithelial Splicing Regulatory Protein 2 is meant the nucleic acid sequences and encoded amino acid sequences of the factor previously identified as RBM35B. The nucleotide sequence(s) and protein sequences for the known human protein are published in the NCBI database at accession numbers NM_024939.2/NP_079215.2. A murine homolog is reported at accession No. NM_176838. Other homologs are also known and where homologous are anticipated to be useful in the various methods and compositions of this invention. This invention involves the identification of this protein as an epithelial cell-type specific splicing factor that maintains epithelial differentiation through post-transcriptional control at the level of splicing.

By "RNPC1" is meant the nucleic acid sequences and encoded amino acid sequences of the factor previously identified as RBM38. The inventors are the first to demonstrate that this factor regulates splicing in mammals. The nucleotide sequence(s) and protein sequences for the two known human isoforms of this protein are published in the NCBI database at accession numbers NM_017495.4/NP_059965.2 and NM_183425.1/NP_906270.1. A murine homolog is similarly available under accession No. NM_019547. Other homologs are also known and, where homologous, are anticipated to be useful in the various methods and compositions of this invention.

By the phrase "a mammalian carcinoma or cancer derived from primary epithelial cells" is meant an epithelial cell cancer selected from the group consisting of carcinomas that derive from epithelial cell types. Among such cancers are included breast cancer, colorectal cancer, ovarian cancer, lung cancer, pancreatic cancer, kidney cancer, prostate cancer and gastric cancer, among others. Also included among these cancers are aggressive cancer subtypes, basal cancer or lobular cancer, e.g., certain aggressive breast cancers.

By the phrase "biological sample" is meant any biological fluid or tissue. In certain embodiments, a sample may be a fluid or tissue containing epithelial cells, either benign or malignant cells. Useful biological samples include, without limitation, whole blood, saliva, urine, synovial fluid, bone marrow, cerebrospinal fluid, vaginal mucus, cervical mucus, nasal secretions, sputum, semen, amniotic fluid, bronchoalveolar lavage fluid, and other cellular exudates from a mammalian subject, as well as tissue biopsies including lymph nodes. Such samples may further be diluted with saline, buffer or a physiologically acceptable diluent. Alternatively, such samples are concentrated by conventional means. Additionally, the biological sample may be a blood sample in which circulating tumor cells are found, i.e., such as a sample used in the CellSearch® Circulating Tumor Cell (CTC) Kit (Veridex).

The term "tumor," as used herein, refers to all neoplastic cell growth and proliferation, whether malignant or benign, and all pre-cancerous and cancerous cells and tissues.

By the terms "patient" or "subject" as used herein means a mammalian animal, including a human, a veterinary or farm animal, a domestic animal or pet, and animals normally used for clinical research. More specifically, the subject of these methods and compositions is a human.

The term "prognosis" is used herein to refer to the prediction of the likelihood of cancer-attributable death or progression, including recurrence, metastatic spread, and drug resistance, of a neoplastic disease, particularly an epithelial cell-type specific cancer. The term "prediction" is used herein to refer to the likelihood that a patient will respond either favorably or unfavorably to a drug or set of drugs, and also the extent of those responses, or that a patient will survive following surgical removal of the primary tumor and/or chemotherapy for a certain period of time without cancer recurrence. These predictive methods can be used clinically to make treatment decisions by choosing the most appropriate treatment modalities for any particular patient. The predictive methods described herein are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely. These predictive methods are also useful in identifying aggressive cancers and the occurance of metastatic cancer conditions.

The terms "splicing" and "RNA splicing" are used interchangeably and refer to RNA processing that removes introns and joins exons to produce mature mRNA with continuous coding sequence that moves into the cytoplasm of a eukaryotic cell.

The term "exon" refers to any segment of an interrupted gene that is represented in the mature RNA product. In theory the term "intron" refers to any segment of DNA that is transcribed but removed from within the transcript by splicing together the exons on either side of it. Operationally, exon sequences occur in the mRNA sequence of a gene. Operationally, intron sequences are the intervening sequences within the genomic DNA of a gene, bracketed by exon sequences and having GT and AG splice consensus sequences at their 5' and 3' boundaries.

By the term "functional fragment" is meant any fragment of a nucleotide or amino acid sequence that shares a common biological function of the entire sequence.

By the term "target" of ESRP1/2 is meant a nucleic acid sequence that can be spliced by ESRP1/2, or a mimic of ESRP1/2. Generally, in the presence of normal amounts of ESRP1/2 in a healthy subject, certain target proteins are expressed that contain an exon, e.g., a normal enhanced target variant or "enhanced target". When ESRP1/2 are downregulated, e.g., in the conditions of a cancer or tissue fibrosis, the enhanced target is downregulated and an "alternative splice variant of an enhanced target" is expressed, i.e., the exon is spliced out. Additionally, in the presence of normal amounts of ESRP1/2 in a healthy subject, certain target proteins that contains an exon are silenced, e.g., a normal silenced target splice variant or "silenced target". When ESRP1/2 are downregulated, e.g., in the conditions of a cancer or tissue fibrosis, the silenced target is downregulated and an "alternative splice variant of a silenced target" is expressed, i.e., the exon is expressed. Certain of these enhanced or silenced targets are identified herein.

Unless defined otherwise in this specification, technical and scientific terms used herein have the same meaning as commonly understood by one of ordinary skill in the art to which this invention belongs and by reference to published texts.

B. Diagnostic Methods and Reagents

The ESRP1/2 splicing factors and their targets are useful in diagnostic methods and as reagents for the diagnosis of cancer, metastatic cancer, tissue fibrosis or cancer fibrosis based upon the relationship of the splicing activity to the EMT.

One embodiment of such a diagnostic method detects an epithelial to mesenchymal transition (EMT) in the biological sample of a subject. In one embodiment the method includes contacting a biological sample obtained from a mammalian subject with a diagnostic reagent that can measure or detect the expression level of at least one of (a) a nucleic acid sequence encoding the epithelial cell type specific splicing factor ESRP1 or ESRP2, or the protein encoded thereby; (b) a nucleic acid sequence splice variant that encodes an "enhanced" protein that is upregulated by ESRP1 or ESRP2 expression levels in a healthy mammalian control subject, or the protein encoded thereby; (c) a nucleic acid sequence splice variant that encodes a "silenced" protein that is downregulated by ESRP1 or ESRP2 expression levels in the healthy control or the protein encoded thereby; and (d) an alternative nucleic acid sequence splice variant of (b) or (c) that encodes a protein variant that is expressed when ESRP1 or ESRP2 expression levels are down-regulated from those of the healthy control or the protein encoded thereby. In one embodiment, the diagnostic method further involves detecting an EMT when the level of expression of (a) or (b) is below the level of expression thereof in the healthy mammalian control. In another embodiment, the diagnostic method detects an EMT when the level of expression of (c) or (d) is above the level of expression thereof in the healthy mammalian control. In another embodiment, detection of the EMT in the sample correlates with, or is indicative of, the presence or metastasis of a mammalian carcinoma or cancer derived from primary epithelial cells. In another embodiment, detection of the EMT in the sample is indicative of tissue fibrosis.

In another embodiment of a diagnostic method, the contacting step measures (a), (b), (c) or (d) as ribonucleic acid, mRNA, deoxyribonucleic acid or cDNA sequences. In another embodiment of a diagnostic method, the contacting step measures (a), (b), (c) or (d) as the target protein. In another embodiment, the contacting step of the method involves forming a physical association between the diagnostic reagent and the splicing factor or target sequence or protein in the sample. One such reagent is a nucleic acid sequence capable of hybridizing to a target-containing sequence in the sample. For example, when the reagent is a genomic probe, the physical association formed by contact of the reagent with the sample is the hybridization of the probe to the cDNA or mRNA of a sequence containing the target sequence.

Where the reagent is a PCR primer or primer pair, the physical association is the hybridization of the primer sequences to different strands or different portions of the nucleic acid (e.g., mRNA) of a marker sequence containing the target sequence. Preferably the nucleic acid probes or primers are from about 8 or more nucleotides in length, wherein the nucleotides are complementary to portions of the "non-coding" or "coding" strands of the gene sequences or non-gene sequences flanking or encompassing the selected target sequence. Such probes are, for example, oligo or polynucleotide sequences corresponding to the region surrounding (and/or comprising) any of the target sequences. Such a fragment usually has a length comprised between 8 and 50 nucleotides, preferably 12 to 35 nucleotide or 15 to 25 nucleotides. It may be a fragment of naturally occurring or synthetic DNA or RNA. In certain embodiments, each primer or probe is at least 9, 10, 11, 12, 13, 14, 15, 16, 17, 18, 19 or at least 20 nucleotides in length. In other embodiments, the primers and/or probes may be longer than 20 nucleotides in length. Given the information provided herein, one of skill in the art may design any number of suitable primer/probe sequences useful for identifying the target sequences described herein. The diagnostic methods described herein can employ one or more of the diagnostic reagents or compositions described below.

Where the diagnostic reagent employed in the method is associated with a detectable label, the method further comprises transforming the detectable label's signals generated from the diagnostic reagent in association with (a), (h), (c) or (d) present in the biological sample into numerical or graphical data. In yet another embodiment, the transforming is performed by a suitably-programmed machine or instruments that can detect the detectable signals generated from the diagnostic reagents associated with the (a), (b), (c) or (d) present in the biological sample and transform same into numerical or graphical data useful in performing the diagnosis.

Another aspect of the invention is a method for determining the prognosis of a mammalian carcinoma or cancer derived from primary epithelial cells, metastasis or tissue fibrosis. In one embodiment the method comprises obtaining a biological sample from a mammalian subject; contacting a biological sample obtained from a mammalian subject at a first point in time with a diagnostic reagent that can measure or detect the expression level of at least one of the group consisting of (a) a nucleic acid sequence encoding the epithelial cell type specific splicing factor ESRP1 or ESRP2, or the protein encoded thereby; (b) a nucleic acid sequence splice variant that encodes a protein that is upregulated by ESRP1 or ESRP2 expression levels in a healthy mammalian control subject, or the protein encoded thereby; (c) a nucleic acid sequence splice variant that encodes a protein that is downregulated by ESRP1 or ESRP2 expression levels in the healthy control or the protein encoded thereby; and (d) an alternative nucleic acid sequence splice variant of (b) or (c) that encodes a protein that is expressed when ESRP1 or ESRP2 expression levels are down-regulated from those of the healthy control or the protein encoded thereby. The method further comprises contacting a biological sample obtained from a mammalian subject at a later point in time after the first point in time with the same diagnostic reagent and diagnosing ongoing metastasis or progression of mammalian carcinoma or cancer derived from primary epithelial cells or tissue fibrosis when the level of expression of (a) or (b) in the later sample is below the level of expression thereof in the first sample, or when the level of expression of (c) or (d) in the later sample is above the level of expression thereof in the first sample.

Normally, such diagnostic methods are performed on biological samples containing mammalian cells, biological fluids containing mammalian cells, mammalian tissue, and biopsied tissue. The cancer can be characterized by inappropriate expression of splice variants of fibroblast growth factor receptor 2, or any other suitable target of the splicing factors ESRP1/2 due to inappropriate splicing. In another embodiment, the cancer is an epithelial cell cancer or carcinoma that derives from epithelial cell types consisting of breast cancer, colorectal cancer, ovarian cancer, lung cancer, kidney cancer, pancreatic cancer, prostate cancer and gastric cancer.

In another embodiment, the diagnostic method can detect an expression level of one or more of (a) through (d) that is indicative of epithelial cancer cells that have undergone a partial or complete epithelial to mesenchymal transition (EMT) and are metastatic. In another embodiment, the expression level of one or more of (a)-(d) is associated with an aggressive breast cancer subtype. In another embodiment, the cancer subtype is a basal cancer or a lobular cancer. In another embodiment, the expression level of one or more of (a)-(d) is associated with a cancer having a severe prognosis.

In another embodiment, a method for diagnosing or classifying a mammalian carcinoma or cancer derived from primary epithelial cells utilizes the splicing factors identified herein. In one embodiment, such a diagnostic method involves measuring the level of expression of at least one epithelial cell type specific splicing factor selected from ESRP1 and ESRP2 in a biological sample obtained from a mammalian subject. The expression level of the desired factor is then compared with the level of expression in a healthy mammalian subject. While such comparison can occur by direct comparison with the expression levels in one or more healthy subjects, it is more typical for a reference average expression level to be provided as a number or range. A level of expression of the splicing factor in the subject's sample that is below the level of expression in a healthy mammalian subject (or reference average) is an indication of a diagnosis or severity of a cancer. In one embodiment of such a method the measuring step includes measuring the splicing factor as ribonucleic acid, deoxyribonucleic acid, or protein using conventional assay technologies.

In a similar manner, the method for diagnosing or classifying a mammalian carcinoma or cancer derived from primary epithelial cells utilizes the impact of these splicing factors identified herein on the resulting expression of FGFR2 splice variants or another target of the splicing factors. For ease of discussion, FGFR2 will be used as a prototype of all targets of the splicing factors. Where FGFR2 is mentioned, the other targets can be referenced similarly. In one embodiment, such a diagnostic method involves measuring the level of expression of FGFR2 splice variants or a desired splice variant thereof in a biological sample obtained from a mammalian subject. The expression level of the desired FGFR2 variant is then compared with the level of expression in a healthy mammalian subject. While such comparison can occur by direct comparison with the expression level of one or more healthy subjects, it is more typical for a reference average expression level to be provided as a reference number. A level of expression of the splicing factor in the subject's sample that is below the level of expression in a healthy mammalian subject (or reference average) is an indication of a diagnosis or severity of a cancer. In one embodiment of such a method the measuring step includes measuring the splicing factor as ribonucleic acid, deoxyribonucleic acid, or protein using conventional assay technologies. In another embodiment, the cancer is characterized by inappropriate expression of fibroblast growth factor receptor 2 due to inappropriate splicing.

In another aspect, a method for determining the prognosis of a mammalian carcinoma or cancer derived from primary epithelial cells involves measuring the level of expression of at least one epithelial cell type specific splicing factor selected from ESRP1 and ESRP2 in a biological sample from a mammalian subject with the cancer. The expression level of the desired factor is then compared with the level of expression in one or more biological samples of the same subject assayed earlier in time, or before or during treatment. While such comparison can occur by direct comparison with one or more prior assessments of the same patient's status, it is also possible for a reference average expression level at specific stages or severities of the disease among other patients with the disease to be provided as a reference number or profile. A level of expression of the splicing factor in the subject's sample that is below the subject's prior level of expression (or reference average) is an indication of a bad prognosis or increasing severity of the cancer. A level of expression of the splicing factor in the subject's sample that is above the subject's prior level of expression (or reference average) is an indication of a good prognosis or decreasing severity or spread of the cancer. In one embodiment of such a method the measuring step includes measuring the splicing factor level as ribonucleic acid, deoxyribonucleic acid, or protein using conventional assay technologies. Similarly, this strategy can be employed measuring FGFR2 variants as described above.

In another aspect, a method for diagnosing tissue fibrosis in a mammalian subject involves measuring the level of expression of at least one epithelial cell type specific splicing factor selected from ESRP1 and ESRP2 or a target thereof in a mammalian subject's biological sample. The expression level of the desired factor is then compared with the level of expression in a healthy mammalian subject. While such comparison can occur by direct comparison with the expression level of one or more healthy subjects, it is more typical for a reference average expression level to be provided as a reference number. A level of expression of the splicing factor in the subject's sample that is below the level of expression in a healthy mammalian subject (or reference average) is an indication of a diagnosis or severity of the tissue fibrosis. In one embodiment of such a method the measuring step includes measuring the splicing factor as ribonucleic acid, deoxyribonucleic acid, or protein using conventional assay technologies. A level of expression of the splicing factor below the level of expression of a healthy mammalian subject is evidence of tissue fibrosis or advancing tissue fibrosis. A level of expression of the splicing factor at or above the level of expression of a healthy mammalian subject is evidence of no diagnosis of tissue fibrosis.

In another aspect, a method for determining the prognosis of tissue fibrosis in a mammalian subject includes measuring the level of expression of at least one epithelial cell type specific splicing factor selected from ESRP1 and ESRP2 in a biological sample from a subject with tissue fibrosis.

In the same manner as above for epithelial cell derived carcinoma, the expression level of the splicing factor is compared to that in an earlier biological sample of the same subject (or reference sample number derived from multiple patients at various stages of tissue fibrosis). A decrease in the factor expression over the prior or reference sample is indicative of worsening disease, while an increase in the factor expression over the prior or reference sample is indicative of a good prognosis or success of treatment.

In yet another aspect, a method for diagnosing the occurrence, stage or progression of a disease or condition related to inappropriate splicing of FGFR2 involves measuring the level of expression of the splicing factor RNPC1 in a biological sample from a mammalian subject. The expression level of the splicing factor is compared to a healthy patient or healthy patient reference average for diagnosis. An expression level below the level of expression of a healthy mammalian subject is evidence of a positive diagnosis of such disease or condition.

The specific methodologies that can be employed to perform the diagnostic methods described herein are convention and may be readily selected and adapted by one of skill in the art. Methods useful in performing the diagnostic steps described herein are known and well summarized in U.S. Pat. No. 7,081,340. Such methods include methods based on hybridization analysis of polynucleotides, methods based on sequencing of polynucleotides, proteomics-based methods or immunochemistry techniques. The most commonly used methods known in the art for the quantification of mRNA expression in a sample include northern blotting and in situ hybridization; RNAse protection assays; and PCR-based methods, such as reverse transcription polymerase chain reaction (RT-PCR) or qPCR. Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS). The methods described herein are not limited by the particular techniques selected to perform them. Exemplary commercial products for generation of reagents or performance of assays include TRI-REAGENT, Qiagen RNeasy mini-columns, MASTERPURE Complete DNA and RNA Purification Kit (EPICENTRE®, Madison, Wis.), Paraffin Block RNA Isolation Kit (Ambion, Inc.) and RNA Stat-60 (Tel-Test), the MassARRAY-based method (Sequenom, Inc., San Diego, Calif.), differential display, amplified fragment length polymorphism (iAFLP), and BeadArray™ technology (Illumina, San Diego, Calif.) using the commercially available Luminex100 LabMAP system and multiple color-coded microspheres (Luminex Corp., Austin, Tex.) and high coverage expression profiling (HiCEP) analysis.

In conjunction with the performance of the various diagnostic techniques described herein, another aspect of the invention is a variety of diagnostic reagents employing the identified splice regulators ESRP1, ESRP2 or RNCP1 or targets thereof.

In one embodiment, a diagnostic composition includes a reagent that is capable of identifying in a biological sample from a mammalian subject at least one of (a) a nucleic acid sequence encoding the epithelial cell type specific splicing factor ESRP1 or ESRP2, or the protein encoded thereby; (b) a nucleic acid sequence splice variant that encodes a protein that is upregulated by ESRP1 or ESRP2 expression levels in a healthy mammalian control subject, or the protein encoded thereby; (c) a nucleic acid sequence splice variant that encodes a protein that is down-regulated by ESRP1 or ESRP2 expression levels in the healthy control or the protein encoded thereby; and (d) an alternative nucleic acid sequence splice variant of (b) or (c) that encodes a protein that is expressed when ESRP1 or ESRP2 expression levels are down-regulated from those of the healthy control or the protein encoded thereby. For example, in one embodiment, the nucleic acid sequence splice variants are identified as described in Examples 11 and 12.

In another embodiment, the diagnostic composition comprises multiple reagents capable of identifying more than one sequence or protein of (a), (b), (c) or (d). In another embodiment, the reagent is capable of forming a physical association with one or more variant protein or nucleic acid sequence of (a), (b), (c) or (d) in a biological sample. In yet another embodiment the reagent comprises a nucleic acid sequence capable of hybridizing with a nucleotide sequence of one or more of (a) through (d). In another embodiment, the reagent is a genomic probe that hybridizes to the cDNA or mRNA of a sequence of (a), (b), (c) or (d). In another embodiment, the reagent is a PCR primer probe set that hybridizes to the mRNA of a sequence of (a), (b), (c) or (d). In another embodiment, the reagent is an antibody or functional fragment thereof that binds to at least protein of (a), (b), (c) or (d).

The diagnostic reagent nucleic acid sequence may be an mRNA sequence, a DNA sequence, or a cDNA sequence. For example, an exemplary reagent can target either the nucleic acid sequence (b) of at least one "enhanced" target gene of Table 1, wherein the nucleic acid sequence indicative of ESRP1 or 2 upregulation lacks the specified exon, or the protein encoded thereby. In another embodiment, the reagent targets either the nucleic acid sequence (c) of at least one "silenced target" gene of Table 2, wherein the sequence indicative of ESRP1 or 2 downregulation contains the specified exon, or the protein encoded thereby.

The sequences of the gene targets, exons and nucleotide positions referenced throughout the specification and in the following examples are publically known and available to one of skill in the art. All chromosomal coordinates are available publicly. See, e.g., UC Santa Cruz Genome Browser, March 2006 Assembly, among other known databases containing the sequences referenced throughout this specification.

Tables 1 through 3 identify the gene symbol identifier; the chromosomal coordinates of the identified exon; and whether ESRP1 and ESRP2 "enhances" or "silences" production of the version of the protein encoded by the nucleic acid sequence containing the exon identified by the exon coordinates, etc. By "enhances", it is meant that expression of ESRP1 or ESRP2 increases production of the protein encoded by the nucleic acid splicing variant sequence which includes the identified exon. By "silences", it is meant that expression of ESRP1 or ESRP2 increases production of the protein encoded by the nucleic acid splicing variant sequence which does not include the identified exon.

TABLE 1

Enhanced Targets of ESRP1/2

| Gene Symbol | Exon Coordinates | ESRP Effect On Splicing | Percent Change Exon Inclusion | SEQ ID NOs of Exon Coordinates of Col. 2 |
|---|---|---|---|---|
| SLC37A2 | chr11: 124461310-124461366 | Enhance | 76.5 | 1 |
| FLNB | chr3: 58102625-58102696 | Enhance | 74 | 2 |
| RALGPS2 | chr1: 177127988-177128065 | Enhance | 65.5 | 3 |
| ENAH | chr1: 223759316-223759378 | Enhance | 62 | 4 |
| ITGA6 | chr2: 173074746-173074875 | Enhance | 60.5 | 5 |
| FNIP1 | chr5: 131074170-131074253 | Enhance | 41 | 31 |
| GOLGA2 | chr9: 130069294-130069374 | Enhance | 39.5 | 6 |
| ARFGAP2 | chr11: 47150836-47150877 | Enhance | 35 | 7 |
| TCF7L2 | chr10: 114714305-114714373 | Enhance | 29.2 | 8 |
| SLK | chr10: 105760564-105760656 | Enhance | 28 | 9 |
| MAP3K7 | chr6: 91310992-91311072 | Enhance | 26.5 | 10 |
| MPZL1 | chr1: 166011925-166012027 | Enhance | 26 | 11 |
| HISPPD1 | chr5: 102546834-102547007 | Enhance | 23.5 | 12 |
| INTS9 | chr8: 28760183-28760245 | Enhance | 22.2 | 13 |
| ARFIP1 | chr4: 154011355-154011450 | Enhance | 21.7 | 14 |
| YAP1 | chr11: 101585458-101585505 | Enhance | 19.9 | 15 |
| CCAR1 | chr10: 70186036-70186246 | Enhance | 19.5 | 16 |
| GSK3B | chr3: 121068127-121068165 | Enhance | 15 | 17 |
| NT5C3 | chr7: 33042071-33042125 | Enhance | 8 | 18 |
| VPS39 | chr15: 40271556-40271588 | Enhance | 7.4 | 19 |

TABLE 2

Silenced Targets of ESRP1/2

| Gene Symbol | Exon Coordinates | ESRP Effect On Splicing | % Change Exon Inclusion | SEQ ID NOS of Exon Coordinates of Col. 2 |
|---|---|---|---|---|
| SCRIB | chr8: 144961710-144961772 | Silence | 66 | 20 |
| OSBPL3 | chr7: 24869344-24869436 | Silence | 53 | 21 |
| COL16A1 | chr1: 31917992-31918039 | Silence | 46.0 | 22 |
| PLAA | chr9: 26907095-26907163 | Silence | 44.9 | 23 |
| MAP3K7 | chr6: 91284887-91285002 | Silence | 44 | 24 |
| PQLC3 | chr2: 11232545-11232586 | Silence | 42 | 25 |
| GOLGA4 | chr3: 37377738-37377800 | Silence | 39 | 26 |
| PRC1 | chr15: 89313313-89313354 | Silence | 36.1 | 27 |
| MEST | chr7: 129927866-129927967 | Silence | 35 | 28 |
| UBE2K | chr4: 39455697-39455825 | Silence | 35 | 29 |
| TBC1D23 | chr3: 101513367-101513411 | Silence | 33 | 30 |
| MPRIP | ehr17: 17019332-17019451 | Silence | 32 | 32 |
| ARHGEF11 | chr1: 155174834-155174929 | Silence | 31.2 | 33 |
| ATP13A3 | chr3: 195614217-195614306 | Silence | 29.5 | 34 |
| RIPK2 | chr8: 90844194-90844347 | Silence | 28.5 | 35 |
| WDR32 | chr9: 37847238-37847348 | Silence | 27.5 | 36 |
| MST4 | chrX: 131031187-131031372 | Silence | 26 | 37 |
| RBM34 | chr1: 233390449-233390585 | Silence | 25 | 38 |
| FAM13B1 | chr5: 137320065-137320130 | Silence | 23 | 39 |
| MRPL22 | chr5: 154310574-154310691 | Silence | 23 | 40 |
| LAS1L | chrX: 64670215-64670340 | Silence | 21.5 | 41 |
| PARL | chr3: 185034206-185034307 | Silence | 21.5 | 42 |
| ZNF207 | chr17: 27712600-27712647 | Silence | 21 | 43 |
| PSAT1 | chr9: 80132787-80132924 | Silence | 20.5 | 44 |
| GPR126 | chr6: 142746590-142746673 | Silence | 20 | 45 |
| STX2 | chr12: 129846493-129846618 | Silence | 20.0 | 46 |
| LAS1L | chrX: 64661169-64661219 | Silence | 19.5 | 47 |
| SEP15 | chr1: 87106324-87106373 | Silence | 18 | 48 |
| NAE1 | chr16: 65416259-65416289 | Silence | 16 | 49 |
| CLSTN1 | chr1: 9720143-9720199 | Silence | 15.5 | 50 |
| EHBP1 | chr2: 63068570-63068677 | Silence | 14.1 | 51 |
| RBM39 | chr20: 33791861-33791933 | Silence | 14 | 52 |
| GNAS | chr20: 56907391-56907435 | Silence | 13.5 | 53 |
| CSDA | chr12: 10753774-10753980 | Silence | 13.5 | 54 |
| REPS1 | chr6: 139289231-139289311 | Silence | 13.2 | 55 |
| ATXN2 | chr12: 110386849-110386902 | Silence | 9 | 56 |
| FAM126A | chr7: 22953096-22953391 | Silence | 8.9 | 57 |
| PACRGL | chr4: 20335529-20335609 | Silence | 8.7 | 58 |

TABLE 2-continued

Silenced Targets of ESRP1/2

| Gene Symbol | Exon Coordinates | ESRP Effect On Splicing | % Change Exon Inclusion | SEQ ID NOS of Exon Coordinates of Col. 2 |
|---|---|---|---|---|
| NUMB | chr14: 72815742-72815885 | Silence | 8.3 | 59 |
| CASK | chrX: 41301229-41301297 | Silence | 8 | 60 |
| ANKRD36 | chr2: 97153924-97154061 | Silence | 7.5 | 61 |
| CRAMP1L | chr16: 1656075-1656179 | Silence | 7.3 | 62 |
| ATP13A2 | chr1: 17188969-17189085 | Silence | 6.7 | 63 |
| FN1 | chr2: 215953779-215954048 | Silence | 6.5 | 64 |
| DOCK7 | chr1: 62783206-62783298 | Silence | 5.6 | 65 |

In another embodiment, the diagnostic reagent compositions employs the nucleic acid sequences or encoded proteins of only those target genes of Table 1 or 2, wherein the percent change of exon inclusion is greater than 25%. In another embodiment, the diagnostic reagent compositions employs the nucleic acid sequences or encoded proteins of only those target genes of Table 1 or 2, wherein the percent change of exon inclusion is greater than 30%. In another embodiment, the diagnostic reagent compositions employs the nucleic acid sequences or encoded proteins of only those target genes of Table 1 or 2, wherein the percent change of exon inclusion is greater than 40%. In another embodiment, the diagnostic reagent compositions employs the nucleic acid sequences or encoded proteins of only those target genes of Table 1 or 2, wherein, for the genes of Table 1, the exons are excised or the gene variants of Table 2 wherein the exons are present.

In one embodiment, the diagnostic composition comprises multiple reagents capable of identifying more than one sequence or protein selected from the group consisting of SLC37A2 FLNB, RALGPS2, ENAH, and ITGA6. In another embodiment, the diagnostic composition comprises multiple reagents capable of identifying more than one sequence or protein selected from the group consisting of SCRIB, OSBPL3, COL16A1, PLAA, and MAP3K7. In another embodiment, the diagnostic composition comprises multiple reagents capable of identifying more than one sequence or protein selected from the group consisting of SLC37A2, FLNB, RALGPS2, ENAH, ITGA6, SCRIB, OSBPL3, COL16A1, PLAA, and MAP3K7. In another embodiment, the diagnostic composition comprises multiple reagents capable of identifying at least three, four, five, six, seven, eight, nine or ten sequences or proteins selected from the group consisting of SLC37A2, FLNB, RALGPS2, ENAH, ITGA6, SCRIB, OSBPL3, COL16A1, PLAA, and MAP3K7. In another embodiment, the diagnostic composition comprises multiple reagents capable of identifying at least three, four, five, six, seven, eight, nine, ten, fifteen or twenty sequences or proteins selected from the group consisting of SLC37A2, FLNB, RALGPS2, ENAH, ITGA6, FNIP1, GOLGA2, ARFGAP2, TCF7L2, SLK, SCRIB, OSBPL3, COL16A1, PLAA, MAP3K7, PQLC3, GOLGA4, PRC1, MEST, UBE2K.

Certain diagnostic compositions or reagents include therefor compositions, usually probes or primer sets capable of identifying multiple of these target genes as a gene signature characteristic of the epithelial cell cancer, its prognosis or its metastasis. Certain diagnostic compositions or reagents include therefor compositions, usually probes or primer sets capable of identifying multiple of these target genes as a gene signature characteristic of tissue fibrosis. One of skill in the art given this disclosure and these identified target genes can assemble various combinations of diagnostic reagents to detect or measure expression levels of the suitable target variants.

In still other embodiments, the diagnostic composition or reagent is designed to detect or measure the ESRP1/2 splicing target variants expressed by one or multiples of the genes identified in Table 3. One of skill in the art given this disclosure and these identified target genes can assemble various combinations of diagnostic reagents to detect or measure expression levels of the suitable target variants.

TABLE 3

Summary of ESRP targets tested by RT-PCR

| Gene Symbol | Event | Genomic Coordinates | Predicted ESRP Function | PNT2 siRNA Validation | Reciprocal Change in MB231 Ectopic Expression | SEQ ID NOs of Genomic Coordinates of Col. 3 |
|---|---|---|---|---|---|---|
| FAM62A | Alt. 3'SS | chr12: 54814131-54814160 | Promotes upstream 3' splice site | Yes | No | 66 |
| CHRNA5 | Alt. 5'SS | chr15: 76669202-76670037 | Promotes downstream 5' splice site | Yes | No | 67 |
| SCRIB | Cassette exon | chr8: 144961710-144961772 | Silence | Yes | Yes | 20 |
| SLK | Cassette exon | chr10: 105,760,564-105,760,656 | Enhance | Yes | Yes | 9 |
| TRIP10 | Cassette exon | chr19: 6697040-6697207 | Enhance | Yes | No | 68 |
| ADAM15 | Cassette | chr1: 153301004-153301075 | Enhance | Yes | Yes | 69 |

TABLE 3-continued

Summary of ESRP targets tested by RT-PCR

| Gene Symbol | Event | Genomic Coordinates | Predicted ESRP Function | PNT2 siRNA Validation | Reciprocal Change in MB231 Ectopic Expression | SEQ ID NOs of Genomic Coordinates of Col. 3 |
|---|---|---|---|---|---|---|
| WNK1 | Cassette exon | chr12: 859000-859458 | Silence | No | No | 70 |
| GADD45A | Cassette exon | chr1: 67924296-67924397 | Enhance | No | No | 71 |
| LOXL2 | Cassette exon | chr8: 23,284,093-23,284,230 | Enhance | Yes | Yes | 72 |
| SCRIB | Cassette exon | chr8: 144961710-144961772 | Silence | Yes | Yes | 20 |
| SLK | Cassette exon | chr10: 105,760,564-105,760,656 | Enhance | Yes | Yes | 9 |
| MYO1B | Dual cassette exons | chr2: 191973720-191975689 | Silence | Yes | Yes | 73 |
| OGDH | Mutually exclusive | chr7: 44,653,552-44,653,893 | Promotes distal exon | Yes | No | 74 |
| SF1 | Alt 3' end Type I | chr11: 64,300,038-64,300,736 | Promotes long isoform | Yes | No | 75 |
| SF3B1 | Alt 3' end Type I | chr2: 197,991,337-197,993,726 | Promotes long isoform | Yes | No | 76 |
| GIT2 | Alt 3' end Type II | chr12: 108,869,527-108,873,965 | Promotes short isoform | Yes | Yes | 77 |
| EPB41L5 | Alt 3' end Type II | chr2: 120,574,253-120,579,718 | Promotes short isoform | Yes | Yes | 78 |
| CUL4A | Alt 3' end Type II | chr13: 112,930,781-112,936,341 | Promotes short isoform | Yes | No | 79 |
| RBM39 | Retained intron | chr3: 50112489-50112968 | Promotes splicing | No* | No | 80 |

TABLE 4

ESRP targets with published roles in cell adhesion, polarity, migration, or regulation of the actin cytoskeleton.

| | |
|---|---|
| OSBPL3 (ORP3) | oxysterol binding protein-like 3 |
| EPB41L5 | erythrocyte membrane protein band 4.1 like 5 |
| MYO1B | myosin IB |
| LAMC2 | laminin, gamma 2 |
| SCRIB | scribbled homolog (Drosophila) |
| PXN | paxillin |
| CD99 | CD99 molecule |
| KLHL5 | kelch-like 5 (Drosophila) |
| DOCK7 | dedicator of cytokinesis 7 |
| SLK | STE20-like kinase (yeast) |
| ENAH | enabled homolog (Drosophila) |
| TGFB2 | transforming growth factor, beta 2 |
| ADAM15 | ADAM metallopeptidase domain 15 |
| CASK | calcium/calmodulin-dependent serine protein kinase (MAGUK family) |
| SPTAN1 | spectrin, alpha, non-erythrocytic 1 (alpha-fodrin) |
| ITGA6 | integrin, alpha 6 |
| ITGB1 | integrin, beta 1 (fibronectin receptor) |
| ITGB3BP | integrin beta 3 binding protein |
| ITGB1BP1 | integrin beta 1 binding protein 1 |
| MACF1/ACF7 | microtubule-actin crosslinking factor 1 |
| GIT2 | G protein-coupled receptor kinase interactor 2 |
| VEGFA | vascular endothelial growth factor |
| CTNND1 | p120-catenin; catenin (cadherin-associated protein), delta 1 |
| LOXL2 | Lysyl oxidase-like 2 |
| CDH3 | cadherin 3, type 1, P-cadherin (placental) |
| FLNB | filamin B, beta (actin binding protein 278) |
| JAG2 | jagged 2 |
| FAT | FAT tumor suppressor (Drosophila) |
| PTPRM | protein tyrosine phosphatase, receptor type, M |

In another embodiment of the invention, the diagnostic reagent is immobilized on a substrate. In a further embodiment, the reagent enables detection of changes in expression in at least one of (a), (b), (c) or (d) from that of a reference expression profile, the changes correlated with the diagnosis, stage or progression of a disease selected from the group consisting of an epithelial cell cancer or carcinoma, metastasis thereof, tissue fibrosis or a disease or condition related to inappropriate splicing of a target such as FGFR2. In another embodiment, the composition is presented in a microfluidics card, chip or chamber. In another embodiment, the reagent is associated with a directly-detectable, or indirectly-detectable, label. In another embodiment, the diagnostic composition may comprise a microarray or panel of two or more the reagents capable of identifying the presence of two or more sequences of (b), (c) or (d) in a biological sample. In a further embodiment, two or more of (b), (c) or (d) form a signature diagnostic of an epithelial cell cancer or carcinoma, metastasis thereof, or tissue fibrosis.

In a further embodiment, the any of the above compositions or reagents is contained within a kit. In another embodiment, the kit contains a positive or negative control.

One embodiment of a diagnostic reagent comprises at least one polynucleotide immobilized on a substrate. The polynucleotide is a genomic probe that hybridizes to at least one splicing factor selected from ESRP1, ESRP2 or RNPC1 or suitable target variant thereof. The reagent can contain additional splicing factors or target variants useful as a genetic signature of a disease involving inappropriate FGFR2 splicing, such as tissue fibrosis or an epithelial cell cancer. In one embodiment the reagent enables detection of changes in expression in at least one splicing factor selected from ESRP1, ESRP2 and RNPC1 or target variant from that of a reference expression profile. Differences between the expression of these factors or targets in a subject that of the signature profile can indicate a diagnosis of cancer, tissue fibrosis or another related disorder. The changes correlate with the diagnosis, stage or progression of a disease or condition related to inappropriate splicing of FGFR2.

Still another diagnostic reagent or composition or kit for diagnosing the occurrence, stage or progression of a disease or condition related to inappropriate splicing of a target such as FGFR2 in a mammalian subject includes one or more PCR primer-probe sets that amplifies a polynucleotide sequence of at least one splicing factor selected from ESRP1, ESRP2 and RNPC1 or one target thereof.

The diagnostic compositions of the invention can be presented in the format of a microfluidics card, a microarray, a chip or chamber employs the PCR, RT-PCR or Q PCR techniques described above. In one aspect, such a format is a diagnostic assay using TAQMAN® Quantitative PCR low density arrays. When a biological sample from a selected subject is contacted with the primers and probes in the diagnostic composition, PCR amplification of genes in the gene expression profile from the subject permits detection of changes in expression in the splicing factor genes or targets thereof in the gene expression profile from that of a reference gene expression profile. Significant changes in the gene expression indicating a decrease in the expression level of these splicing factors or targets from that of the reference gene expression profile can correlate with a diagnosis of disease, e.g., tissue fibrosis, cancer or a particular stage of a cancer.

The selection of the particular polynucleotide sequences useful as primers or probes for the splicing factors or their targets (a)-(d) above, the length and labels used in the composition are routine determinations made by one of skill in the art in view of the teachings of which genes can form the gene expression profiles suitable for the diagnosis and prognosis of epithelial cell cancers.

Still another diagnostic reagent includes a composition or kit comprising at least one ligand that binds to an expression product of at least one mammalian splicing factor selected from ESRP1, ESRP2 and RNPC1 or one target thereof. In one embodiment the ligand is associated with a detectable marker. In another embodiment, the splicing factor is a protein and the ligand is an antibody or functional fragment thereof, such as a Fab fragment, a complementarity determining region "CDR", an scFv, among other known sequences. Such reagents are useful in immunohistochemistry diagnostic methods. Antibodies or antisera, preferably polyclonal antisera, and most preferably monoclonal antibodies, or other protein-binding ligands specific for each factor or target are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Protocols and kits for immunohistochemical analyses are well known in the art and are commercially available. In still another embodiment, the splicing factor or target is a nucleic acid sequence and the ligand is an antisense sequence or polynucleotide as discussed above.

Such diagnostic reagents and kits containing them are useful for the measurement and detection of ESRP1, ESRP2 or RCNP1 or targets thereof in the methods described herein for diagnosis/prognosis of tissue fibrosis, epithelial celltype specific cancers, and other FGFR2-related conditions. In such composition, the antibodies or peptides or nucleic acid sequences may be immobilized on suitable substrates, e.g., bound to an avidin-coated solid support, plates, sticks, or beads. Of course, other binding agents known to those of skill in the diagnostic assay art may also be employed for the same purposes. Other reagents include conventional diagnostic labels or label systems for direct or indirect labeling of the antibodies, peptides or nucleic acid sequences, with e.g., radioactive compounds, radioisotopes, such as $^{32}$P, $^{125}$I, technhicium; fluorescent or chemiluminescent compounds, such as FITC, rhodamine or luciferin; and proteins such as biotin or enzymes and enzyme co-factors, such as alkaline phosphatase, beta-glactosidase or horseradish peroxidase; and/or molecular labels such as FLAG, etc. Other elements of the label systems include substrates useful for generating the signals upon interaction with the other components of the label system, e.g., a streptavidin and horseradish peroxidase system. Any method known in the art for separately conjugating the antibody to the detectable moiety may be employed, including those methods described by Hunter et al, 1962 Nature 133:945; Pain et al 1981 J. Immunol., Meth. 40:219 and other conventional texts.

Alternatively, a diagnostic kit thus also contains miscellaneous reagents and apparatus for reading labels, e.g., certain substrates that interact with an enzymatic label to produce a color signal, etc., apparatus for taking blood samples, as well as appropriate vials and other diagnostic assay components.

C. Screening Assays For The Identification Of Useful Compounds

The splicing factors identified by the inventors may also be used in the screening and development of chemical compounds, small molecules, nucleic acid sequences, such as cDNAs, or proteins which affect the normal splicing of FGFR2 or of another enhanced target or silenced target of these splicing factors. Such compounds, which preferably mimic the activity of ESPR1/2 have utility as therapeutic drugs for the treatment of diseases related to FGFR2 or the enhanced/silenced target disruption, such as tissue fibrosis and epithelial cell cancers.

As one aspect of the invention, there is provided a method for screening a test compound or molecule to determine its impact, if any, upon splicing activity, in the production of specific FGFR2 splice variants. In one embodiment, a test compound, including small molecules, peptides or polypeptides, nucleotide sequences, such as cDNAs, are selected for testing. In one embodiment, the selected test compound is contacted or exposed to a mammalian cell expressing the splicing factor. In another embodiment, the selected test compound is contacted or exposed to a mammalian cell expressing the gene product of the target of a splicing factor, e.g., FGFR2. In a specific embodiment, the splicing factor is ESRP1, ESRP2 or RNPC1. After suitable culture conditions, e.g., 37° C. for about 48-60 hours, the effect of the compound on the expression level of the gene product is assessed by any suitable means. The effect of the compound to alter the normal expression or variant of the target, such as FGFR2, is inversely related to its impact on the expression level of the splicing factor by the cell. Where the effect is that the test compound allows maintenance of normal expression levels or increases levels of the target of the splicing factor, the test compound mimics the activity of the splicing factor. Where the effect is that the test compound increases the expression of the target, that test compound is indicated to be useful as a potential therapeutic compound in the treatment of disorders requiring maintenance of normal expression of FGFR2. Thus, that test compound may be used to treat, prevent, or reduce metastasis of carcinomas or cancers derived from epithelial cell types, and to treat, block or reduce tissue fibrosis.

Where the effect is that the compound decreases the expression level of normal target (e.g., decreasing expression level of specific FGFR2 splice variants) and/or increases expression of the alternate splice variant and/or decreases expression of the splicing factor itself, the compound is indicated to have a potential adverse effect on conditions requiring maintenance of normal expression of the target, e.g., FGFR2. Thus, that test compound may be carcinogenic or not indicated for the treatment of certain carcinomas or cancers derived from epithelial cell types, and not desired to reduce tissue fibrosis.

In another related embodiment, a method of screening a test compound involves measuring the mutagenic effect of the compound on the expression of the target gene product or of the splicing factor itself. For example, the determination of the impact of the test compound is observed where it has mutagenized the splice regulatory factor or resulted in a mutant target or alternate splice variant of a target, e.g., FGFR2. Thus, a therapeutically desirable effect of the test compound is inversely related to its mutagenic effect on the expression of the gene product by the cell. If a compound causes a mutation in the splicing factor or normal target, e.g., FGFR2, after being contacted with a cell expressing the normal target, e.g., FGFR2, it is indicated to be possibly carcinogenic or to have a potential adverse effect on conditions requiring maintenance of normal expression of the target, e.g., FGFR2.

The high throughput splicing assay used to identify compounds that change splicing events, such as the assay described in Example 1 below, may also be used to screen compounds for the ability to alter normal splicing activity of ESRP1/2. In one embodiment such an assay involves contacting in each individual well of a multi-well plate a different selected test compound (e.g., nucleotide sequence, amino acid sequence, small molecules, etc) with a mammalian cell that expresses a specific target splice variant associated with a specific condition, e.g., cancer or tissue fibrosis. In one embodiment that cell is transfected with a minigene that expresses luciferase (or another marker gene) only when the cell expresses a specific splice variant. As one example, the minigene can have the structure outlined in the examples below. After the compound has been exposed to the expressing cell under appropriate culture conditions, the level of the marker gene (or luminescence) is conventionally measured. A change in the expression of the specific target splice variant normally expressed by the cell caused by any of the test compounds is correlated with the expression or lack of expression of the marker in each well. For example, where the assay of Example 1 is utilized to screen test compounds, the maintenance or an increase in expression level of ESRP1 or ESRP2 or a normal target thereof, e.g., FGFR2, is indicative that the compound has an anti-carcinogenic effect on the epithelial cancer or tissue fibrosis. A result in which there is a decrease in expression level of the splice variant is indicative that the compound has a potential carcinogenic effect or adverse effect on tissue fibrosis.

The use of the high throughput assay of Example 1 in identifying splicing regulators also reveals the potential for this screening method to uncover a larger set of splicing regulators of diverse mammalian transcripts. While the relative merits and liabilities of an RNAi screen versus a cDNA overexpression screen have been described elsewhere, functionally redundant protein homologs or paralogs that affect the screening assay equally, as shown here, will elude detection in an arrayed RNAi screen (Rines et al., 2006). A particular advantage of the array based approach over pooled expression screening is the ability to identify multiple genes that function in a pathway or process. In addition to the ESRPs, the inventors discovered several additional splicing regulators, which while individually unable to affect endogenous FGFR2 splicing, are likely to be a part of the combinatorial code regulating this transcript. This high throughput, cell-based methodology, used to screen cDNAs or other forms of compound is highly desirable in this context.

Another aspect of the invention comprises a screening assay to determine compounds which mimic the splicing activity of ESPR1, ESPR2 or RNCP1. In one embodiment, the method comprises culturing a host cell that does not express any epithelial splicing agent (e.g., any of ESPR1, ESPR2 or RNCP1), the cell transfected with a minigene comprising a nucleic acid sequence that generates a detectable signal when the minigene is contacted with the splicing agent; culturing the host cell in the presence of a test molecule; and detecting the generation or absence of the signal in the host cell, wherein generation of a signal in the host cell indicates that the test molecule mimics the splicing activity of the splicing agent. In one embodiment, the test molecule is a chemical reagent, a protein or a nucleic acid sequence that blocks the epithelial mesenchymal transition and inhibits the metastatic progress of carcinomas or cancers derived from epithelial cell types, or inhibits the progression of tissue fibrosis. In another embodiment, the assay is a high throughput assay. In another embodiment, the detectable signal is generated by luciferase. In another embodiment of the assay, the mammalian cell expresses a nucleic acid sequence splice variant encoding a protein associated with a specific disease condition and the minigene expresses luciferase only when the cell expresses the specific splice variant. Compounds discovered to mimic the activity of the splicing factors are discussed below related to therapeutic methods and reagents.

Other conventional assays and techniques also exist for the identification and development of compounds and drugs which impact the expression or activity of a splicing factor described herein, such as methods described in publications referenced herein. Such other assay formats may be used and the assay formats are not a limitation.

D. Therapeutic Methods And Reagents

The splicing factors identified herein, desired target variants described herein or compounds determined to mimic the biological splicing activity of these factors, may also be employed as therapeutic compositions or in therapeutic methods.

1. Methods

In one embodiment, a method for suppressing metastatis of a mammalian carcinoma or cancer derived from primary epithelial cells or blocking the progression of tissue fibrosis involves delivering to the cell at least one of ESRP1 or ESRP2. In one embodiment, the delivery comprises administering a plasmid or viral vector comprising a polynucleotide encoding ESRP1 or ESRP2 or a functional fragment thereof under the control of a promoter operable in eukaryotic epithelial cells. In another embodiment, the delivery comprises administering at least one of ESRP1 or ESRP2 as a protein ectopically to the cell. In still a further embodiment, delivery occurs under conditions permitting the uptake of the ESRP1 or ESRP2 by the cell. In another embodiment, at least one of ESRP1 or ESRP2 in an amount sufficient to provide maintain epithelial identity or prevent epithelial mesenchymal transition.

In another embodiment, a method for suppressing metastasis of a mammalian carcinoma or cancer derived from primary epithelial cells or blocking the progression of tissue fibrosis comprises delivering to the cell at least one of ESRP1 or ESRP2 or a molecule that mimics the splicing activity of the ESRP1 or ESRP2. In one embodiment, the delivery comprises administering a plasmid or viral vector comprising a polynucleotide encoding ESRP1 or ESRP2 or a functional fragment thereof under the control of a promoter operable in eukaryotic epithelial cells. In another embodiment, the delivery comprises administering at least one of ESRP1 or ESRP2 of a molecule that mimics the activity of ESRP1 or ESRP2 ectopically to the cell. In another embodiment, the delivery occurs under conditions permitting the uptake of the ESRP1 or ESRP2 or the molecule by the cell. In yet another embodiment, the delivering supplies the at least one of ESRP1 or ESRP2 or the molecule in an amount sufficient to provide maintain epithelial identity or prevent epithelial mesenchymal transition.

Another aspect of the invention comprises a method for diagnosing the occurrence, stage or progression of a disease or condition related to inappropriate splicing of FGFR2 comprising measuring the level of expression of the splicing factor RNPC1 in a biological sample from a mammalian subject, wherein the expression level of the splicing factor below the level of expression of a healthy mammalian subject is evidence of the disease or condition.

2. Compositions

Thus, in one embodiment a therapeutic composition for administration to a human subject for treatment of a disease related to inappropriate splicing of a splicing factor target such as FGFR2 or for tissue fibrosis, or a epithelial cell type specific carcinoma includes a plasmid or viral vector comprising a polynucleotide encoding at least one of ESRP1, ESRP2 and RNPC1 or a desired target variant, under the control of a promoter operable in eukaryotic epithelial cells in a pharmaceutically acceptable vehicle or carrier. The selection of a suitable plasmid backbone or viral vector, of which many are well known in the art and commercially available may be done by a person of skill in the art. Examples of such vectors include recombinant adenoviral vectors, herpes simplex virus (HSV)-based vectors, adeno-associated viral (AAV) vectors, hybrid adenoviral/AAV vectors, recombinant retroviruses or lentiviruses which are constructed to carry or express a selected nucleic acid composition of interest, modified vaccinia virus Ankara (MVA), Vaccinia, Adeno-associated virus (AAV), Alphavirus etc. Retrovirus vectors that can be employed include those described in EP 0 415 731; International Patent Publication Nos. WO 90/07936; WO 94/03622; WO 93125698; and WO 93/25234; U.S. Pat. No. 5,219,740; International Patent Publication Nos. WO 93/11230 and WO 93/10218; GB Patent No. 2,200,651; and EP 0 345 242, among others. Alphavirus-based vectors may also be used as the nucleic acid molecule encoding the transgene. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and International Patent Publication Nos. WO 92/10578; WO 94/21792; WO 95/27069; WO 95/27044; and WO 95/07994.

Examples of adenoviral vectors include those described in International Patent Publication Nos. WO 94/12649; WO 93/03769; WO 93/19191; WO 94/28938; WO 95/11984 and WO 95/00655. Other particularly desirable adenoviral vectors include those derived from chimpanzee adenoviruses, such as those described in U.S. Pat. No. 6,083,716. Another viral vector is based on a parvovirus such as an adeno-associated virus (AAV). Representative examples include the AAV vectors disclosed by Srivastava in International Patent Publication No. WO 93/09239, Samulski et al., 1989 J. Virol. 63:3822-3828; Mendelson et al., 1988 Viral. 166:154-165; and Flotte et al., 1993 PNAS 90:10613-10617. Other particularly desirable AAV vectors include those based upon AAV1; see, International Patent Publication No. WO 00/28061, published May 18, 2000. Other desirable AAV vectors include those which are pseudotyped, i.e., contain a minigene composed of AAV 5' ITRS, a transgene, and AAV 3' ITRs packaged in a capsid of an AAV serotype heterologous to the AAV ITRs. Methods of producing such pseudotyped AAV vectors are described in detail in International Patent Publication No. WO 01/83692. Such selection of vector and expression system is not believed to limit this invention.

In another embodiment, in one embodiment a therapeutic composition for administration to a human subject for treatment of a disease related to inappropriate splicing of a splicing factor target such as FGFR2 or for tissue fibrosis, or a epithelial cell type specific carcinoma includes a naked DNA containing at least one of ESRP1, ESRP2 and RNPC1 or a desired target variant, under the control of a promoter operable in eukaryotic epithelial cells in a pharmaceutically acceptable vehicle or carrier.

In still another embodiment, a pharmaceutical composition for administration to a human subject for treatment of a disease related to inappropriate splicing of a target such as FGFR2 or for tissue fibrosis, or a epithelial cell type specific carcinoma includes contains an effective amount of at least one of ESRP1, ESRP2 and RNPC1 or the desired target variant in protein form in a pharmaceutically acceptable vehicle.

Another compound or compounds useful in these methods are those that inhibit the metastatic process of carcinomas or cancers derived from epithelial cell types, or inhibit the progression of tissue fibrosis. In one example, such a compound upon contact with a mammalian cell permits expression of at least one variant protein encoded by a nucleic acid sequence splice variant that is regulated by ESRP1 or ESRP2 expression levels and may be used in a composition with a pharmaceutically acceptable vehicle. In one embodiment the compound is one or more compounds selected from the group consisting of phorbol 12-myristate 13-acetate (PMA), phenylazo-3-phyridinol, podophyllotoxin, R(−)-isoproterenol (+)-bitartrate, beclomethasone ethylcarboxamido adenosine. See, e.g., Example 22 and Table 5 below. Table 5 lists compounds that activated splicing in the luciferase reporter screen using the LOPAC™ library of compounds, a group of high purity, small organic ligands. In one embodiment desirable compounds exhibit a greater than 1.75 fold-increase over the Average Median norm for each plate exclusive of the wells in which Esrp1 cDNAs were spotted as positive controls (col 1) or the Average control (DMSO) norm (col 2) of Table 5. In another embodiment, desirable compounds exhibit a greater than 1.9 fold-increase over the Average Median norm for each plate exclusive of the wells in which Esrp1 cDNAs were spotted as positive controls (col 1) or the Average control (DMSO) norm (col 2) of Table 5. In another embodiment, desirable compounds exhibit a greater than 2.0 or 2.5 fold-increase over the Average Median norm for each plate exclusive of the wells in which Esrp1 cDNAs were spotted as positive controls (col 1) or the Average control (DMSO) norm (col 2) of Table 5. In another embodiment, desirable compounds exhibit a greater than 3.5 fold-increase over the Average Median norm for each plate exclusive of the wells in which Esrp1 cDNAs were spotted as positive controls (col 1) or the Average control (DMSO) norm (col 2) of Table 5. In another embodiment, the compound is determined using the above described screening assay.

TABLE 5

LOPAC Compounds Screened for ESPR1 Activity

| Avg Med norm | Avg DMSO Norm | CATNUM | mol weight Structure | Name | Sec Name | Class | Enzyme | Action | Selectivity | Description |
|---|---|---|---|---|---|---|---|---|---|---|
| 7.032680952 | 6.87358611 | Espr1 | Espr1 | Espr1 | Espr1 | Espr1 | Espr1 | Espr1 | Espr1 | Espr1 |
| 6.591126212 | 6.406361632 | Espr1 | Espr1 | Espr1 | Espr1 | Espr1 | Espr1 | Espr1 | Espr1 | Espr1 |
| 5.65991068 | 6.104789004 | Espr1 | Espr1 | Espr1 | Espr1 | Espr1 | Espr1 | Espr1 | Espr1 | Espr1 |
| 5.272125178 | 5.684993578 | Espr1 | Espr1 | Espr1 | Espr1 | Espr1 | Espr1 | Espr1 | Espr1 | Espr1 |
| 5.026824151 | 4.935146648 | Espr1 | Espr1 | Espr1 | Espr1 | Espr1 | Espr1 | Espr1 | Espr1 | Espr1 |
| 4.915565088 | 5.29410053 | Espr1 | Espr1 | Espr1 | Espr1 | Espr1 | Espr1 | Espr1 | Espr1 | Espr1 |
| 4.879419641 | 5.212778295 | Espr1 | Espr1 | Espr1 | Espr1 | Espr1 | Espr1 | Espr1 | Espr1 | Espr1 |
| 4.683539048 | 4.509093136 | Espr1 | Espr1 | Espr1 | Espr1 | Espr1 | Espr1 | Espr1 | Espr1 | Espr1 |
| 4.304648879 | 4.636619909 | Espr1 | Espr1 | Espr1 | Espr1 | Espr1 | Espr1 | Espr1 | Espr1 | Espr1 |
| 3.896729388 | 3.792033799 | Espr1 | Espr1 | Espr1 | Espr1 | Espr1 | Espr1 | Espr1 | Espr1 | Espr1 |
| 3.825421503 | 4.121797359 | P 8139 | 616.84292 | Phorbol 12-myristate 13-acetate | PMA | Phosphorylation | Enzyme | Activator | PKC | Activates protein kinase C in vivo and in vitro; strong NO promoter; promotes expression of iNOS in cultured hepatocytes; T lymphocyte activator |
| 3.588748546 | 3.549019763 | Espr1 | Espr1 | Espr1 | Espr1 | Espr1 | Espr1 | Espr1 | Espr1 | Espr1 |
| 3.39328163 | 3.61912973 | Espr1 | Espr1 | Espr1 | Espr1 | Espr1 | Espr1 | Espr1 | Espr1 | Espr1 |
| 3.31180299 | 3.52749457 | Espr1 | Espr1 | Espr1 | Espr1 | Espr1 | Espr1 | Espr1 | Espr1 | Espr1 |
| 3.227318922 | 3.164027962 | Espr1 | Espr1 | Espr1 | Espr1 | Espr1 | Espr1 | Espr1 | Espr1 | Espr1 |
| 2.760668436 | 2.688986369 | Espr1 | Espr1 | Espr1 | Espr1 | Espr1 | Espr1 | Espr1 | Espr1 | Espr1 |
| 2.598412207 | 2.802816598 | S 9186 | 213.24097 | SIB 1757 | 6-Methyl-2-(phenylazo)-3-pyridinol | Glutamate | | Antagonist | mGluR5 | Highly selective mGlu5 metabotropic glutamate receptor antagonist |
| 2.584686163 | 2.743086853 | Espr1 | Espr1 | Espr1 | Espr1 | Espr1 | Espr1 | Espr1 | Espr1 | Espr1 |
| 2.035659347 | 1.984651029 | P 4405 | 414.41584 | Podophyllotoxin | | Cytoskeleton and ECM | | Inhibitor | | Antineoplastic glucoside; inhibitor of microtubule assembly |
| 1.995538081 | 1.94333614 | I 2760 | 361.35186 | R(−)-Isoproterenol(+)-bitartrate | | Adrenoceptor | | Agonist | beta | Sympathomimetic amine acting almost exclusively on beta adrenoceptors; bronchodilator; active enantiomer of Isoproterenol |
| 1.941646182 | 2.094814676 | P-108 | 343.34499 | N6-Phenyl-adenosine | | Adenosine | | Agonist | A1 | Potent A1 adenosine receptor agonist |
| 1.860506666 | 1.995858795 | B 0385 | 408.92643 | Beclomethasone | 9alpha-Chloro-16beta-methyl-1,4- | Hormone | | | Glucocorticoid | Anti-inflammatory glucocorticoid |

TABLE 5-continued

LOPAC Compounds Screened for ESPR1 Activity

| Avg Med norm | Avg DMSO Norm | CATNUM | mol weight Structure | Name | Sec Name | Class | Enzyme | Action | Selectivity | Description |
|---|---|---|---|---|---|---|---|---|---|---|
| | | | | | pregnadiene-11beta,17alpha,-21triol-3,20-dione | | | | | |
| 1.821987263 | 1.953058981 | B-152 | 398.42499 | N6-Benzyl-5'-N-ethyl-carbox-amido-adenosine | N6-Benzyl-NECA | Adenosine | | Agonist | A3 | Selective A3 adenosine receptor agonist |
| 1.782972743 | 1.923013117 | P-215 | 267.28691 | PD 98,059 | 2-(2-Amino-3-methoxyphenyl)-4H-1-benzopyran-4-one | Phosphorylation | Enzyme Inhibitor | | MEK2 | Specific inhibitor of the activation of mitogen-activated protein kinase kinase (MAPK K) |
| 1.714439944 | 1.674176693 | E 4642 | 219.66983 | (±)-Epinephrine hydrochloride | (±)-Adrenalin hydrochloride | Adrenoceptor | | Agonist | | Adrenoceptor agonist |
| 1.712519854 | 1.662983152 | I 5627 | 247.72401 | (±)-Isoproterenol hydrochloride | | Adrenoceptor | | Agonist | beta | Sympathomimetic amine acting almost exclusively on beta adrenoceptors; broncho dilator |
| 1.696018387 | 1.654418765 | E 4375 | 333.29768 | (−)-Epinephrine bitartrate | Adrenaline bitartrate | Adrenoceptor | | Agonist | | Endogenous hormone and neurotransmitter |
| 1.670563788 | 1.792037261 | C 6019 | 344.84719 | Clotrimazole | 1-(o-Chlorotrityl)-imidazole | K+ Channel | | Inhibitor | Ca2+-activated K+ channel | Specific inhibitor of Ca2+-activated K+ channels |
| 1.664787743 | 1.795025781 | S 0441 | 287.74848 | SB-366791 | Vanilloid receptor-1 antagonist | Vanilloid | | Antagonist | VR1 | Vanilloid receptor-1 (VR1) antagonist |
| 1.655508435 | 1.786285871 | S 8502 | 398.30028 | (−)-Scopolamine methyl bromide | Hyoscine methyl bromide | Cholinergic | | Antagonist | Muscarinic | Competitive muscarinic acetylcholine receptor antagonist |
| 1.643127846 | 1.762160022 | A 9561 | 311.77656 | 5-(N,N-hexamethylene)amiloride | | Ion Pump | | Inhibitor | Na+/H+ Antiporter | Na+/H+ antiport inhibitor |

In another embodiment, these therapeutic compositions are useful to block the epithelial to mesenchymal transition (EMT) and inhibit metastasis. In another embodiment, the composition blocks tissue fibrosis.

Still other useful compositions comprise an effective amount of a protein encoded by a nucleic acid sequence splice variant that is upregulated or downregulated by the ESRP1 or ESRP2 expression levels of a healthy mammalian subject, optionally with a pharmaceutically acceptable vehicle carrier.

Another aspect of the invention comprises composition comprising a plasmid or viral vector comprising a polynucleotide encoding at least one of ESRP1, ESRP2 and RNPC1 or encoding at least one variant protein encoded by a nucleic acid sequence splice variant that is regulated by ESRP1 or ESRP2 expression levels under the control of a promoter operable in eukaryotic epithelial cells in a pharmaceutically acceptable vehicle or carrier.

Another aspect of the invention comprises a composition comprising an effective amount of at least one of ESRP1, ESRP2 and RNPC1 in a pharmaceutically acceptable vehicle.

Another aspect of the invention comprises a composition comprising a ligand that binds to and inhibits expression of ESRP1, ESRP2 or a protein encoded by a nucleic acid sequence splice variant that is upregulated or downregulated by the ESRP1 or ESRP2 expression levels of a mammalian subject with an epithelial cell cancer, optionally with a pharmaceutically acceptable vehicle. In one embodiment, the ligand is an antisense nucleic acid sequence that binds to ESRP1, ESRP2, the regulated protein encoding sequence, or a nucleic acid sequence that expresses a protein variant that is changed by the downregulation of EPRP1 or ESRP2. In another embodiment, the ligand is a nucleic acid sequence that silences expression of a protein variant that is upregulated by the downregulation of ESRP1 or ESRP2. In another embodiment, the composition is linked to a carrier to targeted delivery agent for use in gene therapy.

As defined herein, pharmaceutically acceptable carriers suitable for use in these compositions are well known to those of skill in the art and may be readily selected by same. In one embodiment, a preferred pharmaceutical carrier contains water for injection with mannitol added for tonicity at a concentration of about 45 mg/mL. Other possible carriers include, without limitation, and depending upon pH adjustments, buffered water, buffered saline, such as 0.8% saline, phosphate buffer, 0.3% glycine, hyaluronic acid, alcoholic/aqueous solutions, emulsions or suspensions. Other conventionally employed diluents, adjuvants and excipients, may be added in accordance with conventional techniques. Such carriers can include ethanol, polyols, and suitable mixtures thereof, vegetable oils, and injectable organic esters. Buffers and pH adjusting agents may also be employed. Buffers include, without limitation, salts prepared from an organic acid or base. Representative buffers include, without limitation, organic acid salts, such as salts of citric acid, e.g., citrates, ascorbic acid, gluconic acid, carbonic acid, tartaric acid, succinic acid, acetic acid, or phthalic acid, Tris, trimethanmine hydrochloride, or phosphate buffers. Parenteral carriers can include sodium chloride solution, Ringer's dextrose, dextrose and sodium chloride, lactated Ringer's or fixed oils. Intravenous carriers can include fluid and nutrient replenishers, electrolyte replenishers, such as those based on Ringer's dextrose and the like. Preservatives and other additives such as, for example, antimicrobials, antioxidants, chelating agents, inert gases and the like may also be provided in the pharmaceutical carriers. These immunogenic compositions are not limited by the selection of the carrier. The preparation of these pharmaceutically acceptable compositions, from the above-described components, having appropriate pH isotonicity, stability and other conventional characteristics is within the skill of the art. See, e.g., texts such as Remington: The Science and Practice of Pharmacy, 20th ed, Lippincott Williams & Wilkins, publ., 2000; and The Handbook of Pharmaceutical Excipients, 4$^{th}$ edit., eds. R. C. Rothe inventors et al, APhA Publications, 2003.

As used herein, the term "effective amount" or "pharmaceutically effective amount" refers to the amount of active compound or pharmaceutical agent that elicits the biological or medicinal response in a tissue, system, animal, individual or human that is being sought by a researcher, veterinarian, medical doctor or other clinician, which includes one or more of the following: (1) preventing the disease; e.g., preventing a disease, condition or disorder in an individual that may be predisposed to the disease, condition or disorder but does not yet experience or display the pathology or symptomatology of the disease; (2) inhibiting the disease; e.g., inhibiting a disease, condition or disorder in an individual that is experiencing or displaying the pathology or symptomatology of the disease, condition or disorder (i.e., arresting or slowing further development of the pathology and/or symptomatology); and (3) ameliorating the disease; e.g., ameliorating a disease, condition or disorder in an individual that is experiencing or displaying the pathology or symptomatology of the disease, condition or disorder (i.e., reversing the pathology and/or symptomatology). For example, an effective amount," when administered to a subject to treat cancer, is sufficient to inhibit, slow, reduce, or eliminate tumor growth in a subject having cancer.

The amounts of splicing factors/desired target variants in the pharmaceutical formulations can vary widely, i.e., from less than about 0.1 mg/mL, usually at or at least about 2 mg/mL to as much as 20 mg/mL, or alternatively up to 50 mg/mL or more by weight, and will be selected primarily by fluid volumes, viscosities, etc., in accordance with the particular mode of administration selected. Dosages will also be adjusted for the severity of disease, type of disease, and physical condition of the subject as determined by a physician.

A human unit dose form of the immunogenic composition is typically included in a pharmaceutical composition that comprises a human unit dose of an acceptable carrier, preferably an aqueous carrier, and is administered in a volume of fluid that is known by those of skill in the art to be used for administration of such compositions to humans (see, e.g., Remington's Pharmaceutical Sciences, 17th Edition, A. Gennaro, Editor, Mack Publishing Co., Easton, Pa., 1985).

These compositions may be sterilized by conventional, well known sterilization techniques, such as sterile filtration for biological substances. Resulting aqueous solutions may be packaged for use as is. In certain embodiments, the aqueous solutions are lyophilized, the lyophilized preparation being combined with a sterile solution prior to administration.

Similarly as therapeutic compositions, the mode of administration for in vivo administration may be selected by one of skill in the art, and can include any suitable route. Such routes may be selected from, e.g., oral, intravenous (i.v.), respiratory (e.g., nasal or intrabronchial), infusion, parenteral (aside from i.v., such as intralesional, intraperitoneal and subcutaneous injections), intraperitoneal, transdermal (including all administration across the surface of the body and the inner linings of bodily passages including epithelial and mucosal tissues), and vaginal (including intrauterine administration). Other routes of administration are also feasible and include, without limitation, liposome-mediated delivery, topical, nasal, sublingual, uretheral, intrathecal, ocular or otic delivery, implant, rectal, or intranasal.

E. EXAMPLES OF THE INVENTION

The following examples illustrate of the compositions, and method described herein as well as experiments performed to generate the information giving rising to the embodiments of this invention. It will be readily understood that alterations or modifications, e.g., in the formulation of the components, the routes of delivery, and the dosing, can be made for reasons known to those of skill in the art.

Example 1

Identification of Novel FGFR2 Splicing Regulatory Proteins Using Luciferase-Based Minigene Reporters in a High Throughput cDNA Expression Screen To comprehensively identify the splicing factors required for FGFR2-IIIb expression, a near genome-wide, high-throughput cDNA overexpression screen was performed. Among the previously uncharacterized splicing regulators identified using this novel approach were the essential epithelial-specific FGFR2 splicing regulators.

To carry out a high throughput cDNA expression screen for FGFR2 splicing regulators, a previously described fluorescent reporter minigene was modified by substitution of a coding sequence for firefly luciferase for that of EGFP (Hovhannisyan et al., 2006; Newman et al, 2006). The following description refers to FIGS. 1A-1C.

As shown in FIGS. 1A and 1B, the PKC-neg minigene PKC-neg-40B-IF3-Luc contains an open reading frame derived from rat protein kinase C (PKC) in a 5' terminal exon. The ORF contains FGFR2 cDNA sequences from the natural start codon through the end of exon 7 fused with a cassette containing intron 7, exon IIIB, intron 8, exon IIIc, intron 9 and exon 9. This heterologous minigene also contains a 40 nt artificial cassette exon (40B) whose inclusion in spliced transcripts is required to translate the luciferase coding sequence in frame. Exon 40B is included in only 5-10% of spliced transcripts in stably transfected cells, but insertion of downstream ISEs enhances exon inclusion with a corresponding increase in luciferase activity. Exon 40B together with flanking introns separates the PKC ORF from a 3' terminal exon containing a firefly coding sequence for luciferase from the pGL4 vector, an IRES, and a puromycin resistance marker gene (Puro$^R$).

Splicing of the 40B exon maintains an ORF that yields the enzymatic marker, wherein skipping generates a frame terminating in a stop codon upstream of the luc (see FIG. 1C). When PKC-neg minigenes are stably expressed in a cell type, e.g., 293T, that expresses FGFR2-IIIc and where the FGFR2 auxiliary cis-elements from intron 8 do not promote exon inclusion in the absence of exogenous factors, an increase in luminescence results in only in the presence of a factor that promotes exon inclusion.

Insertion of an FGFR2 intron 8 fragment (Intron Fragment 3: IF3) containing ISEs that promotes splicing of FGFR2 exon IIIb similarly enhances splicing of the heterologous 40B exon in cells that express FGFR2-IIIb in an epithelial cell type-specific manner (Newman et al., 2006). However, transient transfection of cDNAs for Tia-1 or Fox-1 enhanced inclusion of the heterologous exon in 293T cells in the presence of these FGFR2 ISEs (Gerhard et al., 2004).

Using a mesenchymal 293T cell clone (which expresses predominantly FGFR2-IIIc) which and stably expresses the PKC-neg-40B-Luc minigene, a reverse transfection approach was used in 384 well format to screen the entire mammalian genome collection (MGC) collection of full length cDNAs (>14,000) available in CMV-driven pCMV-Sport6 expression vectors (Newman et al., 2006) (data not shown). Empty pCMV-Sport vector was used as a negative control and pCMV-Fox-1 vector as a positive control. Each plate is transfected in duplicate.

An automated Wellmate liquid handler (Matrix) was used to mix 0.12 μL of Mirus transfection reagent with 20 μL of serum free media and applied to each well of the plates containing 40 ng of individual cDNAs. Subsequently 293T cells stably expressing the splicing reporters are mixed with serum containing media and dispensed to each well using the WellMate apparatus. The well plates were incubated at 37° C. for about 48-60 hours. Cells were analyzed for luminescence after additional of luciferase reagents.

Because the entire population of cells in a given well is transfected with the same cDNA, even small induced changes in the readout (e.g., luminescence) can be identified. Therefore, after the data was analyzed, clones were picked, and cDNA identity was confirmed and validated.

Figure 6:
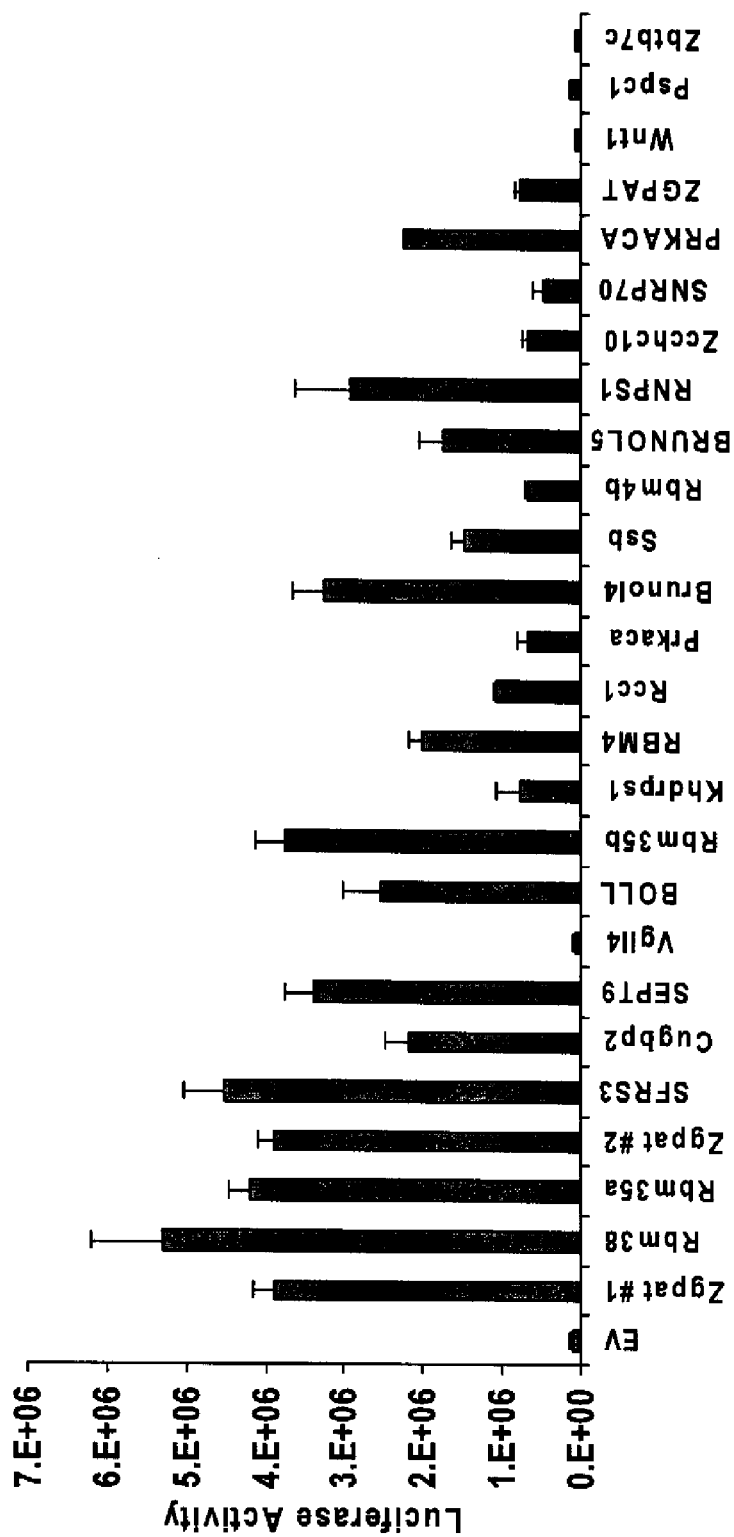
FIG. 6 is a graph showing validation of MGC screen hits in the 293T luciferase reporter cell line. The 293T cells stably expressing the luciferase reporter minigene were transiently transfected with an empty vector control, Fox1, or MGC cDNAs from Table 6. Luciferase activity was assayed and the mean values for three independent transfections are shown in the graph. Error bars denote standard deviation.

Using a six-fold increase in luciferase activity across two duplicate wells as the cutoff, a total of 28 cDNAs was identified in the primary screen, corresponding to 22 unique genes. See Table 6 below and FIG. 6. Plasmid preps for these cDNAs were prepared and confirmed by DNA sequencing. Subsequent validation steps determined that four of the hits were false positives. Nine of these hits were RNA binding proteins previously shown to regulate alternative splicing. The remaining 18 proteins were predominantly RNA binding proteins that have not previously been implicated in splicing regulation.

These remaining 18 cDNAs were independently validated to enhance luciferase activity and increase exon 40b splicing by RT-PCR confirming that the screen was specific for identification of splicing regulatory proteins. 15 of the 18 validated hits encode RNA binding proteins (RBPs) or contain consensus RNA binding domains or motifs. Eight of these RBPs have previously been shown to function in the regulation of mammalian alternative splicing. The remaining 7 RBPs and the other three proteins therefore represent novel mammalian splicing regulators. Three of these regulators were identified as RNPC1 (previously Rbm38), ESRP1 (previously Rbm35A) and ESRP2 (previously Rbm35B).

This experiment indicates the potential of this cell-based genetic screening strategy to directly uncover additional heretofore unrecognized alternative splicing regulators in mammalian cells.

TABLE 6 cDNAs that promoted a = 6-fold change in luciferase activity in the screen.

| Gene Symbol[a] | Fold Change in Screen | MGC Clone Number | RNA Binding Domain | Validated Change in Splicing |
|---|---|---|---|---|
| Zgpat (1)[b] | 30.4 | BC021513.1 | CCCH Zinc finger, G-Patch | Yes |
| Rbm38 | 26.6 | BC006687.1 | RRM | Yes |
| Esrp1 (Rbm35a) | 25.5 | BC031468.1 | RRM | Yes |
| Zgpat (2)[b] | 14.1 | BC027218.1 | CCCH Zinc finger, G-Patch | Yes |
| SFRS3[b,c] | 13.5 | BC000914.1 | RRM | Yes |
| Cugbp2[c] | 12.5 | BC026856.1 | RRM | Yes |
| SEPT9 | 12.0 | BC054004.1 |  | Yes |
| Vgll4 | 11.4 | BC048841.1 | RRM | No |
| BOLL | 11.0 | BC033674.1 | RRM | Yes |
| Sfrs3[b,c] | 10.6 | BC071196.1 | RRM | Yes[d] |
| Esrp2 (Rbm35b) | 10.6 | BC031444.1 | RRM | Yes |
| Khdrbs1[c] | 10.5 | BC002051.1 | KH Domain | Yes |
| RBM4[b,c] | 9.5 | BC032735.1 | RRM | Yes |
| Rcc1 | 9.2 | BC019807.1 |  | Yes |
| Prkaca[b] | 8.6 | BC054834.1 |  | Yes |
| Brunol4[c] | 8.4 | BC048405.1 | RRM | Yes |
| Ssb | 8.4 | BC003820.1 | RRM | Yes |
| Rbm4b[b,c] | 8.1 | BC019488.1 | RRM | Yes |
| BRUNOL5[c] | 7.8 | BC028101.1 | RRM | Yes |
| RNPS1 | 7.7 | BC108316.1 | RRM | Yes |
| Zcchc10 | 7.4 | BC025078.1 | CCHC Zinc finger | Yes |
| SNRP70[c] | 6.8 | BC001315.1 | RRM | Yes |
| PRKACA[b] | 6.8 | BC039846.1 |  | Yes |
| ZGPAT[b] | 6.4 | BC032612.1 | CCCH Zinc finger, G-Patch | Yes |
| WNT1 | 6.3 | BC005449.1 |  | No |
| Pspc1 | 6.1 | BC026772.1 | RRM | No |
| Zbtb7c | 6.1 | BC018187.1 | C2H2 Zinc finger | No |
| Zgpat (2)[b] | 6.0 | BC027218.1 | CCCH Zinc | Yes |

TABLE 6-continued cDNAs that promoted a = 6-fold change in luciferase activity in the screen.

| Gene Symbol[a] | Fold Change in Screen | MGC Clone Number | RNA Binding Domain | Validated Change in Splicing |
|---|---|---|---|---|
| | | | Finger, G-Patch | |

[a]All caps denotes a human orthologue, the others are mouse orthologues.
[b]Genes represented by multiple, independent cDNAs or transfections.
[c]Known regulators of mammalian splicing.
[d]Not tested directly, but inferred from the results obtained with human SFRS3.

Example 2

Figure 2B:
FIG. 2B is a graph indicating the percentage of exon 40B inclusion discovered as a results of the use of the minigene assay of FIG. 2A.
Figure 2C:
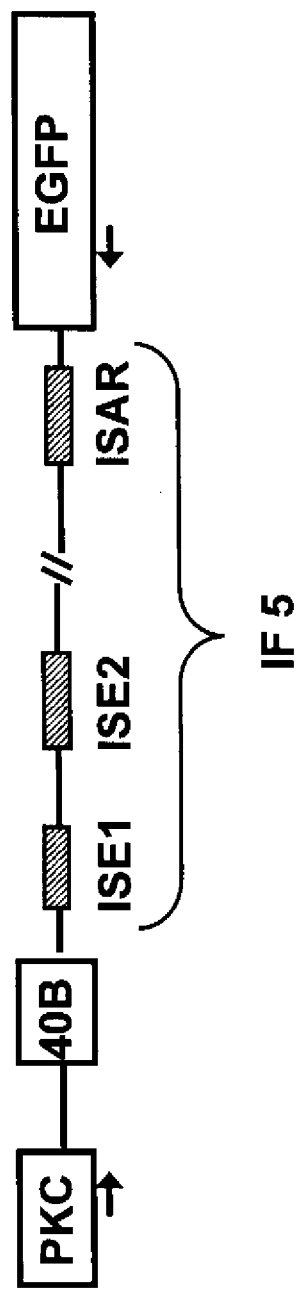
FIG. 2C is a schematic illustrating a reporter minigene expressed in the 293T-clone3 cells. The EGFP reporter has IF5, which lacks the Fox binding site and ISE/ISS-3 element, cloned downstream of exon 40B. Cells were transiently transfected with EV, Fox1, Esrp1, Esrp2, Rbm38, or Fusilli and exon inclusion was analyzed as described in FIG. 2A.
Figure 2D:
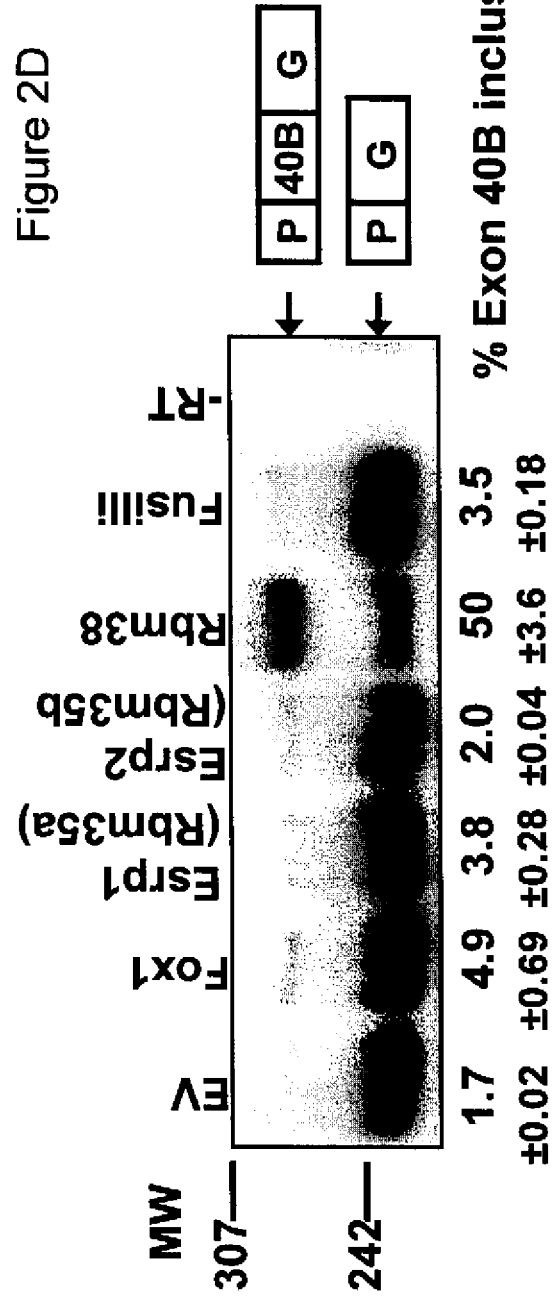
FIG. 2D is a Western gel of the EV, Fox1, Esrp1, Esrp2, Rbm38, and Fusilli expression showing average percentages of exon 40B inclusion with standard deviations compiled from three independent transfections are indicated below the gels.
Figure 2E:
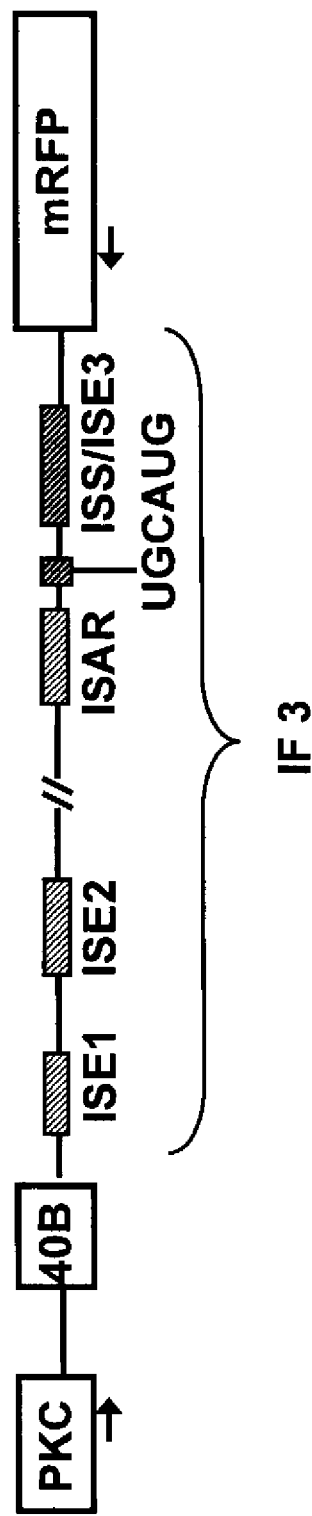
FIG. 2E is a schematic illustrating an mRFP reporter minigene expressed in the 293T-clone3 cells, which has IF3, the Fox binding site and ISE/ISS-3 element, cloned downstream of exon 40B. Cells were transiently transfected with EV, Fox1, Esrp1, Esrp2, Rbm38, or Fusilli and exon inclusion was analyzed as described in FIG. 2A.
Figure 2F:
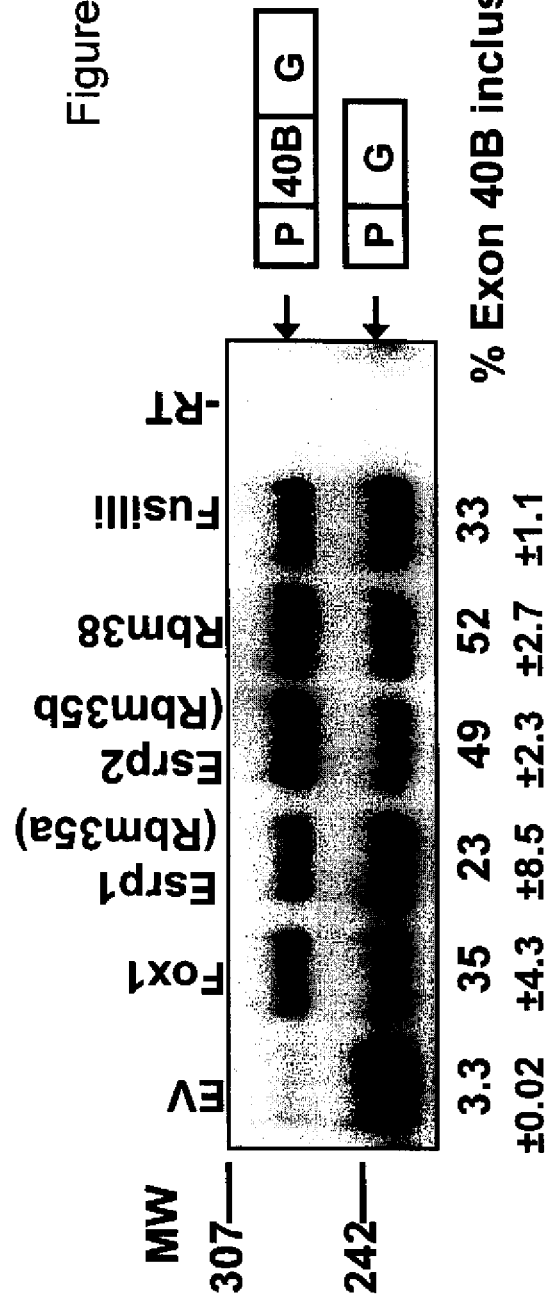
FIG. 2F is a Western gel of the EV, Fox1, Esrp1, Esrp2, Rbm38, and Fusilli expression from the transfectants of FIG. 2E, showing average percentages of exon 40B inclusion with standard deviations compiled from three independent transfections are indicated below the gels.

Seven of the 18 Splicing Regulators Identified in the Screen are Dependent on FGFR2 Intronic Cis-Elements to Enhance Exon Splicing The inventors next determined whether enhanced inclusion of exon 40B was dependent on the FGFR2 cis-elements present in IF3 using a stable 293T clone co-expressing dual color EGFP and mRFP-based minigenes (Ladd et al., 2001); see FIG. 2A. The control EGFP minigene does not contain any FGFR2 sequences, whereas the experimental mRFP minigene with FGFR2 IF3 is similar to the minigene used for the screen. Transient transfection of all 18 cDNAs into this cell line revealed that a requirement for FGFR2 IF3 to significantly enhance exon 40B inclusion was limited to seven (Rbm38, Rbm35a, Rbm35b, Cugbp2, BOLL, Brunol4 and BRUNOL5) of the 18 confirmed hits. See FIG. 2B. Three (CUGBP2, Brunol4, and BRUNOL5) of these seven genes corresponded to the Brunol/CELF family of RBPs that have previously been shown to regulate diverse alternative splicing events (Kuroyanagi et al., 2007).

The gene that displayed the greatest enhancement of splicing was RBM38 (RNPC1), which has not previously been shown to regulate splicing in mammals.

Example 3

Two Gene Paralogues, Esrp1 and Esrp2, Require ISE/ISS-3 to Enhance Exon Splicing The recent studies have focused on the role of an auxiliary cis-element called ISE/ISS-3 (Intronic Splicing Enhancer/Intronic Splicing Silencer-3), that functions specifically in epithelial cell types to coordinately enhance splicing of the upstream exon IIIb and silence the downstream exon IIIc (Hovhannisyan and Carstens, 2007). Among numerous RBPs shown to bind ISE/ISS-3 using biochemical approaches only one protein, hnRNP M, was identified that was shown to influence an FGFR2 splicing reporter (Hovhannisyan et al., 2006 and data not shown). However, hnRNP M was highly abundant in cells expressing either FGFR2 isoform, and its function was limited to the silencing of exon IIIc. Thus, identification of a critical epithelial protein that coordinately switches splicing from exon IIIc to exon IIIb through binding to ISE/ISS-3 eluded detection using standard biochemical approaches.

To determine whether any of the seven genes identified in Example 2 that were functionally dependent upon FGFR2 intronic sequences furthermore displayed a specific requirement for ISE/ISS-3 to enhance splicing, the inventors transfected the respective cDNAs in another 293T cell clone (clone 3) that also contained the same experimental mRFP-based minigene. However, the stably co-expressed control EGFP minigene in this cell line contains all of the same FGFR2 cis-elements except for the UGCAUG Fox binding motif and ISE/ISS-3 (Intron Fragment 5; IF5). Unlike IF3, IF5 cannot confer cell type-specific enhancement of a heterologous exon in cells that express FGFR2 (Hovhannisyan et al., 2006). See, FIGS. 2C, 2D, 2E and 2F.

As predicted, enhanced exon inclusion upon transient transfection of cDNAs for Fox proteins was observed only in the minigene that contained its binding site. Five of the seven cDNAs (Rbm38, Cugbp2, BOLL, Brunol4, and BRUNOL5) enhanced splicing of the heterologous exon from both minigenes, indicating that they did not require ISE/ISS-3 or the UGCAUG Fox binding motif and thus interact with sequences further upstream in the intron.

However, two cDNAs for two previously uncharacterized mammalian RBP paralogs, Rbm35a and Rbm 35b, required ISE/ISS-3 and/or the UGCAUG motif to enhance exon 40B splicing. Furthermore, a cDNA encoding the single *D. Melanogaster* ortholog for these factors, Fusilli (Fus), demonstrated the same phenotype.

To investigate whether these novel proteins bound specifically to ISE/ISS-3 the inventors performed ultraviolet crosslinking experiments with radiolabelled RNAs corresponding to the wild-type ISE/ISS-3 and a previously defined functional mutant (Ponthier et al., 2006). As a control for specificity the inventors also used an RNA previously shown to bind Fox-2 (Park et al., 2008). The RNAs were incubated with nuclear extracts from 293T cells transiently transfected with cDNAs encoding FLAG-tagged Rbm35a, Rbm35b, Fox-2, or empty Flag vector. Crosslinked bands corresponding to the predicted size of FLAG tagged Rbm35a and Rbm35b proteins were observed using the wild-type ISE/ISS-3, but not with the mutant or the unrelated Fox-1 RNA target, upon incubation with nuclear extracts transfected with these cDNAs). The same crosslinks were not observed with extracts from empty vector or Fox-2 transfected cells.

In contrast, a clearly evident crosslinked band corresponding to transfected Fox-2 was specifically observed upon incubation of the Fox-2 target RNA with extracts from Fox-2 transfected cells. The identity of the crosslinked FLAG-tagged bands was validated by immunoprecipitation of the crosslinked extracts with anti-FLAG resin. These results therefore indicate that ESRP1 and ESRP2 bind directly to ISE/ISS-3.

Example 4

Ectopic Expression of cDNAs Encoding Either ESRP1 (Rbm35a) or ESRP2 (Rbm35B) in Cells that Express FGFR2-IIIc is Sufficient to Switch Splicing of Endogenous FGFR2 Transcripts from Exon IIIc to Exon IIIb The inventors also analyzed splicing of endogenous FGFR2 in 293T cells transiently transfected with cDNAs for the subset of genes with FGFR2 intron 8 dependent function. In the initial experiments, only the cDNA for Rbm35b affected splicing of endogenous FGFR2 with a switch from nearly 100% exon IIIc splicing to between 20-50% inclusion of the epithelial IIIb exon. The inventors noted, however, that the MGC cDNA clone for Rbm35a was truncated at the 5' end and obtained a full length Rbm35a cDNA clone that was likewise sufficient to induce a similar switch in endogenous FGFR2 splicing. These results indicate that these paralogous FGFR2 splicing regulators are functionally redundant.

Figure 3A:
FIG. 3A are Western gels showing the results of transient transfection of 293T cells with ESRP2 or an empty vector and FGFR2 splicing was analyzed by RT-PCR protocol in which products are digested with Aval(A) or HincII(H), which specifically cuts exon IIIb- and exon IIIc-containing products, respectively. "U" indicates undigested PCR products.
Figure 3B:
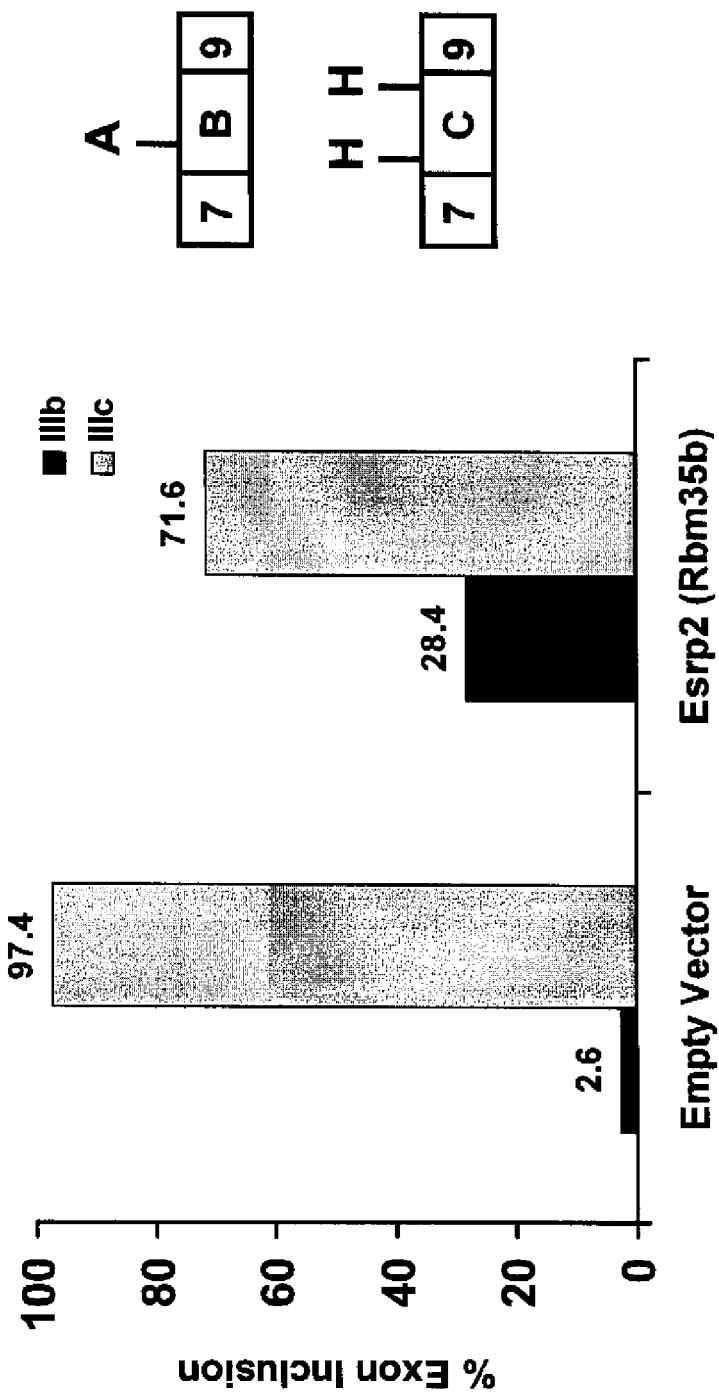
FIG. 3B is a graph showing % exon inclusion in these cells.
Figure 5A:
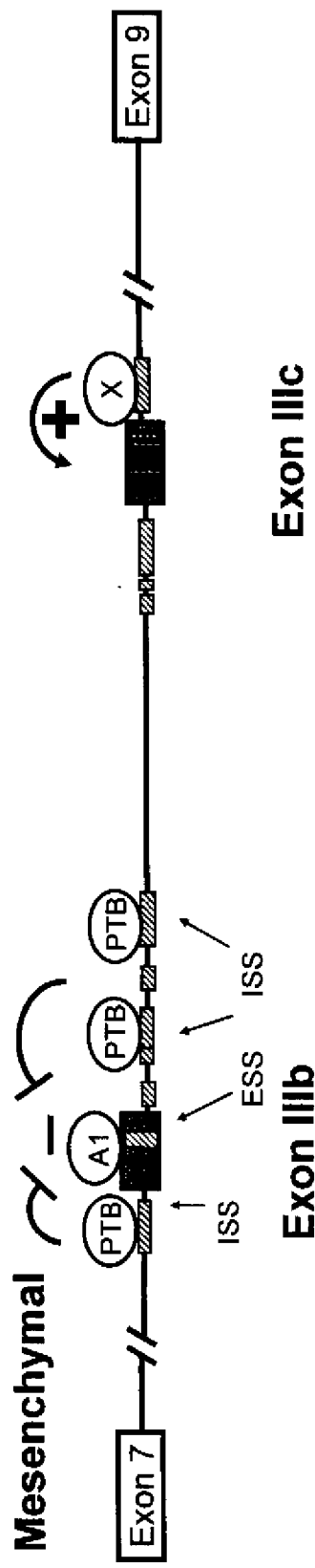
FIG. 5A is a model for the mechanism of FGFR2 cell type-specific splicing, specifically showing that combinatorial control by ubiquitous regulatory proteins establishes a "default" splicing pathway that in mesenchymal cells silences exon IIIb and promotes inclusion of exon IIIc. Cross-hatched boxes indicate known FGFR2 auxiliary cis-elements. PTB=polypyrimidine tract binding protein. A1=hnRNPA1. X indicates an unknown factor that binds an ISE downstream of exon We.
Figure 5B:
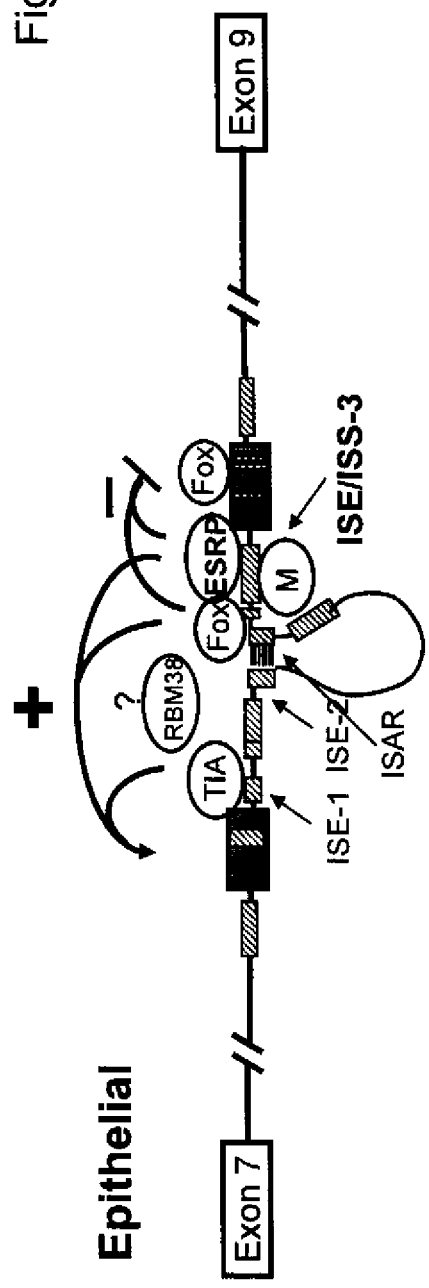
FIG. 5B is another model showing that in epithelial cells, the ESRPs collaborate with other regulatory proteins to activate exon IIIb splicing and silence exon IIIc splicing. Potential interactions between these proteins are indicated by double arrows and question marks. M represents human RNP M. TIA represents Tia1 or TiaR. Fox represents Fox family members. A base pairing interaction between two complementary sequences in the intron (ISE2 and ISAR) likely serves to position ESRP1 more closely to exon IIIb where it can act in conjunction with other factors (such as RBM38 and Tia1) to activate splicing (Muh et al., 2002). Proteins other than the ESRPs shown binding to the FGFR2 transcripts only mesenchymal oripithelial cells are expressed in both cell types and may be bound to the cognate elements in either cell type.

Establishment of cell lines stably expressing either Rbm35a or Rbm35b was complicated by apparent selection against their continued expression. Therefore, to investigate the effects of more prolonged expression of these cDNAs in 293T and other cells that express the mesenchymal FGFR2-IIIc isoforms, the inventors used a retroviral expression system. Analysis of endogenous FGFR2 splicing one week after transduction of 293T cells with vectors encoding these cDNAs demonstrated a more substantial switch in splicing from less than 5% exon IIIb inclusion with empty expression vector to 50% with the cDNA encoding ESRP1/Rbm35a and 66% with the cDNA encoding ESRP2/Rbm35b. The ability of either factor to switch splicing from exon IIIc to IIIb was also shown in three other FGFR2-IIIc expressing cell lines, including the rat AT3 prostate cancer cell line. At the same time the inventors also observed that transduction with virus encoding a cDNA for *D. melanogaster* caused a similar, or even higher degree of switching of endogenous FGFR2 splicing, further indicating the conserved function of this gene family. See, e.g., FIGS. 3A and 3B.

Example 5

ESRP1 (Rbm35a) and ESRP2 (Rbm35b) are Epithelial Cell Type-Specific Splicing Regulatory Proteins In view of the discovery of the induction of a robust switch in FGFR2 splicing from the mesenchymal to epithelial pathway by Rbm35a and Rbm35b, the inventors examined whether these two proteins were epithelial cell type-specific factors whose expression is limited to cells and cell lines that express FGFR2-IIIb. The inventors analyzed Rbm35a and Rbm35b mRNA expression in a panel of cell lines commonly used in the lab by RT-PCR. The inventors discovered that both proteins were expressed in FGFR2-IIIb expressing cell lines, but not in those expressing FGFR2-IIIc (PNT2, AT3, DT3, 293T, HMLE).

Figure 7:
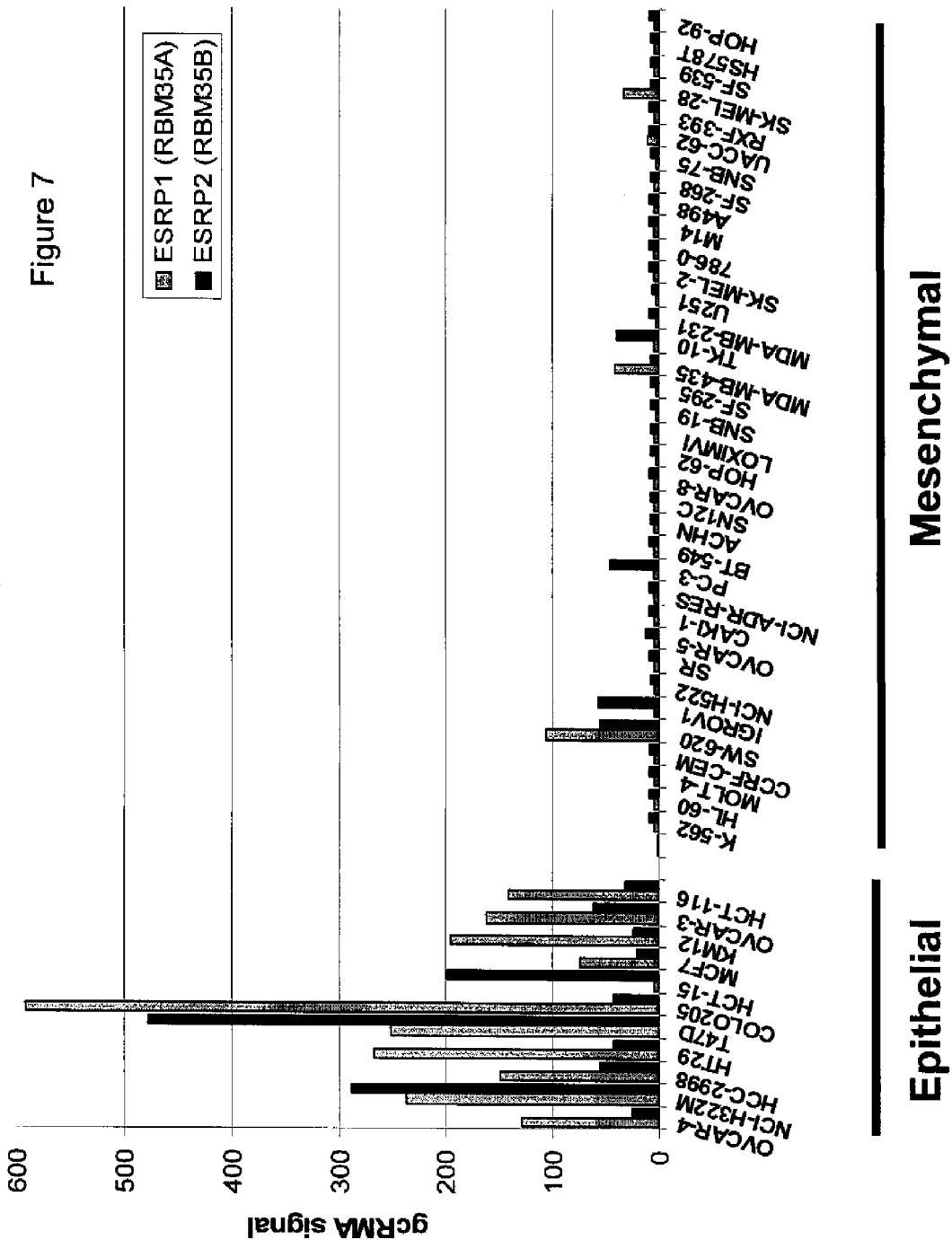
FIG. 7 is a graph showing that ESRP1 and ESRP2 expression is specifically observed in NCI60 cell lines classified as epithelial. Microarray data for ESRP1 and ESRP2 mRNA expression in cell lines that were classified as epithelial or mesenchymal based on the E-Cadherin/Vimentin ratio as described (Park et al., 2008) is shown. The gene profiling dataset of the NCI60 cell using the Affymetrix U133A and U133B was performed as described and was downloaded from the Cellminer website http://discover.nci.nih.gov/cellminer (Shankavaram et al., 2007). Shown are gcRMA normalized signal intensity in each cell line using probesets 219121_s_at (ESRP1/RBM35A) and 219395_at (ESRP2/RBM35B). The colon carcinoma cell line SW620 was the only "mesenchymal" cell line with significant expression of both ESRP1 and ESRP2. However, this classification displayed very low protein levels for both E-Cadherin and Vimentin and furthermore showed significant expression of epithelial-specific miR-200 family members (Park et al., 2008).

The inventors further confirmed that these splicing factors are epithelial specific using a microarray database that examined mRNA expression across the NCI60 panel of cell lines used in a study showing that endogenous miRNA-200 family members are powerful epithelial cell markers whose expression closely correlate with E-Cadherin/Vimentin ratios (Park et al., 2008). All cell lines classified as "epithelial" based on E-cadherin/vimentin ratio that also expressed the miR-200 expressed substantially higher levels of RBM35A or RBM35B (usually both), than cells classified as "mesenchymal," most of which displayed nominal expression (Shankavaram et al., 2007). See FIG. 7.

To provide further verification that expression of these proteins correlates directly with expression of FGFR2-IIIb, the inventors performed qRT-PCR with RNAs from an additional subset of cell lines, including several from the NCI60 collection, to independently validate that expression of RBM35A and/or RBM35B correlated with FGFR2-IIIb expression. FGFR2 splice variant analysis has previously been shown for several of these lines and included DU-145, which demonstrates predominant FGFR2-IIIc, but some FGFR2-IIIb, expression (Carstens et al., 1997; Cha et al., 2008; Luqmani et al., 1996). Consistent with this observation, DU-145 was classified as being indeterminate for epithelial or mesenchymal type based on co-expression of E-cadherin and vimentin (Park et al., 2008).

This analysis confirmed that significant expression of RBM35A or RBM35B was limited to those cells that express exclusively FGFR2-IIIb, with modest expression of RBM35B in DU-145.

To further test whether expression of RBM35A or RBM35B is predictive of the FGFR2 splicing pattern, the inventors carried out splice variant analysis using RNA from two ovarian cancer cell lines, Ovcar3 and Ovcar5, for which the FGFR2 splicing pattern was not known. As predicted, Ovcar 3, which expressed relatively high amounts of both proteins expressed FGFR2-IIIb, whereas Ovcar5, which did not, expressed FGFR2-IIIc. Thus, while expression of these FGFR2 splice variants are not known for most of the NC160 cell lines, a direct correlation between Rbm35a and/or Rbm35b and expression of FGFR2-IIIb is supported by all examples in which the inventors or others have determined FGFR2 isoform expression.

The inventors anticipate that testing of additional cell lines with high levels of these factors (e.g. Colo205, HCC-2998) will reveal exclusive FGFR2-IIIb expression.

The epithelial specificity of these proteins is further supported by data in which their mRNAs have been identified in vivo. For example, distinct epithelial-specific expression of Rbm35a in epithelia overlying the facial skeleton was shown using in situ analysis and the same study supported an epithelial-specific expression pattern for Rbm35b as well (McKee et al., 2005). Furthermore, Rbm35a was shown to be a member of a group of "endodermal signature genes" during early mouse embryogenesis (Sherwood et al., 2007). By contrast, expression of both genes is turned off during induced differentiation of human embryonic stem cells into mesenchymal stem cells (Barberi et al., 2005).

Collectively, these data support that these factors constitute evolutionarily conserved epithelial cell type-specific splicing proteins.

Example 6

RNA Interference Demonstrates that the ESRPs are Required for Expression of the FGFR2-IIIb Splice Variant in Epithelial Cell Types To provide proof that expression of at least one of these factors is required for expression of FGFR2-IIIb, the inventors performed RNA interference in cells that express this isoform. Given functional redundancy in the ectopic expression experiments the inventors first determined the effect of knockdown of either factor alone as well as combined knockdown using siRNAs in the human prostate cancer PNT2 cell line (Cussenot et al., 1991). Although knockdown with 2 effective siRNAs against ESRP1 alone caused a partial switch from exon IIIb to exon IIIc splicing, 2 separate combinations of effective siRNAs against both ESRP1 and ESRP2 caused a nearly complete switch from exon IIIb to exon IIIc splicing in the endogenous FGFR2 transcript.

The inventors also performed the same siRNA mediated knockdown in a human mammary epithelial cell line, HMLE, and also observed a switch from exon IIIb to exon IIIc splicing although the switch was less complete, most likely due to decreased efficiency of RNAi in these cells. HMLE cells were transfected with siRNAs against GFP as a control or against ESRP1 and ESRP2 in tandem. FGFR2 splicing was analyzed by RT-PCR. Average exon IIIb inclusion with standard deviations was compiled from three independent transfections. For the siGFP control the % IIIb inclusion was 97+/−0.06; for the tandem experiment, the % IIIb inclusion was 56+/−0.38 (gel not shown). Although knockdown by independent siRNAs against ESRP1 and ESRP2 constitutes strong evidence that the switch in splicing is due to knockdown of these factors rather than off target effects, the inventors further carried out a "rescue" with mouse cDNAs for ESRP1 and ESRP2 that were immune to knockdown by these human siRNAs. PNT2 cell were transduced with empty retroviral vector or vector containing the cDNAs for mouse Esrp1 or Esrp2. After 9 days, stable cells were transfected with siRNAs against human ESRP1 and ESRP2 and RNA was harvested for FGFR2 isoform analysis. In cells transduced with empty vector, the inventors again observed a nearly complete switch in FGFR2 splicing. In contrast, cells expressing RNAi resistant cDNAs for either Esrp1 or Esrp2 maintained predominant FGFR2-IIIb expression.

These data provide definitive evidence that these proteins are essential for FGFR2-IIIb expression. These data therefore support that these paralogous gene products are important regulators of this developmentally essential alternative splicing choice.

Example 7

The ESRP Family of Splicing Regulators is Evolutionarily Conserved and Developmentally Essential RRM Domain Proteins The mouse ESRPs and orthologs in humans, *D. melanogaster*, and *C. elegans* contain three RNA Recognition Motifs (RRMs) that constitute the only readily identifiable protein domain common to all orthologs; most phylogenetic sequence conservation is present in these domains. The sequences of the three human RRMs can be found in SEQ ID NOs: 1-3. Clustal W (DNASTAR) alignment of the three ESRP RRM domains was performed using the accession numbers of the sequences as follows: NP_918944 (Mm Esrp1), NP_789808 (mM Esrp2), NP_060167 (Hs ESRP1), NP_524691 (Dm Fusilli), NP_495960 (Ce Sym-2) XP_418338 (Gg Esrp1), NP_001025737 (Gg Esrp2) (data not shown). The boundaries of the RRM domains were defined by the SMART computer system (sequence motif analysis and retrieval tool) (http://smart.embl-heidelberg.de/). The highest sequence identity is observed within RRM1. *Drosophila* fusilli was originally identified in a screen for dominant maternal enhancers of a dorsalizing mutation in the cactus gene and a potential splicing regulatory function was speculated based on homology with the mammalian splicing regulators hnRNP F and H (Wakabayashi-Ito et al., 2001). Fusilli expression was required in ovarian follicle cells for dorsal-ventral patterning and subsequently was noted to be specifically expressed in the epithelium of the stomodeum and proctodeum in stage 9 embryos. These data, together with the observation that Fusilli can functionally substitute for mammalian Esrps, make it evident that the functions of these orthologs as splicing regulators as well as their epithelial-specific expression are highly conserved evolutionarily. This conserved function as a splicing regulator extends to *C. Elegans* sym-2 (Synthetic Lethal with Mec-8), which was previously suspected based on developmental redundancy with the splicing regulator Mec-8, was recently confirmed to regulate splicing of a number of transcripts during several different stages of worm development (Barberan-Soler and Zahler, 2008).

Example 8

Downregulation of ESRP Expression Coincides with a Switch from FGFR2-IIIb to FGFR2-IIIc in the EMT A loss of FGFR2-IIIb is known to occur during the EMT. The inventors investigated whether loss of ESRP is associated with the EMT. The inventors initially analyzed FGFR2 isoform expression and ESRP expression in an immortalized human mammary epithelial cell line, HMLE, induced to undergo EMT in response to the transcription factor Twist1 (Yang et al., 2004). Twist is one of several EMT inducing transcription factors that have been shown to correlate with tumor invasion and metastasis and whose expression has been associated with a poorer prognosis for several types of carcinoma. Analysis of FGFR2 splicing following transduction with a retrovirus containing the Twist cDNA showed that a partial switch from predominant FGFR2-IIIb to IIIc occurred that coincided with a morphological EMT, decrease in established epithelial markers, and increase in mesenchymal markers. Consistent with their previously observed epithelial-specific expression, the inventors detected both ESRP1 and ESRP2 in control HMLE cells, but loss of mRNA for both factors following Twist induced EMT as determined by qRT-PCR. See FIGS. 4A-4C. Interestingly, knockdown of E-Cadherin by RNAi was recently shown to induce an EMT in the same cell line and microarray analysis by these authors likewise revealed a significant downregulation of both ESRP1 and ESRP2 (Onder et al., 2008). Significantly, a reduction in total FGFR2 expression was also observed which was also apparent in the analysis of FGFR2 isoform expression following Twist-induced EMT.

These findings are consistent with previous studies which have shown that changes consistent with an EMT are accompanied by a switch from FGFR2-IIIb to FGFR2-IIIc as well as an overall transcriptional downregulation of FGFR2 (Feng et al., 1997). The epithelial specificity of the ESRPs and these results implied that they constitute an important component of an epithelial cell type-specific signature. Also, the expression level of the ESRPs has an inverse correlation with mesenchymal markers in certain tumors, including those associated with a poorer outcome.

To examine this further the inventors generated a list of a number of previously published epithelial and mesenchymal markers and performed gene cluster analysis on the microarray data set derived from cells that underwent an EMT upon E-cadherin knockdown. The inventors also performed a similar analysis on microarray data from a breast cancer model in which cells selected for invasive properties in vitro produced invasive, poorly differentiated tumors in SCID mice (Huang et al. 2007). These invasive cells and the tumors they produced were likewise shown to display features consistent with an EMT. In both analyses ESRP1 and ESRP2 clustered with epithelial markers and showed similar down regulation during the EMT that coincided with upregulation of mesenchymal markers, including Twist.

Thus, a decrease in ESRP expression is predicted to be a general feature associated with the EMT associated with metastasis and tissue fibrosis. Furthermore, the inventors anticipate that post-transcriptional targets of these proteins contribute to epithelial cell differentiation. Therefore the patterns of alternative splicing they control are themselves a component of such an epithelial expression program and signature.

Example 9

Viral Transduction of cDNAs Encoding ESRP1 or ESRP2 can Prevent and Reverse Twist Induced EMT in Human Mammary Epithelial Cells To determine whether downregulation of ESRP expression is a requirement for cells to acquire a mesenchymal phenotype, the inventors transduced viral vectors expressing cDNAs encoding ESRP1 and ESRP2 in Twist-transformed HMLE cells that had undergone a clear morphologic EMT. In these preliminary experiments, the inventors found that ESRP1 caused these cells to revert to a more epithelial morphology with a cobblestone appearance, whereas the control EGFP transduced cells maintained a more fibroblastic appearance. However, attempts to transduce HMLE-Twist cells with a cDNA encoding ESRP subsequently resulted in complete cell death. These experiments were carried out using dual selection to maintain expression of both ESRP1 and Twist, suggesting that the reversion to an epithelial phenotype was due at least in part to downstream events controlled by these factors and not merely a loss of Twist expression.

Furthermore, the inventors also performed the same experiment in reverse and tested whether HMLE cells transduced with ESRP1 or ESRP2 could prevent Twist induced EMT. The control transduction Twist was able to induce a morphological EMT, but maintenance of an epithelial phenotype as well as epithelial markers and lack of mesenchymal markers was seen in cells already expressing ESRP1 or ESRP2. These results therefore provide further evidence that expression of at least one of these factors controls a number of cellular processes that prevent an EMT. Thus, expression of these proteins is essential in the prevention of metastasis and tissue fibrosis.

As demonstrated by the examples above, the inventors have identified two novel epithelial cell type-specific splicing regulatory protein paralogs that are unequivocally required for the expression of the epithelial FGFR2-IIIb splice variant. In addition to a complete switch in splicing from exon IIIb to exon IIIc by knockdown of ESRP1 and ESRP2 in an epithelial-type cell line, the inventors also demonstrated a robust switch from exon IIIc to exon IIIb when ectopically introduced into cells that express FGFR2-IIIc. Among the FGFR2 splicing factors described to date, these proteins constitute the most essential master switch that regulates the splicing of this developmentally essential alternative splicing event.

The inventors are not aware of a previous example in which ectopic introduction of a single factor into a cell line where the factor is not expressed is sufficient to switch splicing of an endogenous target to the degree seen here.

These results with the ESRPs demonstrate that a single protein is sufficient to shift the balance of these factors towards an epithelial cell type-specific pattern of splicing. The switch from FGFR2-IIIb to the mesenchymal FGFR2-IIIc isoform in through depletion of the ESRPs alone indicates suggests that exon IIIc splicing can indeed be considered a "default" splicing pathway that does not require the expression of mesenchymal-specific factors nor a specific ratio of combinatorial regulators. However, such a default pathway does not merely arise from the relative strength of the splice sites flanking the competing exons, but rather reflects the additional contribution of an underlying combinatorial layer of auxiliary cis-elements and the factors that bind them (Carstens et al., 1998; Carstens et al., 2000). The function of the ESRP proteins, however, can override this layer and, through interactions with some of these ubiquitous factors, shift splicing towards the epithelial pathway. It is noted, however, that the ESRPs do not induce a complete splicing switch in mesenchymal cell types; an observation that supports a combinatorial effect of splicing regulators in mesenchymal cells that favors exon IIIc inclusion and IIIb silencing.

The previous association of a switch from FGFR2-IIIb to FGFR2-IIIc during the EMT led the inventors to consider whether a loss of ESRP1 and/or ESRP2 might accompany this process (Savagner et al., 1994). Such an association would be consistent with a proposed role of FGFR2-IIIb as a tumor suppressor and further implicate these epithelial splicing proteins themselves as tumor suppressors via regulation of FGFR2 splicing as well as in the regulation of other post-transcriptional targets (Ricol et al., 1999). The previous studies have largely constituted use of cell lines from the Dunning prostate cancer model in which a switch from FGFR2-IIIb to IIIc accompanies the progression from androgen dependent to independent tumors (Yan et al., 1993). Such findings also reflect a reversal of normal development process in which signaling via FGFR2 is required for the establishment of homeostatic control of prostatic epithelial cells (Lin et al., 2007). Similar observations were made in a bladder cancer model associated with an EMT and recently a switch from FGFR2-IIIb to FGFR2-IIIc was also shown to correlate with invasiveness and an associated EMT in breast cancer cell lines (Cha et al., 2008). However, the ability of FGFR2-IIIb to function as a tumor suppressor is context dependent as in some settings dysregulated signaling through this receptor can promote cancer progression (Itoh et al., 1994; Moffa and Ethier, 2007).

By virtue of promoting an epithelial-specific expression program that extends beyond FGFR2, the inventors hypothesize a more general function of the ESRPs as potential tumor suppressors. The identification of bi-allelic mutations in ESRP1 (RBM35A) in several colon cancer cell lines with microsatellite instability suggest that mutation of these factors may indeed be one mechanism by which their loss can be implicated in cancer progression (Ivanov et al. 2007) However, as a part of an epithelial cell type-specific expression program that is lost during the EMT, a loss of expression may more commonly occur in the absence of mutation, but rather as reflecting changes in cellular plasticity that represent aberrant reversal of normal developmental changes in gene expression programs. A number of studies suggest that upregulation of mesenchymal transcription factors such as Twist or Snail are associated with tumor invasion and metastasis in experimental cancer models and associated with a worse prognosis when present in patient tumor specimens is associated with an cancer progression and metastasis (Blanco et al., 2002; Cano et al., 2000; Moody et al. 2005; Yang et al., 2004).

The current data support the role of ESRPs as markers of primary tumors with less metastatic potential and a more favorable prognosis. In addition to serving as a novel epithelial cell marker, these factors are further capable of preventing or reversing the EMT induced by Twist, thereby suggesting that they represent excellent targets for future therapies directed towards maintaining or restoring their expression. However, the ability of the ESRPs to induce an EMT also suggests that they are likely to be mediators of this process in established metastases in which case their expression may no longer be favorable.

Experiments to determine whether ectopic introduction of the ESRPs into invasive tumor cell types can prevent tumor metastases in animal cancer models are being conducted. Finally there are several interesting parallels between the identification of ESRP and the recent identification of the miR-200 microRNAs that similarly enforce an epithelial phenotype and an ability to induce the EMT (Gregory et al., 2008; Park et al., 2008). These collective findings providing clear evidence of the important role of coordinated post-transcriptional regulation as a critical contributor to cellular differentiation, in this case at two separate steps in the RNA life cycle by epithelial specific regulators.

The findings also represent the first example of a splicing regulatory protein that is a likely tumor suppressor and/or whose expression is lost during cancer progression and metastasis via the EMT. These data therefore add an important addition to the evidence that alterations in alternative splicing can play an important role in the development and progression of cancer. Identification of additional splicing events regulated by ESRP may thus characterize a splicing signature that will have clinical utility as well as identify additional transcript variants that play coordinated roles in either cancer progression or prevention.

Example 10

The ESRPs Regulate Splicing of CD44, CTNND1, and ENAH

The profound switch in endogenous FGFR2 splicing from the epithelial to mesenchymal isoform upon depletion of ESRP1 and ESRP2 suggested that these cell-type-specific factors might regulate additional epithelial-specific transcript variants. Inclusion of several "variable" exons of CD44 transcripts, including exons 8-10 (V8-V10), has been shown to be epithelial specific (Ponta et al., 2003). Depletion of ESRP1 and ESRP2 in PNT2 cells resulted in a significant decrease in the inclusion of CD44 exons 8-10 and increase in the standard isoform (CD44s) in which all of the variable exons are skipped (data not shown). Delta catenin (CTNND1), also known as p120-Catenin, expresses mesenchymal specific splice variants that contain alternative exons 2 and 3 (Keirsebilck et al., 1998). Skipping of these exons in epithelial cells results in a shorter protein isoform that initiates translation in exon 5. Expression of the mesenchymal p120-Catenin isoform is induced during the epithelial-to-mesenchymal transition (EMT) (Ohkubo and Ozawa, 2004). Knockdown of ESRP1 and ESRP2 in PNT2 cells also induced expression of the mesenchymal isoform of p120-Catenin (data not shown). ENAH contains an alternative exon 11a that is predominantly included in epithelial cell lines and skipped in mesenchymal cells (Pino et al., 2008). Knockdown of ESRP1 and ESRP2 led to a significant decrease in ENAH exon 11a inclusion (data not shown).

These three examples of additional targets of the ESRPs suggest that they regulate a larger number of epithelial versus mesenchymal splice variants. Furthermore, they illustrate examples of regulated targets which can promote epithelial-specific exons (CD44 and ENAH), silence mesenchymal exons (CTNND1), or both (FGFR2). Because the proteins encoded by these gene transcripts have well documented rolls in the EMT, the inventors sought to further expand the list of alternative splicing events under the regulation of the ESRPs. Additional gene transcripts that are regulated by these proteins similarly play important roles in epithelial to mesenchymal transitions during development as well as pathophysiologic conditions such as cancer metastasis and tissue fibrosis.

Example 11

An Approach Using siRNA-Mediated Depletion and Exon Microarrays to Identify Splicing Events Regulated by ESRP1 and ESRP2

The inventors previously demonstrated that depletion of ESRP1 and ESRP2 from the human prostatic epithelial cell line PNT2 is sufficient to robustly alter the epithelial splicing pattern of four gene transcripts towards the mesenchymal splicing pattern. The inventors therefore made use of this experimental system to carry out a near genome-wide based approach to identify a broader set of splicing events regulated by the ESRPs. Combined depletion of ESRP1 and ESRP2 in PNT2 cells was carried out with siRNAs against each transcript or with siRNAs against green fluorescent protein (GFP) as a control. Each condition was performed in four biological replicates and total RNA, each processed and prepared separately, was converted into labeled cDNA for hybridization to the Affymetrix Human Exon Array 1.0 ST Microarray (FIG. 8A). The efficacy of siRNA-mediated knockdown of ESRP1 and ESRP2 was demonstrated by real-time RT-PCR (FIG. 8B). Because there are presently no suitable antibodies to specifically detect endogenous ESRP protein, the inventors were unable to verify protein depletion by immunoblotting. However, the inventors were able to demonstrate that ESRP1 and ESRP2 were functionally depleted by showing a nearly complete splicing switch from use of the mutually exclusive epithelial IIIb exon, to the mesenchymal IIIc exon in the FGFR2 transcript in all four replicates of ESRP knockdown compared to the control knockdowns (data not shown). Furthermore, the inventors previously validated the specificity of this approach as being due to protein depletion by showing that the epithelial splicing pattern could be rescued by expression of a mouse Esrp1 protein from an RNAi resistant cDNA.

Example 12

Exon Array Analysis Identifies Many Novel Splicing Targets of ESRP1 and ESRP2

In order to identify novel ESRP regulated exons and alternative splicing events the MADS tool was used to identify probe sets that were differentially expressed between the two conditions, subtracting out probe set differences that were the result of differences in overall transcript abundance. The resulting probe sets were ranked according to their MADS p-value and the top 500 differentially expressed probe sets were selected for further analysis and validations. The inventors first manually examined all probe sets using the UCSC genome browser and discarded any probe sets that did not correspond to annotated alternative splicing events as supported by mRNA or EST evidence. Examples of alternative promoters, including cases in which the exon array data could not distinguish between alternative promoters and true alternative splicing events, were discarded. For the remaining probe sets, graphical output from the MADS algorithm as well as the Gene View of all filtered probe sets in Partek Genomics Suite were analyzed. Cases in which neither analysis supported an interpretation of a true splicing change were also discarded. This assessment included a somewhat subjective interpretation of differential probe set signal, determination whether probe set differences were more consistent with overall transcript differences, and a general analysis of the overall pattern of probe set signals. Such an assessment thus also included, in some cases, an assessment as to whether reciprocal changes in several transcripts probe sets also supported differential splicing. For example, several cases of mutually exclusive exons or alternative 3' ends in which opposite changes in probe set signal were supportive of alternative splicing events were included in the final set of high confidence alternative splicing events. While some of this assessment necessarily was partly subjective, only examples in which the inventors had high confidence that the alternative splicing events were indeed regulated by the ESRPs in this experiment were included. Some of the discarded probe sets may correspond to novel, or poorly annotated examples of alternatively spliced exons. However, most of the discarded probes were present in intronic regions, the majority of which did not represent bona fide alternative splicing events and which would complicate analysis. The validation rate from the limited number of validated events strongly suggests that most of these values are true positives.

After manual annotation of the top 500 MADS probe sets and deletion of poorly supported alternative events, 148 alternative splicing events were identified from 171 probe sets, in a total of 134 different genes (data not shown). This list included detection of ESRP-regulated alternative splicing events that the inventors previously demonstrated in the CD44, CTNND1, and ENAH transcripts described in Example 10. In the case of CD44, probe sets corresponding to tandem variable exons 2, 4, 9, 5, and 7 ranked $21^{st}$, $26^{th}$, $100^{th}$, $101^{st}$, and $122^{nd}$, respectively. For CTNND1 (p120-catenin), a probe set for alternative exon 2 ranked $139^{th}$. The ENAH alternative cassette exon 11a ranked $206^{th}$ (data not shown). Probe sets corresponding to exons IIIb and IIIc of FGFR2 were filtered from the analysis because the overall transcript level of FGFR2 did not pass the expression threshold, and hence, did not appear in the list of top 500 probe sets. Nonetheless, the p-values associated with both of these mutually exclusive exons likewise strongly supported differential splicing of these exons as shown by RT-PCR.

Figure 9:
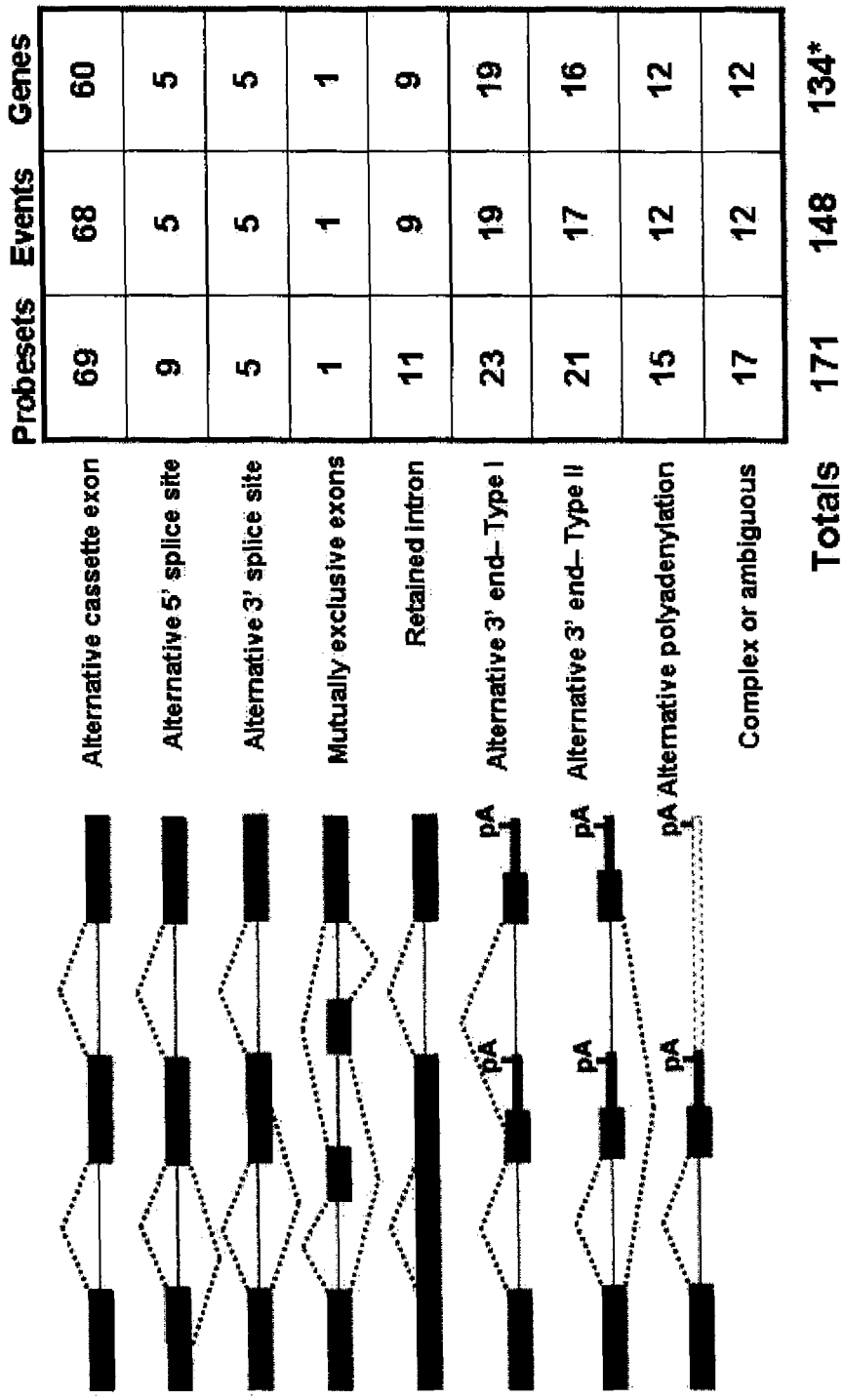
FIG. 9 is a chart illustrating the numerous novel alternative splicing targets representing all known types of alternative splicing which were identified among the high confidence set of genes identified using MADS analysis of the Exon Array data. On the left there are schematics depicting each type of alternative splicing event. Splicing events that could not be definitively categorized were classified as "ambiguous or complex." The table on the right displays the number of probesets, events, and genes that are associated with each type of splicing event.

The inventors categorized the different types of alternative splicing events and found that there is at least one example of every known type of alternative splicing event in the resulting list of high-confidence ESRP regulated splicing events (FIG. 9). Notably, the computational Alternative Conserved Exon (ACEScan) tool predicts 25 of the 143 events were ACEScan positive (including 21 out of the 68 cassette exons), indicating that they were highly likely (or known) to be evolutionarily conserved. The ACEScan data set was derived based on intronic sequence conservation between human and mouse genes that is indicative of conserved splicing events in both species and likely also reflects the presence of intronic binding sites for splicing regulatory factors. The enrichment of such exons indicates that alternative splicing of these exons is likely to be physiologically relevant. The largest group of splicing events consists of alternative cassette exons. However, the inventors also noted a large class of alternative splicing or polyadenylation events that result in the use of alternative 3' ends. These events can be sub-divided into alternative polyadenylation (polyA) sites or alternative 3' terminal exons. The inventors further categorized the alternative 3' terminal exons into two types. The inventors defined Type I events as those where an alternative 5' splice site is in competition with a polyA signal in the immediate downstream intron. Thus, in these events, when the 5' splice site is not used, the associated exon becomes the 3' terminal exon, whereas its use leads to use of an exon further downstream as the 3' terminal exon, often also including numerous additional downstream cassette exons. Type II events are defined as those in which competing 3' splice sites in different exons lead either to an upstream 3' terminal exons, or selection of a downstream exon as either the 3' terminal exon or continued use of additional 3' cassette exons (see schematic in FIG. 9).

Example 13

The ESRPs Regulate Inclusion and Skipping of Internal Cassette Exons

The ESRPs were predicted by the Exon Array data to both enhance and repress splicing of alternative cassette exons. A single probe set in the SLK transcript corresponding to exon 13 showed decreased expression in the ESRP knockdown (data not shown). This suggests that inclusion of SLK exon 13 is enhanced by the ESRPs. RT-PCR confirmed this prediction, showing that exon 13 inclusion decreases from 30% in the control to 2% when ESRP1 and 2 are down regulated (data not shown). The inventors further validated examples of ESRP enhanced cassette exons in the LOXL2 and TRIP10 transcripts. Inclusion of the LOXL2 and TRIP10 regulated exons decreased from 4.9% to 1.3% and 2.6% to 0.2%, respectively, upon ESRP knockdown (data not shown). An example of a cassette exon predicted to be repressed by the ESRPs is exon 16 in the SCRIB transcript. The single probe set associated with this exon showed increased levels of inclusion in the ESRP knockdown compared to the control (data not shown). RT-PCR shows the inclusion level of the exon increasing from 11% to 77% upon ESRP knockdown, validating this exon as being a target of ESRP repression (data not shown).

Example 14

The ESRPs, Regulate the Utilization of Alternative 3' and 5' Splice Sites within an Exon In addition to exon inclusion or skipping, the analysis also revealed that the ESRPs can regulate alternative 5' or alternative 3' splice site selection. CHRNA5 exon five has three alternative 5' splice sites and the use of these splice sites results in exons of 49 nt, 350 nt, and 836 nt. Four probe sets corresponding to the portion of the exon created by utilization of the most downstream 5' splice site, three of which were in the top 500 MADS probe sets, show increased expression upon ESRP knockdown (data not shown). This data indicates that the ESRPs repress splicing at the most downstream 5' splice site in CHRNA5 exon five. RT-PCR confirmed this prediction as the splice variant of CHRNA5 with the longest form of exon five increases from 5% to 18% upon ESRP knockdown. Utilization of both upstream 5' splice sites decreased when the ESRPs were down regulated. The amount of the shortest form and intermediate form of exon five decreased from 19% to 10% and 76% to 72%, respectively (data not shown).

As an example of an alternative 3' splice site choice regulated by the ESRPs, the inventors validated the predicted change in 3' splice site utilization in FAM62A exon 14. A single probe set that corresponds to the portion of exon 14 formed by splicing at the upstream 3' splice site showed decreased expression upon ESRP knockdown relative to the control suggesting that ESRP promotes splicing of this exon at the upstream 3' splice site. RT-PCR analysis clearly confirmed this prediction, with the level of transcripts including the long form of exon 14 decreasing from 23% to 5% (data not shown). The inventors also observed that in four of the five examples of alternative 5' splice site selection, the ESRPs are predicted to favor splicing at the upstream 5' splice site. Similarly, in four of the five examples of alternative 3' splice site selection, the ESRPs are predicted to favor splicing at the upstream 3' splice site. Such a preferential function provides clues as to how the ESRPs regulate splicing at the molecular level.

Example 15

The ESRPs Regulate Splicing of Mutually Exclusive Cassette Exons

Within the high-confidence list of ESRP regulated splicing events (See, e.g., Tables 1-5) was one example of a mutually exclusive splicing event. A single probe set from the MADS data predicted increased expression of an exon directly upstream of exon 4 in the OGDH transcript. OGDH mRNA and EST alignments strongly suggest that the MADS exon, which the inventors termed exon 4a, and exon 4 are spliced in a mutually exclusive manner. Despite the probe set for exon 4 being absent from the MADS top 500 list the inventors performed an RT-PCR assay to validate the predicted increase in exon 4a inclusion and the reciprocal decrease in exon 4 inclusion. To distinguish between the two amplicons of similar size, the inventors digested the PCR products with Pvu II and BstE II restriction enzymes that uniquely cut exon 4 and exon 4a, respectively (data not shown). Splicing of exon 4a is increased in the ESRP knockdown, from 19% to 48% inclusion, as predicted by MADS. Conversely, exon 4 is included in 81% of the OGDH transcripts in the control but decreases to 52% inclusion when the ESRPs are down regulated. Furthermore, there was no indication of double-inclusion or double-skipping of the two exons. This result validates the MADS prediction as well as the interpretation that the alternative splicing event detected by the MADS is of the mutually exclusive type. Interestingly, this is not analogous to the role the ESRPs play in the regulation of FGFR2 mutually exclusive splicing where the ESRPs favor splicing of the upstream mutually exclusive exon and silencing of the downstream exon. In the case of OGDH, the ESRPs appear to promote splicing of the downstream exon over that of the upstream exon (but see also below).

Example 16

The ESRPs Co-Regulate Splicing of Tandem Sets of Exons

The inventors previously demonstrated that the ESRPs regulated multiple, tandem exons within the CD44 and CTNND1 gene transcripts. The MADS analysis revealed additional tandem alternative exons regulated by the ESRPs and two examples are illustrated here. Two probe sets in MYO1B corresponding to exons 24 and 25, showed increased inclusion in the ESRP knockdown, indicating that these exons are normally silenced by the ESRPs (data not shown). RT-PCR confirmed that both of these exons are targets of ESRP repression. In the control, products containing both exons 24 and 25 make up 5% of the MYO1B transcripts compared to 26% in the ESRP knockdown sample (data not shown). A PCR product representing single exon inclusion is also seen at a low level and the inventors verified that this single inclusion product is a mix of products including either the upstream or the downstream exon alone (data not shown).

The second example of a pair of tandem exons regulated by the ESRPs is in the ADAM15 transcript where the probe sets for exons 20 and 21 were shown to decrease in the knockdown sample compared to the control as detected in our MADS analysis (data not shown). Unlike the case of the MYO1B exons, the two exons in ADAM15 were predicted to be enhanced by the ESRPs. RT-PCR analysis revealed three major splice isoforms corresponding to skipping of both exons, single inclusion of one or the other exon, and inclusion of both exons (data not shown). As predicted by the array data, the splice variants containing one or both of these exons decrease in the ESRP knockdown, while those that skip both increase in abundance. This result confirms that splicing of exons 20 and 21 in ADAM15 are enhanced by the ESRPs.

Example 17

The ESRPs Regulate Splicing of Alternative Terminal Exons

An unexpectedly prevalent regulatory function of the ESRPs unveiled by the MADS analysis was alternative splicing of 3' terminal ends or alternative polyadenylation (see description above). A recent study showed that these events are widespread, occurring in up to 20% of human genes. Many of these types of events dramatically change the size and sequence of the resulting proteins more than is typically achieved through alternative splicing of cassette exons. Thus, it is perhaps more likely that some of these events may more significantly affect the physiological functions of the alternative isoforms. A total of 36 of these events were in our list of high-confidence list of alternative splicing targets (data not shown). Identification of these events was made possible not only by the exon probesets identified by MADS, but by using the complete set of probe sets for each transcript to detect reciprocal changes in expression between the upstream and downstream terminal exons as analyzed in the Geneview feature of the Partek software program. The inventors selected several alternative 3' terminal exon events, including both Type I and Type II events, for independent RT-PCR validation and present two examples here. The inventors used a competitive PCR approach that employed a common forward primer and reverse primers specific to each alternative 3' end. The disadvantage of this method is that it cannot be used as accurately to determine the true ratio of the alternative splice variants as in the case of cassette exons using common PCR primers. However, this approach was sufficient to detect robust changes in splicing mediated by the ESRPs in the validation assays.

Exon 2 of the SP1 gene transcript has a 5' splice site in competition with a polyA signal. When the 5' splice site in exon two is used, it is spliced to exon three and the remaining downstream exons. Conversely, when this 5' splice site is not used, the SF1 transcript is polyadenylated and terminates in the intron immediately downstream of exon two, thereby encoding a significantly truncated isoform of SF1 (data not shown). Our analysis of the MADS data predicted the Type I alternative 3' end splicing of the SF1 gene to be a target of ESRP regulation. Three of the five probe sets corresponding to the portion of exon two created by skipping of its 5' splice site were present in the MADS top 500 and show increased expression in the knockdown while the probe sets corresponding to the downstream exons display decreased expression (data not shown). Together, these results suggest that the ESRPs enhance splicing of exon two to the downstream exons and when they are depleted there is increased polyadenylation in the intron downstream of exon two. This prediction was confirmed by RT-PCR. In the control, the predominant splicing product is the full length SF1 transcript. When the ESRPs are down regulated, the inventors observe a decrease in the full-length transcript and an increase in the truncated splice variant (data not shown). The inventors validated an additional Type I alternative 3' end splicing target of the ESRPs in the SF3B1 gene transcript (data not shown).

The EPB41L5 gene transcript undergoes Type II alternative 3' end splicing. In the EPB41L5 transcript, exon 16 can be spliced to the upstream terminal exon 17, with polyadenylation and termination occurring in the intron downstream of exon 17. Alternatively, exon 17 can be skipped and exon 16 is spliced to exon 18 and the numerous remaining exons in the transcript. Similar to SF1, splicing to exon 17 in the EPB41L5 transcript would result in a significantly truncated protein.

Four probe sets corresponding to the downstream exons in EPB41L5 were in the MADS top 500 list. The MADS probe sets as well as the rest of the probe sets corresponding to the EPB41L5 exons downstream of exon 17 showed increased expression. The two probe sets corresponding to the alternative terminal exon 17 showed a converse decrease in expression. These data indicate that the ESRPs enhance splicing of exon 17, therefore promoting the shorter EPB41L5 isoform. RT-PCR confirmed this to be true. In the control, almost all EPB41L5 terminates at exon 17. However, when the ESRPs are down regulated, the inventors observe a mix of both the short and long splice variants of EPB41L5. The inventors also validated two additional Type II alternative 3' end splicing targets of the ESRPs (CUL4A, and GIT2) and established that the ESRPs promote splicing of the upstream terminal exon in these two cases as well (data not shown).

Example 18

Additional Validation of Predicted ESRP Regulated Splicing Events

In total, the inventors tested 18 alternative splicing events from the list of high-confidence ESRP targets ourselves by RT-PCR. Of these 18, the inventors were able to validate 15 novel alternative splicing events regulated by the ESRPs (Table 3). We note, however, that one of the events that was not validated was a predicted retained intron in RBM39. While this retained intron was not validated, an increase in the inclusion of a known alternative cassette exon in RBM39 flanked by this intron was observed in response to ESRP knockdown. To further validate changes in splicing associated with down-regulation of the ESRPs, the inventors submitted RNA samples for high-throughput (HT) RT-PCR using high-resolution capillary electrophoresis (data not shown). This analysis was used to investigate an additional 35 targets with two RT-PCR reactions per target. To facilitate direct analysis of the products and simplify the design of PCR primers for this approach, the inventors necessarily focused our use of this method mostly towards analysis of simple, single alternative cassette exons. These examples demonstrate clear changes in splicing of the ESRP enhanced exon in the FNIP1 gene transcript and the ESRP silenced exons in OSBPL3, and GOLGA4 gene transcripts. In total, 25 of the 35 events the inventors tested were confirmed to be valid changes in splicing as predicted by the array data. Four of the ten targets that the inventors were unable to validate (NASP, TGFBR2, PRMT1, GPR126 [probe set 2928530]) turned out to suffer from errors or ambiguities in primer design and were thus removed from the overall analysis as no conclusions could be drawn. Exon two of the NT5C3 gene transcript (probeset 3045024) was predicted to be enhanced by the ESRPs, but RT-PCR results showed that exon inclusion increased upon ESRP depletion. This contradiction might be explained by the presence of alternative first exons, only one of which was targeted by the PCR primers. Four events demonstrated (OSBPL3, DZIP1, ASPH, and TIA1 [probe set 2558539 small changes in splicing that did not pass our threshold of an 1.0% change in splicing or a change was only detected by one of the two primer pairs, but the changes did match the corresponding prediction. Thus, several of these exons may in fact be regulated by the ESRPs, but without additional replicates, the inventors cannot confidently conclude that these are validated splicing targets.

Combining this data with the validations summarized in Table 3, the inventors validated a change in splicing of a total of 38 out of 49 tested splicing events that were identified in the top 500 of the MADS analysis. Thus, at a minimum 78% of the splicing events that the inventors subjected to further validation could be confidently concluded to represent true ESRP regulated splicing events. Specifically, the splicing events indicated in Tables 1-2 above, particularly those over 30% or more inclusion represent true ESRP regulated splicing events.

Example 19

Depletion of ESRP1, but not ESRP2, is Sufficient to Induce Switching Towards Mesenchymal Splicing Patterns To further investigate functional redundancy between ESRP1 and ESRP2 as well as the relative requirements for each factor in maintaining epithelial splicing pathways, mRNAs encoding each protein were individually depleted as well in combination, as was previously done for the exon array. The inventors then assayed splicing of two gene transcripts with simple cassette exons that displayed robust changes in splicing in response to ESRP1 and ESRP2 depletion (data not shown). Depletion of ESRP1 alone was sufficient to induce a partial increase in splicing of the SCRIB exon and combined depletion of both ESRP1 and ESRP2 caused a further increase in exon inclusion. In contrast, depletion of ESRP2 alone was not sufficient to induce a change in splicing of this exon. In the case of SLK, depletion of ESRP1 alone partially induced exon skipping which was similarly augmented by combined depletion of ESRP1 and ESRP2 (data not shown). However, depletion of ESRP2 alone was unable to induce exon skipping and if anything a slight increase was observed. The specificity and efficacy of knocking down each factor was validated by quantitative RT-PCR (data not shown). These results thus suggest that while ESRP1 and ESRP2 generally have functionally redundant activities, expression of ESRP1 would appear to have more essential functions in splicing regulation (see also below).

Example 20

Ectopic Expression of mEsrp1 in a Mesenchymal Cell Line Induces Reciprocal Changes in Splicing of ESRP Target Gene Transcripts To further investigate the role of the ESRPs in regulation of these novel splicing targets, the inventors tested whether ectopic expression of the ESRPs was also sufficient to promote the opposite changes in splicing in a mesenchymal cell line as those seen in epithelial cells upon ESRP depletion. The inventors previously showed (Example 10) that ectopic expression of a mouse Esrp1 cDNA in the mesenchymal human breast cancer cell line MDA-MB-231 was in fact sufficient to induce the opposite changes in splicing of FGFR2, CD44, ENAH, and CT7VND1 from those seen with ESRP depletion in the PNT2 cell line. Using this experimental system, the inventors tested the effect of mEsrp1 expression on splicing of the 18 splicing events that we could test ourselves using the primers sets we had for RT-PCR (Table 3). The ESRP regulated exons in the FLNB and SLK transcripts are included at low levels in the control 231 cells (EV). Expression of mEsrp1 greatly enhances splicing of these exons (data not shown). Two examples of exons that are suppressed by the ESRPs are also shown (data not shown). The SCRIB alternative exon is included in 58% of transcripts in the control cells where cells expressing mEsrp1 only splice this exon in 9% of transcripts. In the case of MYO1B, inclusion of the tandem exons is strongly silenced as the percentage of transcripts containing one or both exons decreases from 31% to 8% upon mEsrp1 expression. Finally, an example of mEsrp1 being sufficient to alter alternative 3' end splicing is shown for the EPB41L5 transcript (data not shown). In the control cells, there is a nearly equal mix of the short and long splice variant of EPB41L5. However, when mEsrp1 is expressed in these cells, the long splice variant is almost completely down-regulated in favor of the truncated splice variant. In total, out of the 15 targets that were confirmed in the PNT2 ESRP knockdown experiment, 8 showed reciprocal changes in splicing upon ectopic expression of mEsrp1 in the MDA-MB-231 cells (data not shown). Interestingly, while not a true "validated" splicing change, the cassette exon in RBM39 also showed a reciprocal change from that observed upon ESRP knockdown (data not shown). Unexpectedly, the direction of change in splicing of the mutually exclusive exons in the OGDH transcript was the same in the mEsrp1 expression system as it was in the ESRP knockdown experiment (data not shown). One possible explanation for this unexpected finding could be that the ESRPs have differential effects on splicing of one or both exons in different cellular milieus, or that they may indirectly regulate these exons. Given that most exons are under regulation by complex combinatorial control by multiple regulatory factors, it is possible that antagonistic functions of the ESRPS may be due to interactions with different regulatory proteins in different cell types. However, at present we cannot provide a simple explanation to account for this seemingly contradictory observation.

Six of the validated splicing changes observed in response to ESRP knockdown showed no change in response to mEsrp1 expression in mesenchymal cells. One possible explanation was that some of these events might instead be specifically regulated by ESRP2. To address this possibility, the inventors analyzed the splicing of these targets in MDA-MB-231 cells when mEsrp1, mEsrp2, or both proteins together were ectopically expressed. In five of these six cases (FAM62A, CUL4A, TRIP10, SF3B1, and SF1) neither mEsrp1, mEsrp2, nor a combination of both induced splicing changes. In the case of the CHRNA5 alternative 5' splice site there did appear to be evidence that mEsrp2 could induce a change in splicing that was not achieved by mEsrp1, but the effect was small (data not shown). As controls, the inventors also tested the effects of ectopic expression of both paralogs on splicing of SLK and SCRIB. In both cases the inventors noted that mEsrp1 induced more profound changes in splicing than mEsrp2 and co-expression of both proteins showed no evidence of additive functions. (Data not shown). Thus, together with the results from independent ESRP1 and ESRP2 knockdown, these results suggest that these proteins have similar, redundant functions, but that ESRP2 may be a less robust splicing factor than ESRP1. It is possible, particularly for the alternative 3' terminal exon splicing events that are often difficult to validate, that these assays may have been unable to detect some mEsrp1 induced splicing changes. However, it may be more likely that for some of these types of splicing events, the ESRPs are necessary for expression of epithelial isoforms, but ectopic expression of mEsrp1 alone may not be sufficient to promote a switch in splicing from the mesenchymal to the epithelial pathway. Here too it is possible that some of the discrepancies might be due to indirect effects on splicing in one or both experimental systems. Nonetheless, taken together the results from the ectopic expression experiments support the conclusion that the ESRPs are in fact bona fide regulators of most of the splicing changes identified in the MADS analysis of the microarray data.

Example 21

ESRP Target Genes Share Common Functions and Biological Processes, Including Numerous Examples of Genes that Function in Cell-Cell Adhesion and Cell Motility The inventors were interested in investigating whether the set of ESRP splicing targets the inventors identified could be shown to function in any common pathways are have related biological roles. As a first step in such analysis, the 134 genes from the list of high-confidence splicing events within the MADS top 500 probe sets were analyzed for enriched Gene Ontology (GO) terms using the DAVID Bioinformatics Resource. DAVID was unable to map the following four genes (MNAT, AGFG1, PMS2L14, ARFGAP2) and thus, these are absent in the analysis. Compared to the background set of all genes represented by probesets on the Exon Arrays, the inventors noted several GO terms that were enriched among the genes in the high confidence list. Though not all of the predicted splicing events in the 134 genes analyzed have been validated, the validations performed suggest that most of the genes in this list are true targets. Furthermore, any false positives would not be predicted to cluster in a way that would further support the observed enrichment.

This analysis, summarized in Table 7 below and Table 4 above suggested that many of the ESRP target genes encode proteins involved in cytoskeleton structure, cell adhesion, RNA splicing, and the other categories presented. Tables 4 and 7 depict a subset of ESRP target genes which regulate cytoskeleton structure and cell adhesion. Gene Ontology (GO) analysis was performed on the ESRP targets. The number of ESRP targets in each GO category, the enrichment for each category, and the corresponding p-values are listed.

TABLE 7

| Number of ESRP targets | % of ESRP targets within GO category | % of Non-ESRP targets within GO category | GO term | p-value |
|---|---|---|---|---|
| Molecular Function | | | | |
| 9 | 7.1 | 2.3 | Cytoskeletal protein binding | 8.7E−3 |
| 12 | 9.4 | 3.8 | RNA binding | 9.0E−3 |
| 4 | 3.1 | 0.5 | Structural constituent of cytoskeleton | 2.2E−2 |
| 4 | 3.1 | 0.5 | Protein tyrosine phosphatase activity | 3.1E−2 |
| Cytoplasmic Component | | | | |

TABLE 7-continued

| Number of ESRP targets | % of ESRP targets within GO category | % of Non-ESRP targets within GO category | GO term | p-value |
|---|---|---|---|---|
| 68 | 53.5 | 35.7 | Cytoplasm | 2.0E−5 |
| 16 | 12.6 | 6.3 | Cytoskeleton | 2.1E−2 |
| Biological Process | | | | |
| 12 | 9.4 | 4.1 | Cell adhesion | 1.6E−2 |
| 6 | 4.7 | 1.2 | Protein targeting | 1.9E−2 |
| 5 | 3.9 | 0.8 | Dephosphorylation | 1.9E−2 |
| 6 | 4.7 | 1.3 | RNA splicing | 2.3E−2 |

The inventors wished to further investigate whether relevant biological functions or themes could be identified among the list of ESRP target genes and thus the inventors also carried out an extensive literature review of these gene products. A subset of these genes could be shown to encode proteins with important roles in the regulation of the actin cytoskeleton, cell-cell adhesion, and cell motility and migration (data not shown). Among these gene products were a number that have well documented and essential roles in epithelial to mesenchymal transitions and maintenance of cell polarity in addition to the previously reported FGFR2, p120-catenin, CD44, and ENAH. Such genes include, for example, EPB41L5, SCR1B, MACF1 (ACF7), GIT2, LOXL2, FAT, and PTPRM. See also Table 4. The inventors also noted a number of cases in which these gene products have been shown to physically associate with one another in the regulation of these cell behaviors. These observations thus suggest both that many of these targets function in common pathways and imply that the different splice variants may well prove to have different, or even opposing functions in epithelial and mesenchymal cells as has already been demonstrated for FGFR2 and p120-catenin.

Example 22

Validated Target Genes

Subsequent to validation of the experimental method described in the preceding examples, the inventors used siRNA-mediated depletion and exon microarrays to identify additional splicing events regulated by ESRP1 and ESRP2. The data described above represent the use of the Affymetric Exon Array ST1.0 splicing sensitive array to detect changes in splicing upon siRNA mediated depletion of ESRP1 and ESRP2 in the epithelial PNT2 cell line. We have since extended this analysis using another splicing sensitive microarray platform. This platform uses both exon and exon junction probesets to profile splicing changes and is referred to as the Exon Junction array. In total we used both the Exon Array and Exon Junction array to identify changes in splicing in PNT2 cells with ESRP1 and ESRP2 depletion. We also used both arrays to profile splicing changes induced by ectopic expression of a cDNA for mouse Esrp1 in the mesenchymal MDA-MB-231 cell line. Numeorus validations of these changes in splicing were carried out using RT-PCR or high throughput capillary RT-PCR. The most significant changes that were validated from primary data achieved through any of these approaches or platforms are summarized in Tables 1, 2 and 3.

Example 23

ESRP-Like Compounds

Another aspect of the invention is to identify compounds that affect the epithelial mesenchymal transition in a way similar to that of ESRP1 and ESRP2. To accomplish this, the inventors identified compounds that activated splicing in the luciferase reporter screen using the LOPAC 1280™ library of compounds, a group of high purity, small organic ligands.

Briefly, compounds from the LOPAC™ library were dissolved in DMSO. 293T cells (which express predominantly FGFR2-IIIc) which stably express the PKC-neg-40B-Luc minigene, as described in Example 1, were incubated with the compounds or with a DMSO control for 24 hours. After the incubation period, BriteLite luciferase readout reagent was added to each well and the plates were read on an Analyst HT multimode plate reader (Molecular Devices). As positive controls, we also added a cDNA encoding the mouse Esrp1 protein to individual wells on each plate.

The results were then ranked in order from largest fold change over background down to the DMSO blank. Any average reading over the DMSO control (approximately 1.75 fold over background) was considered to be a possible ESPR mimicking compound. After analysis, the top ranking wells were, not surprisingly, the controls expressing the Esrp1 protein. Additionally, phorbol 12-myristate 13-acetate (PMA), phenylazo-3-phyridinol, podophyllotoxin, R(−)-isoproterenol (+)-bitartrate, and beclomethasone ethylcarboxamido adenosine were found to have luciferase readings significantly over the background reading (See, Table 5).

All publications cited in this specification, including the references identified below and the provisional application U.S. No. 61/082,435, are incorporated herein by reference. In addition, Warzecha, et al, Molecular Cell, 33:591-601 (March 2009) including all of the supplemental materials published online as of the publication date, is specifically incorporated in its entirety by reference. While the invention has been described with reference to a particularly preferred embodiment, it will be appreciated that modifications can be made without departing from the spirit of the invention. Such modifications are intended to fall within the scope of the appended claims References
1. Acevedo, et al., (2007) Cancer Cell 12, 559-571.
2. Allemand, et al., (2005) Proc Natl Acad Sci USA 102, 3605-3610.
3. Baraniak, et al., (2006) Mol Cell Biol 26, 1209-1222.
4. Barberan-Soler, et al., (2008) PLoS Genet 4, e1000001.
5. Barberi, et al., (2005). PLoS Med 2, e161.
6. Black, D. L. (2003) Annu Rev Biochem 72, 291-336.

7. Blanco, et al., (2002) Oncogene 21, 3241-3246.
8. Blencowe, B. J. (2006) Cell 126, 37-47.
9. Boutros, M., and Ahringer, J. (2008). Nat Rev Genet 9, 554-566.
10. Boutz, et al., (2007) Genes Dev 21, 71-84.
11. Cano, et al., (2000) Nat Cell Biol 2, 76-83.
12. Carstens, et al., (1997) Oncogene 15, 3059-3065.
13. Carstens, et al., (1998) Mol Cell Biol 18, 2205-2217.
14. Carstens, et al., (2000) Mol Cell Biol 20, 7388-7400.
15. Cha, et al., (2008) Mol Cancer Res 6, 435-445.
16. Chaffer, et al., (2007) Cells Tissues Organs 185, 7-19.
17. Charlet, et al., (2002) Mol Cell 9, 649-658.
18. Cussenot, et al., (1991) 3 Urol 146, 881-886.
19. Dauwalder, et al., (1996) Proc Natl Acad Sci USA 93, 9004-9009.
20. David, et al., (2008). Genes Dev 22, 279-285.
21. De Moerlooze, et al., (2000) Development 127, 483-492.
22. Feng, et al., (1997) Cancer Res 57, 5369-5378.
23. Forch, P., and Valcarcel, J. (2003) Prog Mol Subcell Biol 31, 127-151.
24. Gerhard, et al., (2004) Genome Res 14, 2121-2127.
25. Gregory, et al., (2008) Nat Cell Biol 10, 593-601.
26. Grose, et al., (2007) Embo J 26, 1268-1278.
27. Hanamura, et al., (1998) Rna 4, 430-444.
28. Hedley, M. L., and Maniatis, T. (1991) Cell 65, 579-586.
29. Hertel, K. J. (2008) J Biol Chem 283, 1211-1215.
30. Hieronymus, H., and Silver, P. A. (2004) Genes Dev 18, 2845-2860.
31. Hovhannisyan, R. H., and Carstens, R. P. (2005) Mol Cell Biol 25, 250-263.
32. Hovhannisyan, R. H., and Carstens, R. P. (2007) J Biol Chem 282, 36265-36274.
33. Hovhannisyan, et al., (2006) Nucleic Acids Res 34, 373-385.
34. Hu, A., and Fu, X. D. (2007) Nat Struct Mol Biol 14, 174-175.
35. Huang, et al., (2007) Cancer Res 67, 11147-11157.
36. Itoh, et al., (1994) Cancer Res 54, 3237-3241.
37. Ivanov, et al., (2007) Oncogene 26, 2873-2884.
38. Kar, et al., (2006) J Biol Chem 281, 24479-24488.
39. Karni, et al., (2007) Nat Struct Mol Biol 14, 185-193.
40. Keene, I. D. (2007) Nat Rev Genet 8, 533-543.
41. Kuroyanagi, et al., (2007) Mal Cell Biol 27, 8612-8621.
42. Ladd, A. N., Charlet, N., and Cooper, T. A. (2001) Mol Cell Biol 21, 1285-1296.
43. Li, Q., Lee, J. A., and Black, D. L. (2007) Nat Rev Neurosci 8, 819-831.
44. Licatalosi, D. D., and Darnell, R. B. (2006) Neuron 52, 93-101.
45. Lin, et al., (2007) Development 134, 723-734.
46. Lopez, A. J. (1998) Annu Rev Genet 32, 279-305.
47. Luqmani, et al., (1996) Eur J Cancer 32A, 518-524.
48. Lynch, K. W., and Maniatis, T. (1996) Genes Dev 10, 2089-2101.
49. Makeyev, et al., (2007) Mol Cell 27, 435-448.
50. Matlin, et al., (2005) Nat Rev Mol Cell Biol 6, 386-398.
51. McKee, et al., (2005) BMC Dev Biol 5, 14.
52. McKeehan, et al., (1998) Prog Nucleic Acid Res Mal Biol 59, 135-176.
53. Min, et al., (1998) Genes Dev 12, 3156-3161.
54. Moffa, et al., (2007) J Cell Physiol 210, 720-731.
55. Moffat, J., and Sabatini, D. M. (2006) Nat Rev Mol Cell Biol 7, 177-187.
56. Moody, et al., (2005) Cancer Cell 8, 197-209.
57. Newman, et al., (2006) Rna 12, 1129-1141.
58. Onder, et al., (2008) Cancer Res 68, 3645-3654.
59. Orengo, et al., (2006) Nucleic Acids Res 34, e148.
60. Orr-Urtreger, et al., (1993) Dev Biol 158, 475-486.
61. Orwig, et al., (2008) Stem Cells 26, 927-938.
62. Park, et al., (2008) Genes Dev 22, 894-907.
63. Ponthier, et al., (2006) J Biol Chem 281, 12468-12474.
64. Pritsker, et al., (2005) Proc Natl Acad Sci USA 102, 14290-14295.
65. Relogio, et al., (2005) J Biol Chem 280, 4779-4784.
66. Ricol, et al., (1999) Oncogene 18, 7234-7243.
67. Rines, et al., (2006) Methods Enzymol 414, 530-565.
68. Savagner, et al., (1994) Mol Biol Cell 5, 851-862.
69. Sekine, et al., (1999) Nat Genet 21, 138-141.
70. Shankavaram, et al., (2007) Mol Cancer Ther 6, 820-832.
71. Sherwood, et al., (2007) Dev Cell 304, 541-555.
72. Smith, C. W., and Valcarcel, J. (2000) Trends Biochem Sci 25, 381-388.
73. Stamm, S. (2008) 3 Biol Chem 283, 1223-1227.
74. Stamm, et al., (2005) Gene 344, 1-20.
75. Thiery, J. P. (2002) Nat Rev Cancer 2, 442-454.
76. Thomson, A. A., and Cunha, G. R. (1999) Development 126, 3693-3701.
77. Tian, M., and Maniatis, T. (1992) Science 256, 237-240.
78. Ule, et al., (2005) Nat Genet 37, 844-852.
79. Wakabayashi-Ito, et al., (2001) Dev Biol 229, 44-54.
80. Wu, et al., (2006) Mol Cell Biol 26, 6739-6747.
81. Xu, et al., (1998) Development 125, 753-765.
82. Yan, et al., (1993) Mol Cell Biol 13, 4513-4522.
83. Yang, et al., (2004) Cell 117, 927-939.
84. Yang, J., and Weinberg, R. A. (2008) Dev Cell 14, 818-829.
85. Yasumoto, et al., (2004) Prostate 61, 236-242.
86. Zhang, et al., (2006) J Biol Chem 281, 15694-15700.
87. Zhang, et al., (2001) Proc Natl Acad Sci USA 98, 11336-11340.
88. Arman, et al., 1999 Proc Natl Acad Sci USA 96:11895-9.
89. Feng, et al., 1997 Cancer Res 57:5369-78.
90. Grose, R., and C. Dickson. 2005 Cytokine Growth Factor Rev 16:179-86.
91. Matsubara, et al., 1998 Cancer Res 58:1509-14.
92. McKeehan, W. L., F. Wang, and M. Kan. 1998 Prog Nucleic Acid Res Mol Biol 59:135-76.
93. Orr-Urtreger, et al., 1993Dev Biol 158:475-86.
94. Xu, et al., 1998 Development 125:753-65.
95. Yang, et al., 2004 Cell 117:927-39.

The invention claimed is:

1. A screening method for identifying a compound that causes an epithelial to mesenchymal transition (EMT) in a normal mammalian cell comprising:
   (a) adding a test compound to an in vitro biological sample obtained from a mammalian subject, which consists of normal healthy mammalian cells;
   (b) contacting said biological sample containing the test compound with reagents that can measure or detect the expression level of alternative splice variants of each of genes SLC37A2, FLNB, RALGPS2, ENAH, FNIP1, ARFGAP2, SLK, SCRIB and ARHGEF11 or the proteins encoded thereby;
   (c) performing an assay to measure the levels of expression of the splice variants; and
   (d) identifying a test compound as causing an EMT in the sample when
      i. the levels of expression of the splice variants of SLC37A2, FLNB, RALGPS2, ENAH, FNIP1, ARFGAP2, and SLK in the sample containing the test compound are below the level of expression of those splice variants in the sample in the absence of the test compound, and
      ii. when the level of expression of the splice variants of SCRIB and ARHGEF11 in the sample containing the test compound are above the level of expression of those splice variants in the sample in the absence of the test compound,
   wherein the splice variant of:
      SLC37A2 includes the exon sequence SEQ ID NO: 1,
      FLNB includes the exon sequence SEQ ID NO: 2,
      RALGPS2 includes the exon sequence SEQ ID NO: 3,
      ENAH includes the exon sequence SEQ ID NO: 4,
      FNIP1 includes the exon sequence SEQ ID NO: 31,
      ARFGAP2 includes the exon sequence SEQ ID NO: 7,
      SLK includes the exon sequence SEQ ID NO: 9;
      SCRIB excludes the exon sequence SEQ ID NO: 20, and
      ARHGEF11 excludes the sequence SEQ ID NO: 33.

2. The method according to claim 1, wherein the contacting step comprises measuring the splice variants as ribonucleic acid, deoxyribonucleic acid, cDNA sequence or protein.

3. The method according to claim 2, wherein the reagents that can measure or detect the expression of the splice variants are PCR primers or probes that identify the nucleic acid sequences of the specified splice variants, or antibodies or ligands that identify the variant proteins encoded by the splice variant nucleic acid sequences.

4. The method according to claim 3, wherein the contacting comprises forming a physical association between the reagent and the nucleic acid sequence or protein in the sample.

5. The method according to claim 3 further comprising transforming a signal generated from the reagent in association with the splice variants present in the biological sample into numerical or graphical data.

6. The method according to claim 3, further comprising extracting RNA from the sample and contacting the extracted RNA sample with the reagents.

7. The method according to claim 1, wherein the biological sample is selected from the group consisting of mammalian cells, biological fluids containing mammalian cells, and mammalian tissue.

8. The method according to claim 7, wherein the sample is blood.

9. The method according to claim 1, wherein the assay is performed using polymerase chain reaction (PCR).

10. The method according to claim 9, wherein the assay is performed using quantitative real-time polymerase chain reaction.

11. The method according to claim 9, wherein said assay is performed using a reverse transcriptase PCR exon splicing assay.

* * * * *